US012796976B2

(12) United States Patent

Matichuk et al.

(10) Patent No.: US 12,796,976 B2
(45) Date of Patent: Nov. 17, 2026

(54) HEALTH SENSOR USING MULTIPLE LIGHT EMITTING DIODES

(71) Applicant: MedWatch Technologies, Inc., Las Vegas, NV (US)

(72) Inventors: Bruce Matichuk, Alberta (CA); Mike Moore, Las Vegas, NV (US)

(73) Assignee: MedWatch Technologies, Inc., Las Vegas, NV (US)

( * ) Notice: Subject to any disclaimer, the term of this patent is extended or adjusted under 35 U.S.C. 154(b) by 297 days.

(21) Appl. No.: 18/582,540

(22) Filed: Feb. 20, 2024

(65) Prior Publication Data

US 2025/0082234 A1 Mar. 13, 2025

Related U.S. Application Data

(60) Provisional application No. 63/446,613, filed on Feb. 17, 2023.

(51) Int. Cl.
*A61B 5/00* (2006.01)
*A61B 5/01* (2006.01)
(Continued)

(52) U.S. Cl.
CPC ............ *A61B 5/14552* (2013.01); *A61B 5/01* (2013.01); *A61B 5/02427* (2013.01);
(Continued)

(58) Field of Classification Search
CPC ... A61B 5/14552; A61B 5/01; A61B 5/02427; A61B 5/0533; A61B 5/14532;
(Continued)

(56) References Cited

U.S. PATENT DOCUMENTS 9,420,956 B2 8/2016 Gopalakrishnan et al.
9,554,738 B1 1/2017 Gulati et al.
(Continued)

FOREIGN PATENT DOCUMENTS

AU 2023229292 A1 10/2024
AU 2023269185 A1 11/2024
(Continued)

OTHER PUBLICATIONS

International Search Report and Written Opinion, (ISRWO), Application No. PCT/US2024/016553, pp. 1-17, dated Jul. 12, 2024.

*Primary Examiner* — Lindsey G Wehrheim
(74) *Attorney, Agent, or Firm* — James Scott Nolan

(57) ABSTRACT

Provided herein is a non-invasive, continuous biometric sensor system for determining a characteristic of a state of a user based on a value of a biomolecule. The system includes a biomolecule sensing device and attachment structure for coupling the sensor to the body. The biomolecule sensing device is configured for generating digital signal read data pertaining an effect of a biomolecule on the tissues of the body such as by employing Near Infrared Spectroscopy (NIS) techniques. Accordingly, the sensing device includes electronic sensing components having a photoemitter for directing electromagnetic radiation into the tissue of a body, the tissue suspected of being affected by the presence of the biomolecule, and a photoreceiver for receiving electromagnetic radiation reflected back from the tissue. The reflected electromagnetic radiation may then be used by the system to determine a presence and/or concentration of a biomolecule of interest and/or its effect on the user.

20 Claims, 19 Drawing Sheets

(51) Int. Cl.
*A61B 5/024* (2006.01)
*A61B 5/0533* (2021.01)
*A61B 5/145* (2006.01)
*A61B 5/1455* (2006.01)

(52) U.S. Cl.
CPC ........ *A61B 5/0533* (2013.01); *A61B 5/14532* (2013.01); *A61B 5/1455* (2013.01); *A61B 5/7264* (2013.01)

(58) Field of Classification Search
CPC . A61B 5/1455; A61B 5/7264; A61B 5/02416; A61B 5/6833; G16H 50/20; G16H 50/30; G16H 40/63; H04Q 9/00
See application file for complete search history.

(56) References Cited

U.S. PATENT DOCUMENTS

| | | | |
|---|---|---|---|
| 9,582,072 | B2 | 2/2017 | Connor |
| 9,750,977 | B2 | 9/2017 | Yuen et al. |
| 9,826,940 | B1 | 11/2017 | Lengerich |
| 10,153,537 | B2 | 12/2018 | Baringer et al. |
| 10,321,873 | B2 | 6/2019 | Connor |
| 10,327,674 | B2 | 6/2019 | Hong et al. |
| 10,512,407 | B2 | 12/2019 | Richards et al. |
| 10,700,774 | B2 | 6/2020 | Panther et al. |
| 10,878,959 | B1 | 12/2020 | Reykhert |
| 10,880,724 | B2 | 12/2020 | Song et al. |
| 10,998,101 | B1 | 5/2021 | Tran et al. |
| 11,029,199 | B2 | 6/2021 | Turgeon et al. |
| 11,096,601 | B2 | 8/2021 | Hong et al. |
| 11,116,448 | B1 | 9/2021 | Trapero Martin et al. |
| 11,141,129 | B1 * | 10/2021 | Trapero Martin ... A61B 5/6823 |
| 11,152,664 | B2 * | 10/2021 | Reykhert ............ H05K 7/1427 |
| 11,166,635 | B2 | 11/2021 | Trapero Martin et al. |
| 11,207,025 | B1 | 12/2021 | Trapero Martin et al. |
| 11,357,426 | B2 | 6/2022 | Tran |
| 11,694,533 | B2 | 7/2023 | Shelton, IV et al. |
| 11,754,542 | B2 | 9/2023 | Connor |
| 11,766,216 | B2 | 9/2023 | Zilkie et al. |
| 11,786,251 | B2 | 10/2023 | Shelton, IV et al. |
| 11,806,109 | B2 | 11/2023 | Yuen et al. |
| 2015/0119725 | A1 | 4/2015 | Martin et al. |
| 2015/0320588 | A1 | 11/2015 | Connor |
| 2016/0073886 | A1 | 3/2016 | Connor |
| 2016/0081552 | A1 | 3/2016 | Wojtczuk et al. |
| 2016/0113526 | A1 | 4/2016 | Nageshwar et al. |
| 2016/0232811 | A9 | 8/2016 | Connor et al. |
| 2016/0287110 | A1 | 10/2016 | Morris et al. |
| 2016/0378069 | A1 | 12/2016 | Rothkopf |
| 2017/0119287 | A1 | 5/2017 | Flitsch et al. |
| 2017/0156676 | A1 | 6/2017 | Ferber et al. |
| 2017/0164878 | A1 | 6/2017 | Connor |
| 2017/0188864 | A1 | 7/2017 | Drury |
| 2017/0215793 | A1 | 8/2017 | Newberry |
| 2018/0146870 | A1 | 5/2018 | Shemesh et al. |
| 2018/0242860 | A1 | 8/2018 | LeBoeuf et al. |
| 2018/0353137 | A1 | 12/2018 | Balajadia et al. |
| 2019/0024696 | A1 | 1/2019 | Friedrich et al. |
| 2019/0030230 | A1 | 1/2019 | Connor |
| 2019/0110751 | A1 | 4/2019 | Lee et al. |
| 2019/0246963 | A1 | 8/2019 | Chung et al. |
| 2019/0283247 | A1 | 9/2019 | Chang et al. |
| 2019/0385708 | A1 | 12/2019 | Hong et al. |
| 2020/0075812 | A1 | 3/2020 | Konstantatos et al. |
| 2020/0376198 | A1 | 12/2020 | Newberry et al. |
| 2021/0145334 | A1 | 5/2021 | Ferber et al. |
| 2021/0169345 | A1 | 6/2021 | Wasson et al. |
| 2021/0169417 | A1 | 6/2021 | Burton |
| 2021/0212606 | A1 | 7/2021 | Tran |
| 2021/0293616 | A1 | 9/2021 | Capella et al. |
| 2021/0321942 | A1 | 10/2021 | Pushpala et al. |
| 2021/0330207 | A1 | 10/2021 | Richards et al. |
| 2021/0379388 | A1 | 12/2021 | Connor |
| 2022/0028553 | A1 | 1/2022 | Matichuk et al. |
| 2022/0233102 | A1 | 7/2022 | Shelton, IV et al. |
| 2022/0233119 | A1 | 7/2022 | Shelton, IV et al. |
| 2022/0233135 | A1 | 7/2022 | Shelton, IV et al. |
| 2022/0233136 | A1 | 7/2022 | Shelton, IV et al. |
| 2022/0233151 | A1 | 7/2022 | Shelton, IV et al. |
| 2022/0233191 | A1 | 7/2022 | Shelton, IV et al. |
| 2022/0233214 | A1 | 7/2022 | Shelton, IV et al. |
| 2022/0233241 | A1 | 7/2022 | Shelton, IV et al. |
| 2022/0233252 | A1 | 7/2022 | Shelton, IV et al. |
| 2022/0233253 | A1 | 7/2022 | Shelton, VI et al. |
| 2022/0233254 | A1 | 7/2022 | Shelton, IV et al. |
| 2022/0233267 | A1 | 7/2022 | Shelton, IV et al. |
| 2022/0238197 | A1 | 7/2022 | Shelton, IV et al. |
| 2022/0238216 | A1 | 7/2022 | Shelton, IV et al. |
| 2022/0238235 | A1 | 7/2022 | Shelton, IV et al. |
| 2022/0240869 | A1 | 8/2022 | Shelton, IV et al. |
| 2022/0241028 | A1 | 8/2022 | Shelton, IV et al. |
| 2022/0241474 | A1 | 8/2022 | Shelton, IV et al. |
| 2022/0415476 | A1 | 12/2022 | Connor |
| 2023/0103445 | A1 | 4/2023 | Lee et al. |
| 2023/0284905 | A1 | 9/2023 | Matichuk et al. |
| 2023/0355145 | A1 | 11/2023 | Matichuk et al. |
| 2023/0400327 | A1 | 12/2023 | Streem et al. |
| 2025/0049324 | A1 | 2/2025 | Matichuk et al. |

FOREIGN PATENT DOCUMENTS

| | | | |
|---|---|---|---|
| CN | 108451513 | A | 8/2018 |
| CN | 110167430 | A | 8/2019 |
| EP | 3387989 | A1 | 10/2018 |
| EP | 4486206 | A2 | 1/2025 |
| IN | 201941006594 | A | 11/2020 |
| KR | 102062646 | B1 | 1/2020 |
| KR | 20220112327 | A | 8/2022 |
| WO | 2020160058 | A1 | 8/2020 |
| WO | 2022231132 | A1 | 11/2022 |
| WO | 2023014653 | A1 | 2/2023 |
| WO | 2023187686 | A1 | 10/2023 |
| WO | 2023220082 | A1 | 11/2023 |
| WO | 2024173947 | A1 | 8/2024 |

* cited by examiner

HEALTH SENSOR USING MULTIPLE LIGHT EMITTING DIODES

CROSS REFERENCE TO RELATED APPLICATIONS

The present claims priority from U.S. Provisional Patent Application No. 63/446,613, filed Feb. 17, 2023, entitled "Health Sensor Using Multiple Light Emitting Diodes," the disclosure of which is incorporated herein by reference in its entirety.

BACKGROUND OF THE DISCLOSURE

Provided herein is a wearable health technology for continuous biomolecule sensing and monitoring for the prevention and/or treatment of Pre-Diabetes and Diabetes. The technology presented herein is important because chronic health issues and diseases are on the rise worldwide. Current estimates are that close to 9% of the world population is affected by diabetes, which is expected to rise to 10% by 2045. In addition to full diabetes, an estimated 352.1 million people worldwide are pre-diabetic, a figure which is expected to rise significantly in the coming years. In the case of diabetes, high Blood Glucose (BG) levels (e.g. hyperglycemia) are toxic and cause serious health complications due to damage to the vessels that supply blood to vital organs. Hyperglycemia increases the risk of heart disease and stroke, kidney disease, vision problems, and nerve problems. Further, conditions like diabetes can be a contributor to many other diseases and/or conditions such as cardiovascular disease, nerve damage (neuropathy), problems with nausea, vomiting, diarrhea, constipation, erectile dysfunction, kidney damage (nephropathy), eye damage (retinopathy), potentially leading to blindness, cataracts, glaucoma, foot damage leading to toe, foot or leg amputation, skin conditions including bacterial and fungal infections, hearing impairment, Alzheimer's disease, and depression.

Diabetes is a chronic metabolic disease characterized by elevated blood glucose levels. Chronic diabetes is classified as either type 1 (T1D), which is characterized by insufficient production of insulin and constitutes about 10% of diabetes cases, or type 2 (T2D), which is characterized by the body's ineffectual use of insulin and constitutes about 90% of diabetes cases. According to the CDC's 2020 National Diabetes Statistics Report, approximately 34.2 million individuals in the US, or 10.5% of the US population, have been diagnosed with diabetes. Typically, diabetes management is a balancing act of: routine blood glucose testing, strict monitoring of diet and physical activity, and, for most T2D patients, oral and injected non-insulin treatments. As indicated above, if blood glucose levels are too high, repeat episodes of hyperglycemia may lead to heart disease, stroke, kidney disease, blindness, and nerve damage.

A key contributor to the remarkably high risks of morbidity and mortality associated with diabetes is poor glycemic control. Glycemic control is assessed by measuring a patient's glycated hemoglobin, or $H_bA_{1C}$, as an indication of their average blood glucose levels over the past 2 to 3 months. Unfortunately, more than 50% of T2D patients fail to achieve target blood glucose levels, which is defined as an $H_bA_{1C}$ less than 7.0%. In recent years, the management of diabetes, and more specifically, glycemic control, has been aided with the advent of new technologies for assessing glycemia, such as continuous glucose monitoring (CGMs). In this regard, it has been determined that a patient's time in range (TIR), which can be presented as "% of glucose readings" or "hours per day" that the patient's glucose is within the ideal range, e.g., 70-180 mg/dL, has emerged as an important metric of glycemic control, and if a user can increase their TIR, they can increase the longevity of their wellbeing. However, glycemia and/or diabetes monitoring is an important facet of health management, but blood glucose monitoring is only effective if it is done regularly.

Particularly, regular blood glucose monitoring is an essential task in managing diabetes. And, likewise, those suffering from diabetes are more likely to manage their condition if their blood glucose measurements are shared with health professionals, and therefore, the sharing of the burden of monitoring is key. This is particularly so with respect to Type-2 diabetes. For example, Type 2 diabetes can be treated with diet, exercise, rest, and healthy eating that avoids high glycemic foods, but to date, there has been limited success for systems that allow for self-monitoring, and/or provide a platform by which health care professionals can participate in this management.

The most common and widespread method of glucose monitoring is self-monitoring of blood glucose (SMBG). SMBG involves intermittently obtaining a capillary blood sample from a fingertip puncture and electrochemically analyzing the sample with a glucometer. Frequent self-monitoring of blood glucose levels is an important activity in treating diabetes allowing a person to modify their diet and exercise regimen to ensure that normal blood glucose levels are maintained. SMBG has been shown to improve glycemic control and empowerment of people with diabetes. However, performing SMBG is a burdensome task to perform alone.

Two conventional methods for monitoring blood glucose levels include lancing the skin to obtain blood, or employing subcutaneous needle device that can semi-continuously read glucose levels. The lancet method is burdensome and expensive requiring the painful piercing of the skin in order to obtain a blood sample, which sample may then be contacted to an electrochemical test strip by which a blood glucose measurement may be taken. Unfortunately, monitoring with conventional electrochemical-based test strips is expensive, today typically costing $1.00 for each test and requiring the user to lance their finger to obtain a drop of blood for the test.

Accordingly, despite the many benefits of regular glucose monitoring, SMBG has several limitations. The finger pricking required to obtain SMBG samples is associated with pain and discomfort, which negatively impacts patient compliance. Additionally, SMBG is non-continuous. Particularly, people with diabetes typically perform SMBG at 3-5 set time points during the day (e.g., fasting, pre-prandial, postprandial) or when they experience symptoms of dysglycemia. Nevertheless, even if SMBG is performed frequently, it is recognized that clinically significant fluctuations in blood glucose may be missed due to the periodic sampling, and because of this an accurate TIR is often difficult to determine.

As, indicated, an alternative to SMBG for glucose monitoring is the use of a Continuous Glucose Monitoring (CGM) system. For instance, in alternative instances, instead of using a lancing methodology, a subcutaneous monitoring device can be used to determine and/or monitor glucose methods. Newly emerging continuous glucose monitors employ a device containing electronics and having a small-short, analyte-containing needle that penetrates the surface of the skin. These devices are not securely attachable to the body, are uncomfortable because of the sub-cutaneous, needle-like structure, and can frequently come off and/or can be easily separated from the user. Further, such devices typically need to be removed prior to bathing or swimming. Further still, they are very expensive, typically costing $10/day or more to use.

However, as explained below, although the subcutaneous method may be relatively painless, it is expensive and inconvenient. Specifically, CGM utilizes a circular substrate to which an adhesive is added so as to attach the device to the skin of the body. It often requires a subcutaneous needle or other type of analyte containing component that needs to be inserted into the skin. To date, most CGM systems detect glucose levels in dermal interstitial fluid through a glucose oxidase-impregnated electrochemical needle/sensor that is subcutaneously placed by the user. In contrast to the static measurement provided by SMBG, CGMs provide patients and healthcare providers with both nearly real-time glucose level snapshots and glycemic trends by the measuring interstitial fluid glucose concentration every 1-15 minutes, depending on the system. As a result, CGM shows improved glycemic control and increased patient satisfaction with use in people with diabetes, but it also has several drawbacks.

Particularly, even though lancing the skin is not required when using a CGM device, this newly emerging system still employs a small-short needle that needs to penetrate the surface of the skin. Hence, such devices for the subcutaneous electrochemical monitoring of interstitial fluid can also be invasive and create discomfort both of which have hindered the adoption and continued use of CGMs in people with diabetes. Further, these devices can frequently come off or separate from the user, and cannot be used bathing or swimming. Additionally, they are even more expensive than test-strip monitoring, typically costing $10/day or more. Although non-invasive devices and methods for analyzing various physical signals representative of user health, like blood glucose signal levels, have been extensively studied, there have been few breakthroughs made and brought to commercial viability.

SUMMARY OF THE DISCLOSURE

In view of the forgoing, what is needed, therefore, is a wearable sensing and/or monitoring device, and its associated systems and sub-systems, which are configured for non-invasively sensing, monitoring, and analyzing the health of a wearer of the device. In particular embodiments, the disclosed wearable sensing and/or monitoring device may be configured for detecting a change in the body, such as due to a change in the presence of one or more biological markers and/or physical variables within the body tissues. Particularly, this document describes devices, systems, and their methods of use to test and monitor biomolecule, e.g., glucose, levels using electromagnetic radiation, to overcome the aforementioned problems in other prior solutions to invasive, semi-regular, blood glucose monitoring and management.

Further, this document describes devices, systems, and their methods of use for testing and determining an effect that various different molecules, such as metabolites, have on the tissues of the body. Specifically, the systems, devices, and their methods of use described herein may be employed for determining the effects of biomolecules with regard to provoking the potential for a diseased condition within the body. In one embodiment, for example, the biomolecule of interest may be glucose, and the diseased condition to be determined may be the potential for hyperglycemia, diabetes, or pre-diabetes.

More particularly, the devices and systems disclosed herein are particularly important because of the high expense to health and living caused by such diseases as diabetes. For instance, recent data published by Insurance Providers and 3rd Party Payors, such as Medicare, indicate that about 37M people in the US suffer from Type 1 and 2 Diabetes, and an additional 96 M people have been estimated as suffering from Pre-Diabetes. In fact, it has been determined that 3rd Party Payors end up having to pay upwards of $1,800-$3,000 or more annually for glucose monitoring devices, such as invasive finger-prick monitoring devices, which many end up not using because of their invasive nature. Nevertheless, these 3rd Party Payors still cover such expensive testing and monitoring devices because when they are used, they reduce healthcare costs in the long run over drug treatments for those suffering from Diabetes, which can range from $4,000 to $10,000. This expense, which may require hospitalizations, increases manifold as diabetes progresses.

In light of the health benefits inured by performing continuous glucose monitoring, and in response to the high cost and limitations seen with the invasive nature of the self-monitoring of blood glucose (SMBG) and current Semi-Continuous Glucose Monitoring (CGM) systems, the inventors have developed the present Non-Invasive, Continuous, Glucose Monitoring System (NICGMS) to detect glucose levels in a non-invasive manner, such as without the use of needles, lancets, or other invasive technologies. Rather, this document describes a device, system, and a method to test interstitial and/or blood glucose values, e.g., levels and concentration, using electromagnetic radiation and optics, to overcome the problems in other previous solutions to invasive blood glucose monitoring and management. Specifically, in one set of configurations, a non-invasive method for performing continuous glucose monitoring by using an energy, radio frequency (RF), or microwave, source and a detection device, such as an optical detection device or antenna array, is presented. In this regard, energy from the energy generating source is directed into one or more layers of the skin, and reflected and/or refracted energy is returned to the detection device, whereby based on the reflected and/or refracted energy collected, the presence and effect of glucose on the body may be determined.

An advantage to employing such optical and long-waveform detection techniques is that they may be performed in a manner that is highly accurate, painless, safe, and noninvasive, whereby biological elements, such as metabolites, e.g., glucose, may be detected, measured, and monitored, such as within the blood, skin, and/or interstitial tissue. As indicated, in particular embodiments, the detection techniques may be optical, but in specific embodiments, the detection techniques may employ radio and/or microwave frequency emission. In either instance, such detection may be made by sensing and/or measuring the biomolecule itself, or by measuring its effects on the structures and fluids surrounding that element, such as by detecting and determining their reflective waveforms. Particularly, in some embodiments, provided herein is an apparatus and device that may be configured to employ non-invasive mechanisms, and techniques pursuant thereto, so as to determine levels, concentrations, movements thereof, as well as the effects, of biological agents, such as glucose, in and around the tissues of the body.

Consequently, in particular implementations, the device may be adapted to employ energy, such as light energy, radio frequency and/or microwave energy, for detecting the presence and effects of biomolecules within and around the tissues of the body. In particular implementations, the detection techniques may be optical, such as where an emitter, e.g., photoemitter, is employed for directing photons, a laser, or light into the tissues of the body. For instance, in various embodiments, the emitter may be configured as a photoemitter for directing electromagnetic radiation, such as in the visible, near infrared, and/or infrared spectrum, into the tissues of the body. However, in other embodiments, the emitter may be an antenna array that is configured for directing radio or microwaves into the body. Likewise, a receiver for receiving and detecting electromagnetic radiation reflected back from the tissues of the body may also be provided, such as where the receiver is a photodiode and/or corresponding antenna array attuned for receiving reflected radio and/or microwaves. In such instances, diffuse reflectance spectrum analysis may be used to determine the presence and/or level of a biomolecule, e.g., a glucose, in a subject's blood, tissue, and/or spaces therebetween. Detection of the molecule and its effects may be optical and/or long waveform based because of the change on wavelength and frequency of the return energy, and/or based on the change in the bodily tissues due to the presence of the biomolecule, as observed.

Accordingly, in some aspects, as described below, a non-invasive, continuous biomolecule detecting and measuring device is provided. For example, in various embodiments, the sensing and/or monitoring devices set forth herein are configured for determining a health condition based on the detection of various biological agents, such as within the blood, skin, organs, and the spaces therebetween, e.g., within the interstitial fluid. In particular embodiments, the wearable device and system may include technology to track various biometrics of the user with respect to one or more determined conditions, such as heart rate, heart rate variability, blood pressure, oxygen saturation, respiration rate, sleep levels, activity levels, and the like. Dependent on the configuration, the wearable system can include a device and apparatus together which can be worn on the wearer's wrist, arm, back, abdomen, leg, and the like, or can be carried on a wearer's person, worn on a chain or strap, or attached to some other part of the wearer's body, such as via an associated patch or bandlike apparatus.

In certain of such embodiments, the collected reflected and/or refracted energy data may be transmitted to a computer system, whereby energy diffuse reflectance spectrum analysis may be performed so as to detect and/or otherwise determine the level and effects of the biomolecule on the health of the individual. In particular implementations, such determinations may be performed by an analytics, e.g., artificial intelligence, module of the system. For example, in a particular implementation, the referenced artificial intelligence module may be embodied in a multi-layer artificial neural network so as to more directly read, determine, and/or predict bioagents, e.g., glucose, levels from the skin, blood, interstitial fluid, and/or other biological tissues, as well as to determine their effects on the body.

In various instances, the detection may be of the biological agents themselves and their presence, or a change in their concentration, which can demarcate a change in a determinable biological condition. In other instances, the detection may be of a change in the surrounding tissues and/or fluids of the body, due to the presence of the biological markers, in the tissues. The detection may be non-invasive, such as by being based on a detection of a change in a reflection and/or refraction pattern of light and/or radio waves being directed into the tissues. In such an instance, therefore, the sensing and/or monitoring device may include an electromagnetic radiation, e.g., light or RF, emitter and a corresponding electromagnetic radiation receiver. In certain embodiments, the emitter, therefore, may be configured for emitting energy, such as electromagnetic waves, including ultraviolet, visible, and/or infrared light waves, into the skin, and the detector will therefore be capable of receiving the various reflected waveforms back. In other embodiments, the emitter may be a radio frequency (RF) emitter, such as associated with a suitably configured antenna or antenna, and the receiver may be configured for detecting and sensing reflected radio or micro waves.

In any of these instances, information collected from the wearable system can be provided to the individual, may be stored on a server, and/or may be shared with other health professionals. This is an important feature of a holistic system for monitoring and tracking biomolecule levels and their effects on the body over time, because, as indicated above, a wearer of the device is more likely to keep track of their important health, e.g., glucose, levels when they know that other's will be viewing and/or monitoring and/or tracking them. For this reason, a feature of the present system is a series of communication modules for transmitting information, e.g., real-time, to one or more users of the system. Along with collecting sensed information, users can also track other health journal information relating to food consumption, activities or other observances relating to a person's health. The information supplied by the wearable system, in combination with user-supplied information, can provide a more complete understanding of a person's health state, and which can be analyzed by the wearer or health professional to make health condition assessments and predictions.

For instance, once the sensed data has been collected, it can be transmitted to an associated analytic system, which may then take the collected data, analyze it, and based on a difference in the light and/or radio wave reflectance, as well as the tissue's response thereto, a determination of one or more biomolecule values, as well as the body's response thereto, may be determined. Particularly, in various embodiments, based on changes to the blood flow, temperature, skin resistivity, and/or changes in particular biological responses, a given biological factor can be determined to be present in the blood, tissues, and/or interstitial spaces. Likewise, based on the presence and/or concentration of that biological factor, as well as based on the one or more biological conditions caused by the presence of that factor within the tissues and/or fluids of the body, one or more other conditions or other dynamics may be predicted. For example, in particular embodiments, based on the presence and level of glucose within the blood and/or interstitial fluids, a hyperglycemic condition can be detected, and based on this condition, one or more risks of diabetes or pre-diabetes may be calculated and/or predicted by the analytics system.

Accordingly, in one particular embodiment, as described in greater detail herein below, the sensing and/or monitoring device may be configured as a glucose monitor, such as including a light emitter having one or more light emitting diode arrays that are configured for emitting light in one or more wavelengths, such as from visible to near infrared to infrared. A light receiver may also be included such as where the light receiver may be a photodiode that is configured for receiving and detecting reflected light of corresponding frequencies to that emitted.

More particularly, the sensing and/or monitoring device may be configured for detecting the presence of glucose in the blood, tissues, and interstitial spaces, and then detecting a change of the reflectance of the emitted light due to a change in the respective structures and spaces of the tissues due to the presence of glucose. In this regard, a non-invasive glucose monitor, as herein described, is very useful because those who wear continuous glucose monitoring devices become more health conscious, lose weight, and get healthier, thereby reducing the incidence and/or severity of diabetes, other healthcare conditions, thus, lowering healthcare costs. In a specific implementation, the presented non-invasive continuous biological agent monitoring device may be configured as a wearable device, such as a wearable patch-like device, that can be worn, e.g., continuously, for a prolonged period of time, so as to monitor the levels of one or more biological markers and for monitoring the biological marker non-invasively, e.g., without penetrating the skin or causing any other harm to the wearing subject.

Particularly, in one particular aspect, provided herein is an apparatus for detecting a condition of a living body. For instance, the apparatus may include a sensor and/or monitoring unit, which unit may include an emitter and a receiving, e.g., an optics, component, such as including a light emitting array and a photoreactive receiver, such as photodiode, both of which may be fully or partially encased within a housing. The housing may be formed of any suitable material, and may be defined by a plurality of opposed bounding members or walls, along with a pair of opposed top and bottom surfaces.

Specifically, in various embodiments, a plurality, e.g., two, pairs of opposed walls may form side barriers that are offset from one another so as to define a cavity therebetween, such that the emitters, receiver, and other electronic components of the apparatus may be encased. In particular embodiments, a further set of opposed surfaces may form a top and a bottom surface, so as to fully enclose the entire or a portion of the cavity. In such an instance, one or more of the walls may be electromagnetically transmissive or include an opining such that electromagnetic waves, e.g., light waves, emitted from the light source may pass through or out of the housing and into a tissue, e.g., skin, surface upon which the monitoring apparatus is positioned.

In alternative embodiments, the housing may be composed of a plurality of bounding surfaces, such as a top surface and a bottom surface, that are configured for being coupled together in a manner so as to form the cavity. In such an instance, the bottom surface, or a portion thereof, may include an opening and/or transmissive member, which is configured for allowing the passage of emitted and/or reflected energy out of and back into the housing. For example, in certain embodiments, one or more portions of the top and/or bottom surfaces may include a window therein, through which window electronics retained within the cavity of the device may be viewed and/or through which window a light, such as an infrared, visible, and/or an ultraviolet (UV) light, or other focused energy, may be passed. In particular instances, the window may be coated with an anti-reflective coating layer.

Specifically, in a particular iteration, the window may include a transmissive member, e.g., glass, that is coated to allow light of certain wave length, such as infrared light, to pass therethrough, while blocking light of another wavelength, such as visible and/or UV light. In particular embodiments, the glass or other transmissive member may be coated with an anti-reflective coating. Further, in certain instances, one of the surfaces of the housing may be configured to attach to the living body's skin so that the window abuts the skin's surface, or to attach to another member, such as a support or attachment member, which attachment member may serve the purpose of holding the position of the sensing and monitoring device in close proximity to the skin of a body part of a wearer of the device.

In certain instances, the electronics retained within the sensor device housing may include one or more, e.g., a plurality of optical units, which may be formed into one or more arrays. For instance, in various embodiments, one or more arrays of light emitters and light receivers, such as light emitting diodes (LEDs) and photodiode(s), may be included. The arrays of LEDs and photodiodes may be arranged in the housing so as to be positioned proximate the transmissive portion of the bottom surface of the device. The arrangement of the light emitting. receiving arrays with respect to the transmissive portion of the bottom surface should be such that it allowing the various light emitting and receiving components of the device to have electromagnetic access to the skin. In various embodiments, the bottom surface of the housing may be configured so as to allow the interior components, e.g., light generating and/or receiving elements, to illuminate the living body's skin below the bottom surface as well as to receive reflected light back therethrough. In one embodiment, the bottom surface may include an opening having a window through which the light elements may direct and pass the light waves they generate.

Further still, with respect to the light emitting and receiving array within the housing, each array may include a number of light emitters and light receivers, so as to form a light sensor. In particular instances, each light sensor may be configured to emit light of a plurality of wavelengths, and therefore, may be configured to sense light, such as light reflected back from at least one of the light emitters. In certain instances, sensor may be configured for emitting and receiving, e.g., sensing, light from a variety of different emitters, e.g., LEDs, such as where each LED emits light of the same or different wavelengths, e.g., where each LED emits light of a different wavelength. In various embodiments, one or more of the window or the sensor may include a filter that is configured to only allow the passage of light within a narrow bandwidth to be emitted and/or received, such as to be able to specifically sense biometric data signals. Specifically, a plurality of filters, e.g., bandwidth filters, may be included and be associated with a plurality of the sensors, where each filter may be configured to allow passage of only specific bandwidths of light being emitted and/or returned from the living body, such as where each filter may prohibit light of the same or different wavelengths as the other filters. In a particular embodiment, the filter may be composed of or otherwise include an anti-reflective coating.

Additionally, a battery may also be included within the housing so as to provide electrical power to the sensors and other device electronic components of the sensing and monitoring device. In various embodiments, the battery may be rechargeable, such as a wireless charging battery. In particular embodiments, the battery may be a rechargeable lithium-ion battery.

Accordingly, in view of the above, in one aspect, provided herein is a wearable system that may be configured for monitoring the health of a wearer, and in particular, determining a level or concentration of a biological agent in the tissues of the body. For instance, in certain embodiments, the wearable system herein is configured so as to detect, monitor, track, and/or predict a type or level of bio-reactive agent within the tissues, vessels, fluids, and/or spaces of the body. Particularly, in one embodiment, the sensor may be configured as a glucose monitor, where the monitor is configured for determining glucose levels in the blood, tissues, and/or interstitial spaces of the body of the wearer.

In accordance with the above, the wearable system herein disclosed may include technology to track various biomolecules that affect particular biometrics of the body of the wearer, such as heart rate, heart rate variability, blood pressure, oxygen saturation, respiration rate, sleep levels, activity levels, and the like. In particular embodiments, the devices and systems of the disclosure may be configured to sense, monitor, and/or track various biometrics directly in a manner that is non-invasive. Particularly, it has been discovered that optical, radio frequency, and/or spectral techniques may be employed to determine biomolecule values within and between the tissues and vessels of the body, such as in the interstitial spaces. For example, such optical and RF techniques may include: optical coherence tomography, microwave spectroscopy, near-infrared spectroscopy (NIRS), midinfrared spectroscopy (MIRS), Raman spectroscopy and visible laser light. Specifically, the wearable devices and apparatuses disclosed herein can be configured to perform one or more of the following techniques, consistent with the present disclosure: polarimetry, photoacoustic spectroscopy, bio-electrical impedance spectroscopy, thermal emission, optics, and other such technologies.

In various instances, visible, infrared, and/or near infrared, or even RF spectroscopy may be advantageously employed to receive and analyze reflected and/or refracted energy so as to determine biomolecule values and their effects on the body in a non-invasive manner. These methods, as disclosed herein, may be performed in a simple but effective manner, as compared to prior detection methods, such as by using optical, e.g., NIR, components that can be used collectively to penetrate the skin to adequate depths to enable accurate analysis. These reflected and/or refracted light signals, once obtained, may be processed, or preprocessed, and can then be transmitted to a distributed computing system, such as including a mobile smart device running a suitably configured software application of the system, where a pre-trained artificial neural net (ANN) may then determine the estimated biomolecule, e.g., glucose, values. The software application can then instruct the displaying of the biomolecule, e.g., glucose, values and levels, such as on a display of the mobile device, for the user to view and use to track their health trends.

As discussed herein below, in particular embodiments, the sensing and/or monitoring device may be configured as a disc-like element that is configured for being fit within an attachment structure by which the sensor may be firmly applied to the body, and once applied prevented from moving, either laterally or rotationally. The attachment structure may include, or otherwise be associated with, an adhesive so as to form a patch member, such as for removably, but persistently, positioning the sensing and/or monitoring disc-like device proximate the skin of the wearer. However, in other implementations, the wearable system may include a device that can be worn on the wearer's wrist, carried on a wearer's person, be worn on a chain or strap, or may be attached to some part of the wearer's body, such as via an adhesive framework member.

In use, the sensing and/or monitoring device and system may be configured for detecting the presence of a molecule, such as glucose, its level, its concentration, and may further track its changes over time. In performing such tasks, the device and system collects a number of readings over time, which readings may be used by the system to determine one or more trends, which trends can then be used to determine one or more conditions and/or the progression thereof, such as based on the readings taken by the device. In such an instance, the interpretation of results can be made with respect to determining one or more levels of a biomolecule, such as glucose, over a determined period of time, where sequential readings are collected and analyzed, and resulting data, e.g., over a large sample set, is used to give notices, warnings, or make health care suggestions to change one or more parameters affecting the health of the wearer of the sensing and monitoring device.

In various embodiments, the information collected from the wearable system may be provided to the individual via a smart application, such as being run a mobile computing device of the user, may be stored in a database associated with a server of the system, and/or may be shared, via a corresponding mobile or desktop interface with the user's doctors, or other concerned parties. Along with such light and/or other sensed information, users can track their health information, track their progress towards health goals, such as relating to diet, daily activities, or other important factors relating to a person's health. Such information detected and/or supplied by the wearable system, in combination with user-supplied background, health record, characteristic, and/or goal information, can provide a more complete understanding of a person's baseline health state, and which can be analyzed by the wearer or health professional to make health condition assessments, set goals, and make predictions with respect thereto.

Consequently, in various embodiments, the apparatus may include, or otherwise be associated with, a computing system, which computing system may be an on- or off-board computing system. For instance, in certain instances, the computing system may include, or otherwise be associated with, a remote server, such as a cloud-based server. Particularly, in particular embodiments, the computing system may have an on-board computing system that includes one or more microprocessors, micro-controllers, a series of processing engines, and/or other processing elements, such as one or more integrated circuits, which in turn may include one or more dedicated processing engines or hard-wired circuits. These processing elements may be communicatively coupled with a circuit board and be powered by an associated power source. Hence, in certain embodiments, the computing system may include, or otherwise be configured as an integrated circuit that may be embodied as a FPGA or ASIC device that may be provided on the printed circuit board (PCB).

In certain iterations, one or more of the LEDs, photodiodes, and/or electronic filters may be mounted on the PCB. Additionally, the circuit board may further include, or otherwise be associated with, one or more batteries and/or a battery charging circuits. Further still, a controller, such as a microcontroller for controlling the emitters, e.g., LEDs, receivers or sensors, and/or digital or electronic filters, may also be included. In various embodiments, the on-board computing system may be coupled, e.g., via a wired or wireless communications network, to one or more remote server systems, such as where one or both the on-board and off-board computing systems may be configured to receive input data, such as energy wave data, to analyze the received data, and/or to predict a health metric of the wearer of the device, e.g., user, based on, or otherwise in association with the received data.

In particular embodiments, the computing system may include or otherwise be associated with an artificial intelligence (AI) module that may include a machine learning engine as well as an inference engine, such as where the AI module may be configured for using the reflected energy, other sensed data, and/or other biometric data so as to generate a predictive model by which one or more biomolecule, e.g., glucose, levels of the subject, e.g., over time, may be predicted and/or otherwise determined. In more particular embodiments, the AI module may be configured as, or otherwise include, a data structure, which data structure may be instantiated in an artificial neuro-network. For instance, in various embodiments, the AI module may be configured so as to implement one or more of a polynomial regression method, a neural network, a Bayesian network, a decision tree, a support vector machine, or the like. More particularly, in some embodiments, the apparatus can employ near infrared diffuse reflectance spectrum analysis, e.g., combined with a multi-layer artificial neural network, to directly read biomolecule, e.g., glucose, levels in or around the skin, vessels, and/or tissues of a wearer of the device. As set forth above, in particular implementations, a method for determining a level, quantity, concentration, or an effect of a biomolecule on the body is provided, such as where the technique performed in this pursuit is implemented in a manner that is non-invasive, inexpensive, and convenient.

In such implementations, the sensing and/or monitoring device may be formed into a wearable patch, watch, or bandlike apparatus that can be configured so as to continuously monitor biomolecule, e.g., glucose, levels without invasively penetrating the skin. Accordingly, the wearable system as described herein may be configured for collecting bio-information from the tissues of the body, whereby the information collected from the wearable system can be used to monitor, analyze, and/or predict health, disease progression, and potential health risks of the user, which may then notify or warn the user of such risks or be directly transmitted to a healthcare professional for action thereon. In particular implementations, the biomolecule levels may be correlated over time with other user activities, such as their reported energy and/or activity levels, at rest and/or at sleep, and at other periodic times during the day or night, so as to determine one or more relevant cycles of the individual. The system, therefore, can detect activity type and levels, can take measurements, and monitor biomolecule levels and other related metrics, and correspond them one with the other, which collectively can be used to perform analysis or may be stored in a database associated with a server of the system. In various instances, this server-based solution can collect all of this data and provide health advice and guidance, and, as indicated, can be used to share health information with a healthcare professional.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

This document describes devices, systems, and their methods of use for employing a novel wearable device to non-invasively test and monitor one or more physical attributes and/or health metrics of a wearer of the device and/or associated apparatuses. Particularly, a system and method employing a novel wearable device to non-invasively sense, test, and monitor one or more physical attributes of a wearer in relation to one or more sensed biomolecules is presented. In some implementations, the biomolecule being sensed and tested may be a metabolite, such as glucose, and the wearable device may be configured for testing and monitoring values, such as levels and/or concentrations, of the metabolite, in the tissues, vessels, and surrounding fluids of the body, for instance, using electromagnetic radiation, e.g., light or RF. These devices, systems, and their methods of use, such as employing light or RF energy to measure the presence and effects of glucose on the body tissues is painless, safe, and inexpensive, and thereby overcome the deficiencies in the aforementioned solutions that are more invasive and/or non continuous in their monitoring and management of glucose levels.

Figure 1:
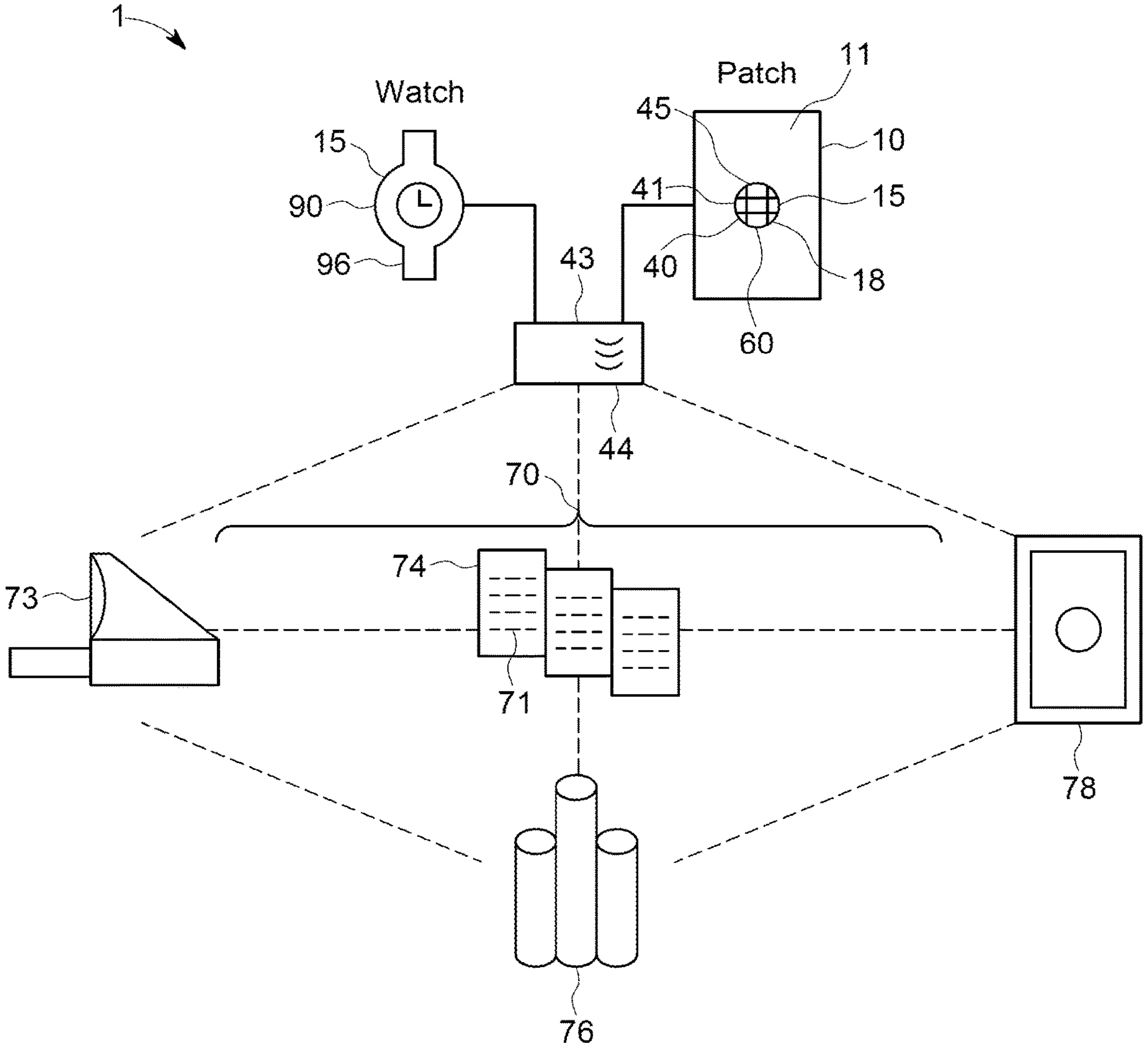
FIG. 1 illustrates a biometric sensing and monitoring system including a sensing and monitoring apparatus along with associated computing devices, servers, and databases in accordance with the teachings of the disclosure.
Figure 6A:
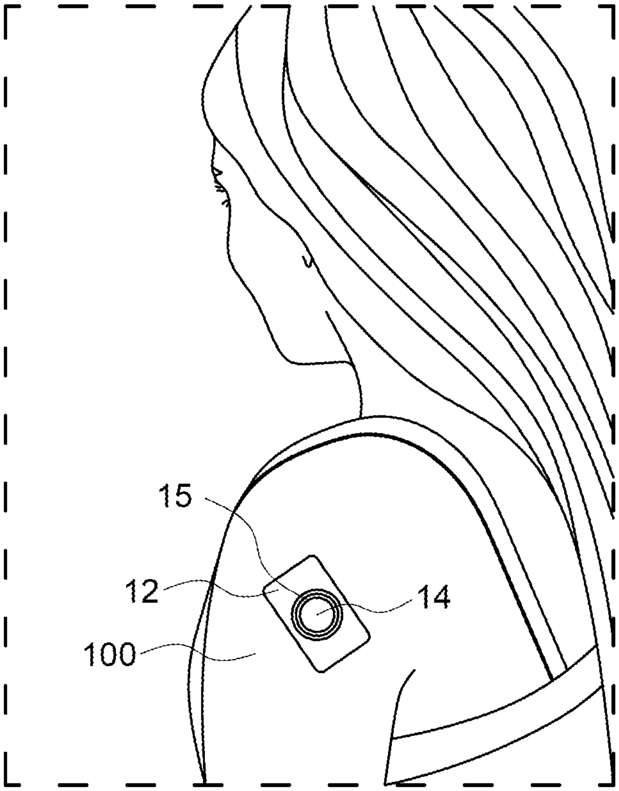
FIG. 6A illustrates the biometric sensing and monitoring device of FIG. 2B or 5A being worn by a user.
Figure 6B:
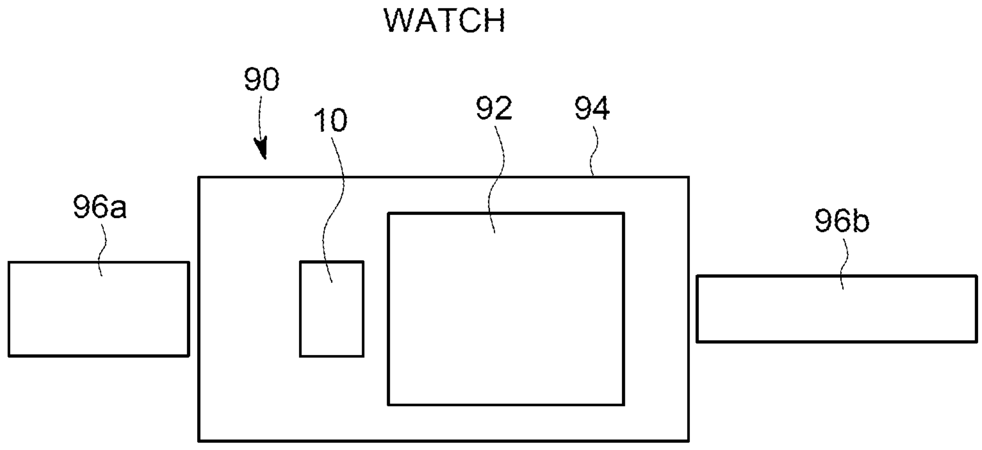
FIG. 6B illustrates the biometric sensing and monitoring device of FIG. 2B or 5A configured as a watch-like device for being worn around the wrist of the user.

As can be seen with respect to FIG. 1, a system 1 is herein provided for detecting and determining the presence of a biomolecule, such as glucose, in one or more biological tissues of the body and/or in the interstitial spaces there between. Generally, the system 1 may include one or more biometric sensing and/or monitoring devices 15 that may be associated with an attachment structure 12 so as to form a sensing and monitoring apparatus 10. In particular embodiments, the attachment structure may be configured as a patch 11, which patch may include an attachment element 13, such as an adhesive, by which the patch 11 may be adhered immovably to the body so as to be worn by the user 100 as depicted in FIG. 6A. In alternative embodiments, the biometric sensing and/or monitoring device 15 may be in the form of a watch-like device 90, and the attachment structure 12 may be configured as a band 96 to which the watch-like device 90 may be coupled so as to be worn around the wrist of a user, as depicted in FIG. 6B.

In either instance, the wearable biomolecule monitoring and tracking apparatus 10 may include a sensor device 15 having one or more sensor units 18. Each sensor unit 18 may include a number of sensor sub-systems, such as including: one or more energy emitter and/or receiver arrays 20, for sensing and generating biomolecule and/or biometric data, a communications module 43, including a transmitter 44*a* and receiver 44*b*, for transmitting the collected biomolecule and/or biometric data, as well as one or more of on- 45 and/or off-board 70 computing system, including an analytics system 71. Where the computing system 45 is on-board it may be configured for processing, e.g., pre-processing, collected sensed energy data, e.g., reflected spectral radiation data. For instance, the onboard computing system 45 may include an analog to digital converter 41 for converting raw sensed energy data, e.g., reflected electromagnetic radiation data, into digital signal read data, which can then be transmitted to an offboard computing system 70 such as for display and/or further processing thereby.

For instance, as described in greater detail herein below, the sensor unit 18 may include a sensor array 20 having a number of energy emitters 22 and energy receivers 23. The energy emitter(s) 22 may be configured for directing energy, such as electromagnetic radiation, e.g., light, into the tissue of a wearer of the apparatus 10. As such, some of the emitted electromagnetic radiation of various wavelengths may be absorbed by the skin tissues, and various components thereof, some will be refracted, and some will be reflected back. The energy receiver(s) 23, therefore, may be configured for collecting the raw, non-absorbed electromagnetic radiation, e.g., reflected radiation, which can then be converted, e.g., by an analog to digital converter 41, into digital signal read data. Consequently, the onboard computing system 45 may be configured for processing the electromagnetic and/or read data, converting it to processed read data, and then may further process the read data so as to determine one or more values of the biomolecule being assessed.

Once processed, the biometric sensing and monitoring device 15 may transmit the determined values, raw electromagnetic radiation, and/or digital signal read data, e.g., wirelessly, to an associated computing system 70 and/or to a mobile computing device 78 for subsequent processing and/or display thereby. In other instances, such as where more complex computational processing is desirable to be implemented, the sensing and monitoring device 15 may transmit the raw data, the digital signal read data, and/or processed value data to an external computing system 70, such as to a server system 74 and/or an associated client computing device 73, for additional processing of the data. Such transmission may be through a wired or wireless network connection. In particular implementations, such transmission may be performed via a suitably configured wireless communications protocol, such as WIFI, BLUETOOTH®, BLUETOOTH LOW ENERGY® (BLE), RFID®, ZIGBEE®, and the like.

Accordingly, in various implementations, a computing system 70 of the system 1, whether it be implemented as an on-board processing unit 45 of the sensor device, a remote, e.g., cloud-based, server 74, a client computing device 73, e.g., desktop computer, and/or mobile smart phone 78, may include or otherwise be associated with an analytics system 71. The analytics system 71 may be configured for detecting and/or quantifying one or more biomolecules within the tissues of the body, and with respect thereto, determining one or more characteristics of the biomolecule of interest, or characteristics of one or more states of the wearer of the sensing and monitoring apparatus 10, such as in response to the determined presence of the biomolecule. In such instances, the analytics system 71, may be embodied by one or more processing modules, which may include a number of processing elements that can be coupled together to form a processing engine. Particularly, in particular embodiments, the analytics system 71 may be associated with a processing module that includes a plurality of sets of processing engines.

Specifically, in one embodiment, the system 1 may include a processing module for receiving or otherwise accessing the raw or preprocessed sensed data, e.g., digital signal raw data, and processing that data so as to determine a characteristic of one or more sensed biomolecules in the body of a user and/or a characteristic of one or more states of that user, such as caused by, or experienced in conjunction with, the presence of that biomolecule. For example, the analytics module 71 may include a first and/or second set of processing engines that are configured for accessing raw and/or digital signal read data and for converting the digital signal data into spectral data. A third set of processing engines may then take the spectral data and determine thereby a presence and/or a value of one or more biomolecules within the tissue of the user, such as based on a spectral analysis of that data.

Further, sets of processing engines may then further analyze the resultant data so as to determine an effect of the body tissue, which may be based in part on the spectral data, as well as in part on other sensed and/or observed data, such as trend data, so as to produce suspected biomolecule effect result data. Additional sets of processing engines may then use one or more of the determined spectral data and the suspected biomolecule effect result data to build a data structure, such as a data structure including a number of different raw and/or read data obtained from a number of different reads derived from the user, or a plurality of users, over time so as to generate a model of past and/or predicted effect data based on the value of the one or more biomolecules, raw and read data, and spectral analyses related thereto. From these data, a further set of processing engines may then determine, or otherwise predict, a characteristic state of the user, such as based on the one or more trends or models, for instance, where the determined characteristic state data represents a state of the user based on the value of the one or more biomolecules.

In particular embodiments, the data to be collected by the sensing and/or monitoring device 15 may be collected in conjunction with one or more other biomolecule sensing device such as for more directly measuring and/or determining the values, e.g., levels and concentrations of the biomolecule of interest. For instance, a finger prick may be employed to lance the skin and draw blood, a blood sample ay be associated with an analyte stick, and then the analyte and blood may be inserted into an analyte, e.g., glucose monitor, where by an actual reading of the level and concentration of blood glucose may be determined. This biomolecule level and concentration data may then be transmitted into the computing system 70 or 78, such as wirelessly, or it may be entered manually by the user, such as by entering the information via the mobile application running on their associated smart phone. Other forms of biomolecule monitoring devices, such as the analyte-needle patch like devices described herein below, may also be used to test and input biomolecule levels into the system, such as in conjunction with the sensor devices and methods disclosed herein.

Hence, in various implementations, the wearable monitoring and/or tracking device 15 can test for the presence, concentration, level, and/or reactivity of a biomarker, such as glucose or other metabolite, in a tissue of the body, in a non-invasive manner, such as using electromagnetic radiation detection and/or spectral analysis. As described herein, the electromagnetic radiation often refers to light waves, but ay also refer to Radio Frequency (RF) or microwave waveforms as well. In the case of RF and/or microwaves for use in detecting and/or characterizing the presence of a biomolecule within a tissue, the emitter and/or receiver of the sensor unit 18 may be implemented in connection with a suitably configured antenna array, and the rate of emittance, e.g., bursts, may be short with low amplitude, so as to prevent damage to the underlying tissues.

In any of these instances, the wearable sensing and/or monitoring device 15 can be configured to emit energy into a living tissue of a body, such as at a low amplitude so as to not over energize the tissues, for the purpose of testing for biomarkers or metabolites in the wearer's blood, skin, and/or interstitial spaces therebetween. In doing so, a number of techniques can be employed so as to detect one or more of the presence, concentration, and/or effects of a biomolecule within the tissues of the body of a user 100, and the response to of those tissues to the presence of that biomolecule can also be determined. The analytical techniques that can be employed in a manner consistent with the present disclosure include, but are not limited to: polarimetry, photoacoustic spectroscopy, bio-electrical impedance spectroscopy, thermal emission, optics, acoustics, and other technologies. Such optical and acoustic techniques can be employed herein in a highly accurate, painless, and safe noninvasive detection and measurement process. Relevant determination methods that may be employed by the analytics system 71 may include optical coherence tomography, microwave spectroscopy, near-infrared spectroscopy (NIRS), midinfrared spectroscopy (MIRS), Raman spectroscopy, and/or visible laser light spectroscopy. In various embodiments, Green, Red, Infrared, and/or Near Infrared spectroscopy may be advantageously employed for their simplicity and effectiveness relative to other techniques. Another advantage is that Visible, IR, and NIR components are reasonably priced and can penetrate the skin to adequate depths to enable accurate analysis.

Accordingly, in view of the above, the devices, systems, and their methods of using electromagnetic radiation, as described herein, for detecting and testing for biomolecules within the skin, are both painless and effective for continuous use over a prolonged period of time, thereby overcoming the limitations of other potential invasive and non-invasive solutions. Specifically, electromagnetic waves, e.g., light, RF, etc., have characteristic levels of absorption and/or reflectance within the skin that may be dependent on the length and frequency of the underlying waveform, whether it be visible or non-visible light or a radio frequency. This phenomenon may, in part, be a basis for performing spectral analyses, as described herein. For example, exposing a tissue to specific wavelengths and detecting the absorption and/or reflection levels allows the analytics system to determine the presence of specific elements, and further analysis allows for the detection and/or prediction of the results, on the body, due to the presence of those specific elements, e.g., biomolecules, within the tissue.

Particularly, combinations of elements produce a combination of absorption and/or reflectance patterns that can be used to determine the presence of molecules based on their elemental composition and the various spectral patterns they produce. By comparing the characteristics of these patterns, and/or their light intensities, with the absorption response in the body tissues, it is possible to determine the presence and values of certain biomolecules within body tissues along with their levels and concentration. This computation, however, may include the simultaneous analysis of a number of different factors, from the same or a number of different individuals or groups, using a plurality of detection devices and methodologies, which may all need to be evaluated when performing an accurate determination and/or measurement. In various embodiments, a data structure by which all of these various datapoints may be compared and weighted may be built, such as in the performance of the referenced evaluations. Consequently, the analytics system may embody, or otherwise employ, an artificial intelligence module, by which to perform the various evaluations herein disclosed.

For example, in some implementations, a wearable sensing and/or monitoring device of the system may employ electromagnetic radiation emittance and sensing along with diffuse reflectance spectrum analysis together with an artificial intelligence system that can analyze a plethora of data of the individual, over time, as compared to a number of other such individuals, so as to develop and/or use one or more trends and models by which a given particular set of data may be evaluated. More specifically, raw waveform, read, spectral, and other data of the individual can be combined within a data structure, such as a multi-layer artificial neural network, to directly read and/or determine biomolecule, e.g., glucose, levels from, or within, the skin of an individual wearing the biometric apparatus. These techniques are advantageous over previously implemented devices and techniques because the apparatuses employed herein are non-invasive and relatively comfortable to wear, such that continuous readings may be made over time, and during exercise and showering, which has heretofore not been possible, making these calculations impossible for other such non-continuous sensing devices.

For instance, as indicated above, the present devices are advantageous over other solutions previously sought, because the measurements obtained by the present devices are performed in a non-invasive manner, such as without requiring needle pricks or finger sticks, which are typically used for detecting and/or taking blood glucose levels. Thus, the present devices and systems increase compliance and useability, while avoiding the drawbacks of previous sensing device implementations. Particularly, the manner by which biomarkers are presently detected by devices currently on the market suffer from major drawbacks in that they are painful, expensive, and inconvenient. Such finger-prick devices, by their nature, do not allow for continuous sensing and monitoring, and because of the pain involved, they evidence poor compliance. Accordingly, the analytics techniques disclosed herein could not be performed with such devices.

More particularly, presently available devices are painful to use in that they require an invasive pricking of the skin, so as to intermittently test blood retrieved thereby. Other iterations involve the intrusion of a needle-like appendage that must be inserted and remain within the skin. These devices are uncomfortable to wear, should be removed before showering, and, therefore, also evidence sub-optimal compliance. Another factor negatively effecting compliance is due to the fact that the use and maintenance of such devices are expensive, such as averaging about $120/mo. Hence, previous devices are expensive, inconvenient to use, last only one or two weeks, and cannot readily be removed and/or adjusted. Such devices often further suffer from largely being "dumb" devices with limited data collection, and have virtually no on-board analysis. Additionally, because these devices typically have sensors that need to be replaced every 7-14 days, some with a transmitter that also needs to be replaced every 3-4 months, their use creates a problem of increased waste of medical materials.

Specifically, there are two main types of invasive semi-continuous glucose sensing devices that are currently being promoted. One such type of device is the aforementioned glucose monitoring device that requires the invasive finger prick in order to test the blood for glucose. The other type of device includes a sensor unit that needs to be inserted within the skin of the user. In this regard, this device does not measure glucose levels directly like the finger-prick blood glucose monitoring device does. Rather, it utilizes an amperometric electrochemical signal that is generated when glucose, present in the interstitial fluid, reacts with an inserted chemical coated sensor, which reaction thereby converts the interstitial glucose to glucose oxidase that it then detects. In this regard, such amperometric sensor devices measure glucose in the interstitial fluid through an electrochemical reaction facilitated by a glucose-specific enzyme, i.e., glucose oxidase, which is coated onto the inserted glucose sensor, and reacts with glucose present in the space so as to convert it to glucose oxidase.

The herein disclosed non-invasive, continuous sensing devices operate on a completely different technological basis than the aforementioned amperometric sensor devices. With respect to the devices, systems, and their methods of use disclosed herein, in certain iterations, the present optical and/or acoustic based sensor arrays use electromagnetic, e.g., light or RF or microwave, absorbance and spectral analysis to determine bio-marker values, such as where the biomarkers are present and observable in the interstitial fluid and/or blood. As indicated, in various embodiments, the presence of the biomolecule may be detected and/or predicted directly via on-board analysis, e.g., of a spectral array, but in other embodiments, the presence of the biomolecules and their effects may be determined by a model generated by a suitably trained Artificial Intelligence (AI) module, such as by building and employing an Artificial Neural Network (ANN), as explained herein below.

More specifically, it has been determined herein that the presence of molecules, such as glucose, within the blood and interstitial fluids, may affect the absorbance and/or reflection of electromagnetic radiation, e.g., light, being directed at it, such as through the skin and tissues of the body. For instance, molecules, e.g., glucose, affect light absorbance and reflection in a uniform, and characteristic manner, such as by reflecting emitted light back at a characteristic wavelength and frequency. When glucose is in the blood and/or interstitial fluids, the skin color and/or composition changes, such as on an infrared wavelength scale, which can then be observable by the detecting and sensing devices of the disclosure.

For example, when lights of particular wavelengths are directed into the skin both in and not in the presence of a biomolecule of interest, the light reflected back changes in its characteristics, e.g., characteristic frequencies, based on whether the biomolecule is present or not, and further based on the reactance of the skin thereto. These characteristic frequencies can allow a sensing device of the disclosure to detect the presence of these molecules, as well as their quantity and/or concentration in the interstitial fluid and/or blood. Consequently, in various embodiments, if a light (or a laser or an RF emission, etc.) is directed into the skin, at a particular frequency and wavelength, a characteristic pattern of energy absorbance and/or energy reflectance may be sensed and obtained, such as by a specifically attuned electromagnetic radiation sensing device, e.g., energy receiver.

This pattern can then be used to determine the presence and quantity of given biomolecules, e.g., glucose, in the blood and/or interstitial fluid, as well as to predict the effect such a biomolecule will have on the body. For instance, the presence and quantity of glucose, or other biomolecules, may be determined by comparing a test light spectrum of a sample with a known light spectrum where the presence and quantity of biomolecules, e.g., glucose, is known, e.g., based on how well the test sample light absorbance and reflection pattern approximates the known light absorbance and reflection pattern where glucose is present. This process can be performed using a laser; however, such an implementation is difficult because currently available lasers are large, bulky, high energy absorbing equipment that is not readily transportable or mobile.

Consequently, miniaturized light sources, e.g., light emitting diodes, have been developed and it has been determined that, like lasers, these light sources, when directing light into the skin also produce such characteristic light absorbance and reflection wave forms. This was unexpected in that such light sources are not as intense, nor accurate, as using a laser, but are accurate enough to give relative readings that can be analyzed, in accordance with the methods disclosed herein. By performing the processes herein described, using low intensity light sources, such as generated from light emitting diodes, it has been found that accurate blood and interstitial biomolecule values and levels can be determined in a manner that will allow a subject to monitor and control the body's response to those biomolecules.

Pursuant to these findings, these miniaturized light sources have been formed herein into arrays, where each light sources may be configured to emit light of one or more particularized wavelengths, which light when directed into the skin can excite a reaction thereby. This reaction in turn creates a characteristic absorbance and reflection pattern of the light, which differs in the presence of various biomolecules, and thus, can be sensed by the accompanied light detection mechanisms, e.g., photodiodes, and used to determine one or more conditions or states of the body. This reflection pattern may be due in part to the interaction of light with the biomolecule and/or the reaction to the skin composition in response thereto. Collectively, as described herein, the light emitters and light sensors can be miniaturized and fit into a portable sensor unit that can be positioned on the skin so as to continuously, and non-invasively monitor biomolecule, e.g., glucose, levels, such as based on light absorbance and/or reflection patterns, regardless of how active the wearer is and/or what activities in which they engage, be it walking, running, or even swimming.

Figure 2A:
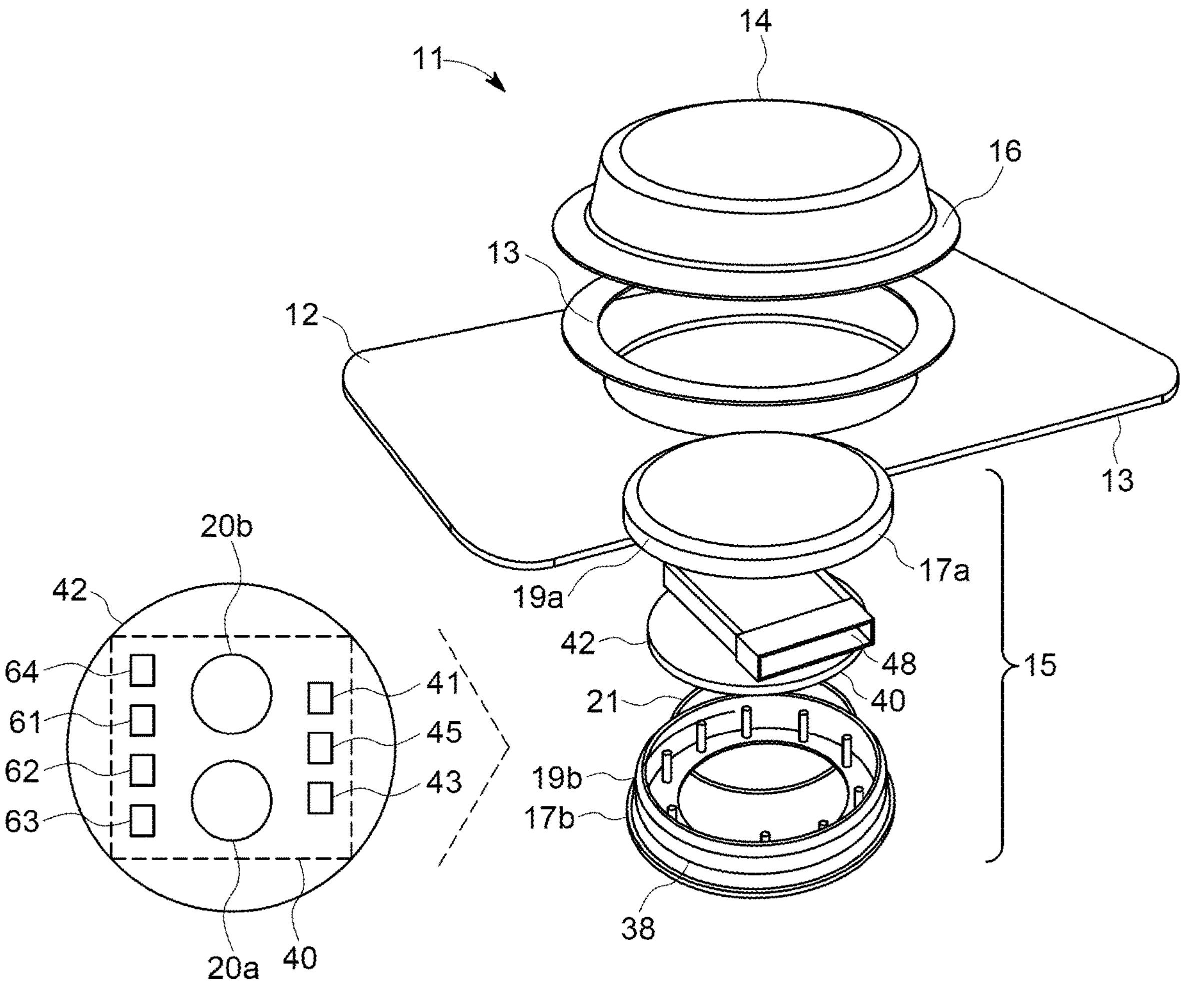
FIG. 2A presents an exploded view of a first embodiment of a biometric sensing and monitoring device for sensing the presence and a value of a biomolecule of interest, in a non-invasive and continuous manner, in accordance with the teachings of the specification.
Figure 2B:
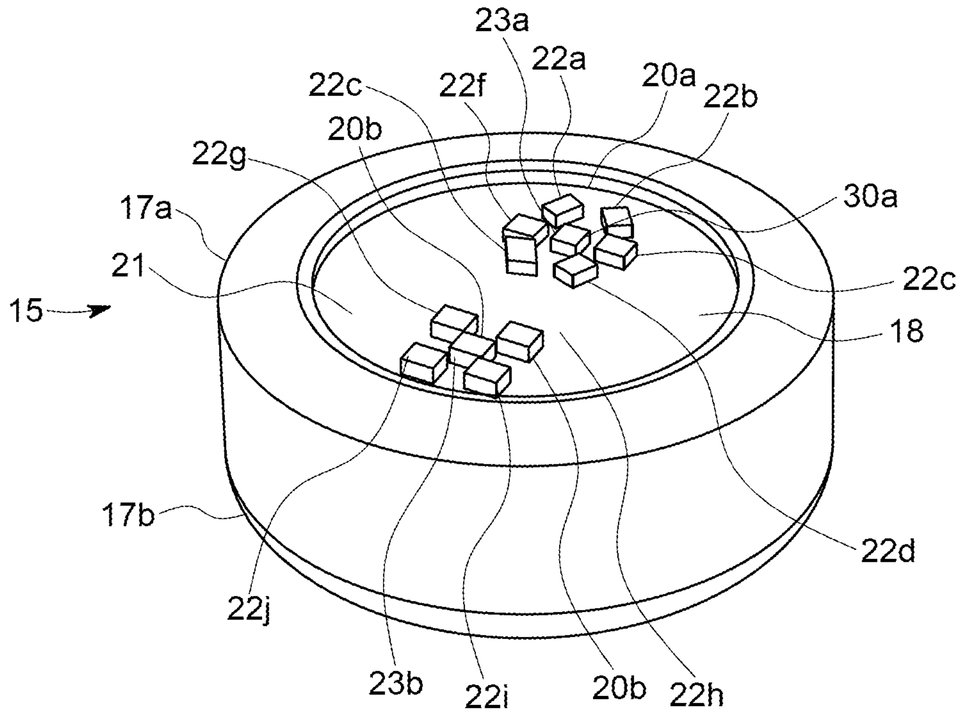
FIG. 2B presents an exemplary embodiment of the biometric sensing and monitoring device of FIG. 1, in a non-exploded view, face-up so the energy emitters and corresponding energy receivers are viewable.

Accordingly, in one aspect, the disclosure is directed to a biometric sensing and/or monitoring apparatus 10, as illustrated in FIG. 2A. In this instance, the apparatus 10 is shown in an exploded view, and is configured as a patch 11. The patch 11 may be configured to include a sensing and monitoring device 15, as shown in FIG. 2B, an encasement member 14, for encasing the sensing and monitoring device 15 and holding it in place, and an attachment structure 12 for attaching the patch 11 to the body of an individual, as depicted in FIG. 6A. As can be seen with reference to FIGS. 2A and 3A, the encasement member 14 is configured for being coupled to the attachment structure 12 so as to from the patch 11. This coupling can be effectuated by a variety of different mechanism, but as depicted the coupling can be effectuated with an adhesive sealing element 13, which can function to both couple the encasement member 14 to the attachment structure 12, as well as to form a waterproof sealing therebetween.

Figure 3A:
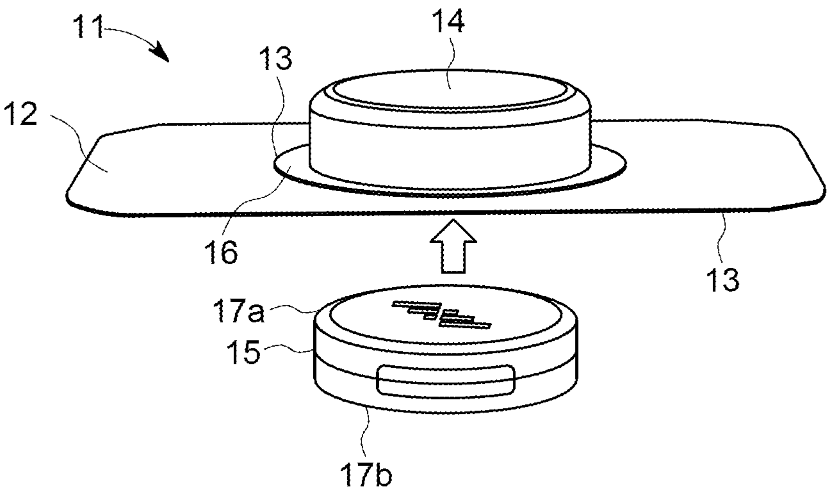
FIG. 3A presents a side, perspective view of a first embodiment of an attachment structure, configured as a patch member, which is coupled a with a dome shaped encasement, where the encasement is configured for incorporating the biometric sensing and monitoring device of FIG. 2B within it, in accordance with the teachings of the disclosure.
Figure 3B:
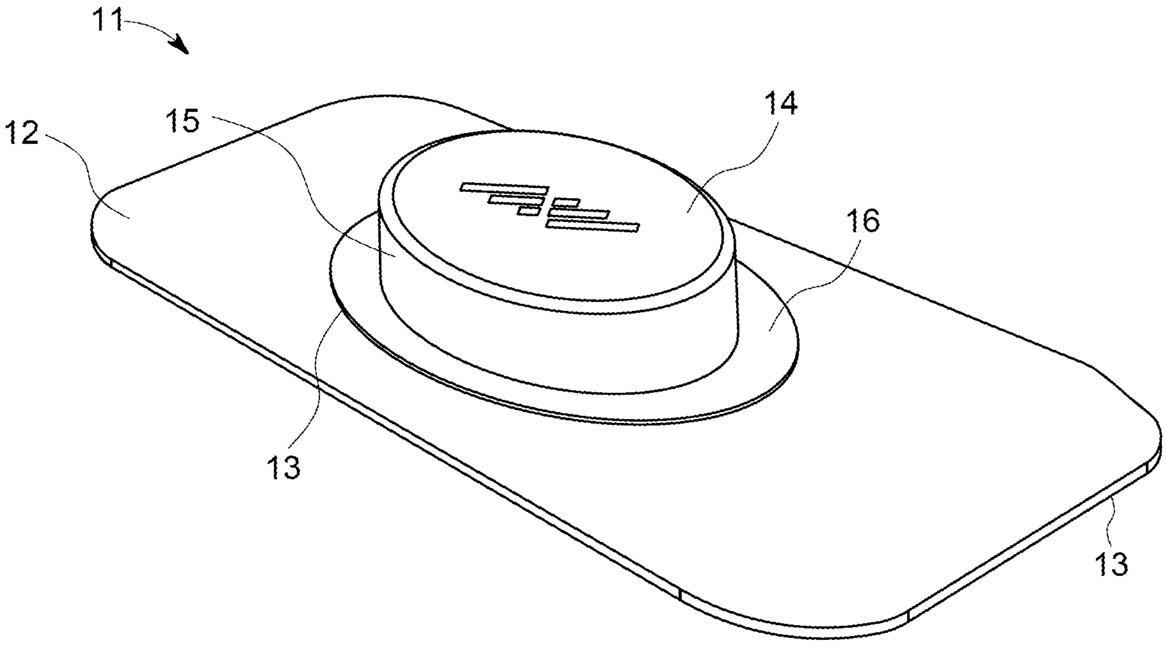
FIG. 3B presents a perspective view of the biometric apparatus of FIG. 3A, including an attachment structure, encasement, and the biometric sensing and/or monitoring device of FIG. 2B, where the biometric sensing and monitoring device has been fully incorporated within the dome of the encasement.

As shown in FIG. 3A, once the encasement member 14 is coupled to the attachment structure 12 the patch 11 is formed, then the sensing and monitoring device 15 may be inserted into the patch 11, such as by being inserted into encasement member 14, as shown in FIG. 3B. Likewise, once the sensing and monitoring device 15 is inserted into the encasement member 14, so as to be encased thereby, the biometric apparatus 10 is formed, as seen in FIG. 3B. The attachment structure 12 can then be securely attached to the body 100 of the individual, such as through the addition of a further attachment element 13, such as a bio-acceptable adhesive, to a skin facing surface of the attachment structure 12. The adhesive in this instance may be such that it securely effectuates the attachment of the patch 11 to the body 100, as shown in FIG. 6A, but is capable of allowing the apparatus 10 to be removed with the application of a removing force.

As indicated, the encasement member 14 is configured for receiving the sensing and monitoring device 10 therein. So being, the encasement member may be configured as a dome 14. Particularly the encasement dome 14 may be composed of a plurality of horizontally extended flat surfaces that are offset from one another by a bounding surface or wall. Essentially, a first flat surface may form the top of the dome, and a second flat surface can form the bottom or base of the dome, such as where the bottom base surface further acts as an interface 16 by which the dome 14 may be coupled with the attachment structure 12, as shown in FIG. 2A.

As depicted the first and second flat surfaces of the dome are parallel but offset from one another by the bounding surface, which bounding surface is positioned substantially normal to the first and second flat surfaces. In this configuration, the first, e.g., top, surface and the second, e.g., bottom, surface do not overlap in their extension. Together the top flat surface and the substantially perpendicular bounding surface form the dome 14, and further define an opening of a cavity of the encasement member, into which cavity the sensing and monitoring device 15 may be fitted, as shown in FIG. 3A. In this regard, the height of the bounding surface, as well as the distance across one bounding surface to an opposed bounding surface, e.g., the diameter, should be such that the sensing and monitoring device 15 may be securely and snuggly fitted within the dome 14, hence, the dome 14 may be slightly larger than the sensing device 15, such as by 1 mm or less. Further, as indicated, the base surface 16 of the dome 14 may form an attachment interface, extending laterally outwards from the bounding surface, by which the encasement member 14 may be coupled to the attachment structure 12 in a manner that the opening of the cavity is coincident with a corresponding opening of the attachment structure 11, as shown in FIG. 3A.

Likewise, the attachment structure 12 may have any suitable shape and/or configuration so long as it is capable of attaching the sensing and monitoring device 15 in close proximity to the skin of the wearer, such as via a suitably configured coupling with the dome member 14, as shown in FIG. 3B. For such purposes, the attachment structure 12 may have an elongated surface member that includes a top surface, such as for interfacing with the dome member 14, as well as a bottom surface for interfacing with the body of an individual who is to wear the apparatus 1. This elongated surface member may have an interior portion and an exterior portion, such as where the exterior portion is defined by a perimeter bounding member.

As such, the exterior perimeter bounding member of the attachment structure 12 may form a single circumferential, outer perimeter, such as in the shape of a circle, or may be composed off opposite sides, so as to form a triangle, square, rectangle, and the like, e.g., dependent on the number of sides. Further, the elongated surface member 12 may include an inner perimeter portion defining an opening, e.g., sized so as to be coincident with the opening of the dome 14, such that the sensing and monitoring device 15 may be fitted therethrough so as to both be inserted into the dome 14 and abut the skin of the wearer, when the apparatus 10 is placed on the body. In some embodiments, this opening in the interior portion of the attachment structure 12 may be covered with a transmissive covering so that the sensing device 15 does not actually touch the skin. As indicated, the bottom portion of the elongated surface 12 may be coupled with an attachment element, such as an adhesive 13, for coupling the overall apparatus 10 to the body of the wearer.

Accordingly, in view of the above, in another aspect, the disclosure is directed to a sensing and monitoring device 15 as set forth in FIG. 2B, such as for determining a characteristic of one or more biomolecules present within a living tissue of an individual. In particular implementations, the device 15 may further be configured for determining, or otherwise predicting, a state, or a change in a state, of the individual, such as based on a value of the one or more biomolecules being present within the tissue. As depicted in FIG. 2B, the sensor and/or monitoring device 15 is shown sensor-side up, so as to show the details of the device, but in use, the sensor-side would be face down so that the sensor elements would be facing the skin of the body tissue, such as when the sensor device 15 is inserted within an encasement member 14 of a patch 11, and the patch is applied to the skin, as shown in FIG. 6A.

As illustrated, the hardware of the monitoring and sensing device 15 may include a housing 17 that retains a sensing and/or monitoring unit 18 there within. The housing 17 may be composed of an upper 17*a* and a lower 17*b* housing or cover member, and, as illustrated, may include a protective glass 21, such as at a skin interface of the bottom cover member 17*b*. This transmissive portion, e.g., window, is useful because it allows for, or otherwise facilitates, passage of electromagnetic radiation, e.g., light and/or sound, of determined wavelengths, being emitted from the sensor unit 18, to pass therethrough. However, although the bottom cover 17*b* may include one or more windows 21, in other instances, the bottom cover 17*b* may be formed of a transmissive material, such as where the entire bottom portion is composed of the transmissive material, such as protective glass.

Since the sensing and/or monitoring device 15 is configured to be worn for a prolonged period of time contacting the skin, the cover members 17*a*, 17*b* may be formed of a material that is non-toxic, non-irritative, bio-compatible, and/or may otherwise be capable of being pressed against the skin of a user without adverse effects. In certain instances, the housing may be 3D printed with acrylic resin that becomes rigid when hardened. The housing may have any suitable shape and configuration. However, for ease of use, and to promote a thin profile, the housing 17 may have a circular, disk-like shape. Nevertheless, in various instances, the housing 17 may be in the shape of a triangle, square, rectangle, and the like, so long as the form factor is capable of containing the electronics of the device, and yet maintaining a stream-lined, low profile.

As indicated, the housing 17 is configured for retaining a sensor and/or monitoring unit 18 therewithin. So being, the housing may have a top housing or cover member 17*a* and a bottom housing or cover member 17*b* that are configured for being coupled together so as to encase the sensor unit 18 as well as the other electronic components 60 of the sensing and monitoring device 15. Particularly, each top 17*a* and bottom 17*b* member of the sensor device housing 17 may have both an extended planar surface as well as a perimeter surface 19, such as where the perimeter surface may include one or more bounding walls 19*a*, 19*b* that extend substantially normal to an outer edge of the extended planar top and bottom surface members 17*a* and 17*b*. In such instances, as can be seen with respect to FIG. 2A, when the corresponding bounding walls of the top and bottom cover members are coupled together a cavity is formed therebetween.

Accordingly, as can be seen with respect to FIG. 2B, the sensing and/or monitoring device 15 may include a housing 17 for containing the sensor unit 18 and the associated electronics 60 within the device. As depicted the housing 17 includes a top member 17*a* and a bottom member 17*b* having extended top and bottom surfaces, which are further defined by respective perimeter portions 19*a*, 19*b*. As can be seen with respect to FIG. 2A the top and bottom members 17*a*, 17*b* along with the perimeter portions 19*a*, 19*b* have interior surfaces, e.g., defining the inside of the cavity, and also have outward surfaces. Consequently, in this regard, the perimeter portions 19*a* and 19*b* may be configured as bounding members.

As depicted, the perimeter portions 19*a*, 19*b* of the top and bottom members are configured to extended normal to the relatively flat surfaces of the top and bottom members 17*a*, 17*b*. In this manner, when the top member 17*a* and the bottom member 17*b* are coupled together, via the coupling of the perimeter portion bounding members 19*a* and 19*b*, a cavity is formed between the top 17*a*, bottom 17*b*, and bounding 19*a*, 19*b* members, in which cavity the sensor unit 18, and other electronic components 60 of the sensing and/or monitoring device 15, may be retained. As depicted, the top 17*a* and bottom 17*b* surfaces are substantially flat, and the cavity is formed by the height of one or more of the perimeter bounding portions 19*a*, 19*b*. However, in various embodiments, the surface of the top and bottom members 17*a*, 17*b* may be curved, e.g., radially, such that the perimeter portions 19*a*, 19*b*, are minimally extended, and thus, do not really serve a bounding function. Rather, as the top 17*a* and bottom 17*b* members are coupled together, the sensor unit 18, and associated electronic components 60, can be retained within a natural cavity that is formed by the opposed, corresponding curvatures of the top and bottom surface members 17*a*, 17*b*. In such an instance, the perimeter portions 19*a*, 19*b* may be minimally extended, if at all.

Further, as depicted in FIG. 2B, the sensing and monitoring device 17 is configured as a circular disc-like member. However, in various embodiments, the sensing and monitoring device 15 may also have a square or rectangular-like configuration, in which case each of the bounding members 19*a* and 19*b* may be composed of a plurality of opposed perimeter walls, such as to form a square or rectangle or other edged shape. For instance, other shapes may also be formed, such as by increasing the number, shape, and orientation of the bounding walls. In any of these configurations, the top 17*a* and bottom 17*b* members may include a coupling mechanism, such as for latching the top 17*a* and bottom 17*b* members together to form the housing 17. In such instances, the coupling mechanism 39 may be configured as a tongue and groove, as opposed teeth, such as in a configuration approximating opposed "L" shapes, as corresponding latches, clips, snaps, hook and loop, opposed posts of differing diameters, such that one post fits within the other, and the like, such that the two members of the housing 17 may be snaped together. In particular embodiments, the two members of the housing 17 may be coupled together by a fastener, such as a rivet, screw, bolt, an adhesive, such as glue, and the like. In various embodiments, a compressible member 38, such as an O-ring, may be included between the corresponding latches so as to be compressed by the latching and thereby form a waterproof sealing between the two members.

As further can be seen with respect to FIG. 2A, the biomolecule sensing and/or monitoring device 15 may include, or may otherwise be composed of: a sensing unit 18, a power unit 48, a printed circuit board arrangement (PCBA) 42, along with one or more electronics modules 60, all of which may be fitted within the housing 17. As shown in FIG. 2B, an essential feature of the sensing device 15 is the sensor unit 18 having one or more sensor arrays 20, such as where each sensor array 20 may include one or more energy emitters 22 and receivers 23, all of which can be coupled to the PCB 42 and be powered by the power unit 48. Because the device is configured to be worn on the body 100 of a wearer for a prolonged period of time, without being removed for showering, swimming, and the like, so as to ensure the continuous monitoring of the body tissues, it is useful for the device to have a thin, circular profile, such as for ease and longevity of wearing.

Consequently, the dimensions of the housing 17, sensor unit 18, power source 48, and on-board electronics 60 herein disclosed have all been miniaturized to be both small, but also, in some embodiments, circular; although the configuration may also be square or rectangular. Hence, the sensor unit 18, including the emitters 22 and receivers 23, in conjunction with the PCBA 42, have been adapted so as to have a circular form factor, but the shape will be dependent on the shape of the overall housing of the device. However, with respect to the size of the housing 17, the size may be dependent on the collective size of the included sensor and electronic components necessary for performing the disclosed activities. In various instances, the sensor device may be less than 10 mm, such as from about 1 or 2 mm to about 8 or 10 mm, such as about 3 or 4 mm to about 6 or 7 mm, including about 5 mm in height. Likewise, the sensor device may have a cross-wise length from about 2 mm to 5 mm or 10 mm or 12 mm to about 40 mm or 50 mm, such as from about 15 mm or 20 mm to about 25 mm or 30 mm, such as dependent if the form factor is circular or square. In particular iterations, such as where the sensing and/or monitoring device 10 has a circular form factor, the diameter of the overall device may be less than about 5 cm, such as less than about 4 cm, or less than about 3 cm, such as less than about 2 cm or less. Likewise, the height may be less than 5 cm, such as less than 4 cm or 3 cm, for instance, less than 2 cm, less than 1 cm, such as about 5 mm.

As can be seen with respect to FIG. 2B, a key component of the biometric sensor and/or monitoring device 15 is the sensor unit 18 that is configured to include a plurality of miniaturized sensor arrays 20. For instance, the biometric sensor unit 18 may include a plurality, e.g., two, sensor arrays 20*a* and 20*b*. Each sensor array 20*a*, 20*b*, may include one or more electromagnetic radiation emitters 22 and one or more electromagnetic radiation receivers 23, each being arranged on a printed circuit board 42 within in the housing 17. As indicated, the electromagnetic radiation emitter may be configured as a photoemitter 22, which may be adapted for directing light into the body of the wearer of the device 15. Likewise, the electromagnetic radiation receiver may be configured as a photodiode 23, which may be adapted for receiving residual light waves reflected back from the skin.

Figure 2C:
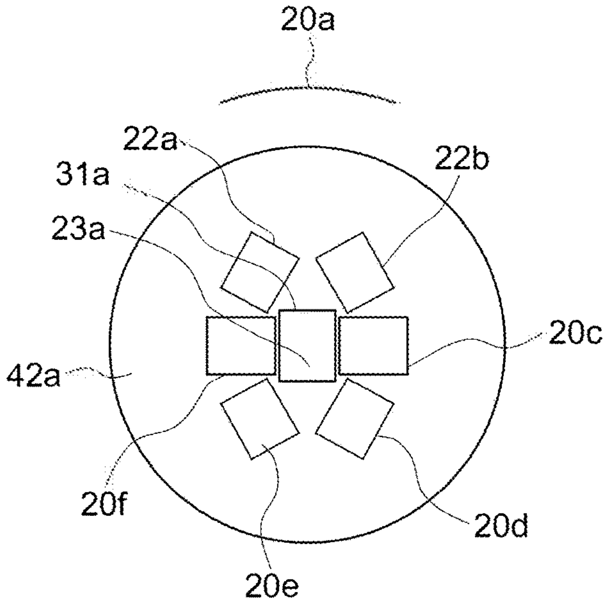
FIG. 2C presents the sensor unit of FIG. 2B, including an array of 6 energy emitters exemplarily arranged around a first energy receiver, such as a first photodiode.
Figure 2D:
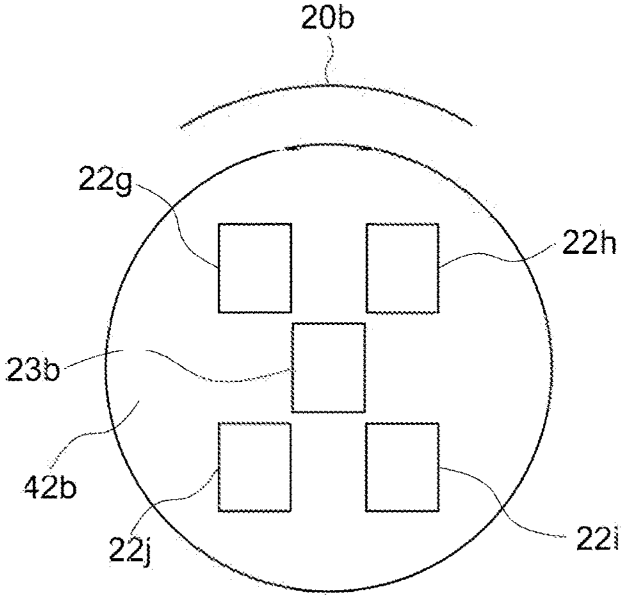
FIG. 2D further presents the sensor unit of FIG. 2B, further including an array of four energy emitters exemplarily arranged around a second energy receiver, such as a second photodiode.
Figure 5A:
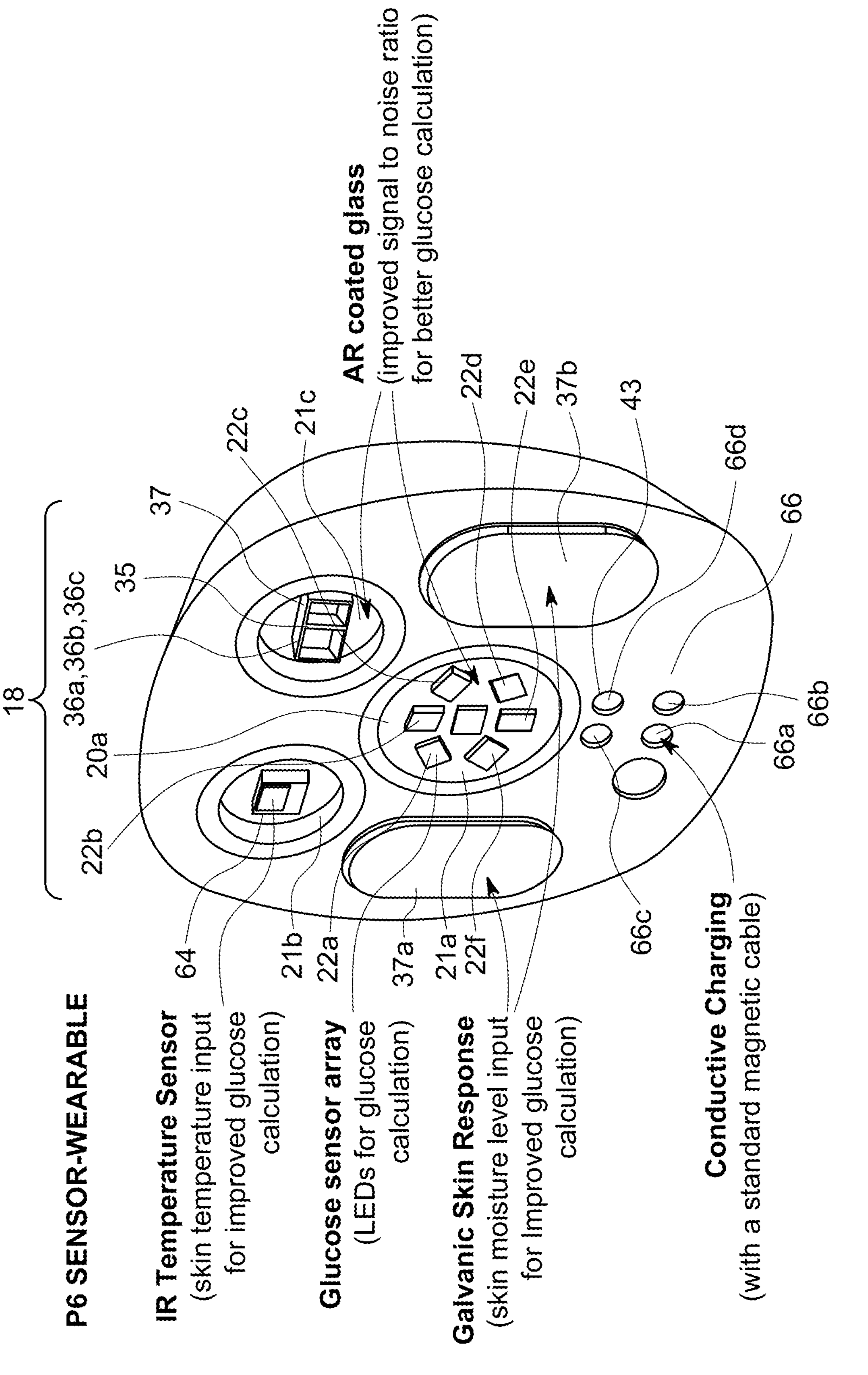
FIG. 5A presents a perspective view of a second embodiment of a biometric sensing and monitoring device for sensing the presence and a value of a biomolecule of interest in a non-invasive and continuous manner in accordance with the teachings of the specification; the sensor device is depicted face-up so the energy emitters and corresponding energy receivers are viewable.

Further, as shown in FIG. 2B, an electronics module 60 of the sensor and monitoring device 15 may include a sensor unit 18 that may be positioned on the PCB 42. The sensor unit 18 may be composed of a sensor array 20, which sensor array 20 may include an energy, e.g., electromagnetic radiation, emitter 22 as well as an energy, e.g., electromagnetic radiation detector 23. As depicted in FIG. 2B, the displayed sensor unit 18 includes a first array 20*a* of six energy emitters 22*a*, 22*b*, 22*c*, 22*d*, 22*e*, and 22*f* surrounding a first energy receiver 23*a*, as depicted in FIG. 2C, and further includes a second array 20*b* of four energy emitters 22*g*, 22*h*, 22*i*, and 22*j* surrounding a second energy receiver 23*b*, as depicted in FIG. 2D. Although depicted with two sensor arrays 20*a* and 20*b*, one more of these arrays may be substituted out for other sensor arrays, having different configurations, as illustrated in FIG. 5A, or may be substituted out for different electronic components all together. In particular embodiments, a sensor unit 18 may have more than two arrays 20, such as three, or four, or five, etc., where each array may have 1, 2, 3 to 5 to 10, or more energy emitters, and/or 1, 2, 3-10, or more energy receivers.

Hence, in particular embodiments, the sensor unit 18 may include one or more, e.g., a plurality, of arrays having one or more emitters. The emitters may be configured as photoemitters, or they may be adapted for emitting other types of radiation, such as RF or microwaves. For instance, an emitter array may include collection of one or more light emitting diodes, LEDs, for the emitting of light waves may be included. However, in other embodiments, an emitter array may include collection of one or more antennas, such as for the emission of radio or microwaves. Consequently, in certain instances, in one or more of the emitters of one or more of the array may be a sound or microwave generating device, in which instance, the receiving unit may be configured for receiving, sensing, and/or determining reflected and/or refracted sound or micro waves.

Accordingly, the sensor unit 18 may further include one or more arrays 20 of energy receiving elements 23, such as including one or more receivers for receiving and sensing radiation, e.g., electromagnetic radiation, that is reflected and/or refracted back from tissues that have been irradiated with light waves, sound waves, and the like. In particular embodiments, as can be seen with respect to FIG. 2B, the energy receiver 23 can be positioned in close proximity of the energy emitters 22, such as where the energy emitters 22 virtually surround the energy receiver 23, for example, in a circular-like configuration, such as depicted by the array 20*a*, or in a square-like configuration, such as depicted by the array 20*b*. Other configurations are also possible, depending on the number of emitters and receivers as well as their ratios. In particular implementations, the sensor unit 18 may be configured as a light sensor such that the one or more emitters 22 are configured as photoemitters, in which case, the sensor unit 18 will also include one or more, e.g., a plurality of, diodes, e.g., photodiodes. Together an emitter, e.g., light emitting diode, in combination with a receiver, e.g., photodiode, may form a sensor or sensor unit herein dependent on the context in which they are recited.

As can be seen with respect to FIGS. 2C and 2D, the sensor arrays 20*a* and 20*b* of FIG. 2B are set forth. Specifically, FIG. 2C depicts the six-emitter photo-array 20*a* of FIG. 2B, while FIG. 2D depicts the four-emitter photo-array 20*b*. As can be seen with regard to the photosensor array 20*a* of the sensor unit 18, as set forth in FIG. 2C, the displayed array 20*a* includes six photoemitters 22*a*, 22*b*, 22*c*, 22*d*, 22*e*, and 22*f*. In this instance, the six photoemitters are configured in a roughly circular pattern, with a single photoreceiver, e.g., photodiode 23*a* roughly centered in the middle of the ring of photoemitters. This configuration is useful because it allows light from different emitters 20*a-f* to emit light of different wavelengths, while at the same time as ensuring that their reflected light waves will all impinge upon the centralized photoreceiver 23*a*. However, in alternative embodiments, more photoreceivers 23 per array may be included so that the emitter to receiver ratio is 6:5, 5:2, 5:3, 4:1, 3:2, 2:1, 1:1, and the like. Further, the configuration of one or more of the photoemitters 22 to one or more of the photoreceivers 23 may be such that one or more dyads are perpendicular to one another.

In various embodiments, the sensor array 20*a* of FIG. 2C may be composed of photoemitters 22 that are configured to emit light waves. In particular embodiments, the photoemitters 22*a-f* may be composed of light emitting diodes (LEDs), such as where the LEDs 22*a-f* surround one or more light receivers, e.g., photodiodes 23*a*. One or more, e.g., half or all, of the light emitting diodes 22*a-f* may be configured for emitting light of the same wavelength, or they may be configured for emitting light of different wavelengths. For instance, in one particular embodiment, the six photoemitters of FIG. 2C may be configured for emitting light of different wavelengths, such as, in one exemplary iteration where a first photoemitter, e.g., 22*a*, is configured for emitting light of a first wavelength, such as within the range from about 1000 nm and about 1100 nm, the second photoemitter, 22*b*, is configured for emitting light of a second wavelength, such as within the range from about 1100 nm and about 1200 nm, the third photoemitter, e.g., 22*c*, is configured for emitting light of a third wavelength, such as within the range from about 1200 nm and about 1300 nm, the fourth photoemitter, e.g., 22*d*, is configured for emitting light of a fourth wavelength, such as within the range from about 1300 nm to about 1450 nm, the fifth photoemitter, e.g., 22*e*, is configured for emitting light of a fifth wavelength, such as within the range from about 1450 nm to about 1550 nm, and the sixth photoemitter, e.g., 22*f*, is configured for emitting light of a sixth wavelength, such as within the range from about 1550 nm to about 1650 nm, or more. In this configuration, the one or more photoreceivers may be configured for receiving and detecting light waves in the range from about 1000 nm to about 1700 nm. It is noted that any of the wavelengths of the emitted light may vary by +/−about 10-25 nm, about +/−50 nm, about +/−100 nm, and the like. Further, the order and combination of the emitters, along with the range of wavelengths they emit, can be arranged in any logical order, although, in various instances, sequential emission has advantageous of priming the tissue being observed, and in increasing the speed of computational processing. However, in other instances, a random illumination sequence of disparate wavelengths also has advantages.

Further, as depicted in FIG. 2D, the photoemitters 22 are aligned in a canted orientation with respect to the central photoreceiver 23. Specifically, the photoemitters 22*a* and 22*b* are canted in a positive direction so as to from the shape of an arrowhead with respect to the photoreceiver 23*a*. Likewise, the photoemitters 22*d* and 22*e* are canted in a negative direction so as to from the shape of a "V" with respect to the photoreceiver 23*a*. Likewise, the photoemitters 22*c* and 22*f* are rotated so as to be 90 degrees from a centerline running through the middle of the photoemitters 22*c* and 22*f* and photoreceiver 23, such as to form an "L" or a "T" shape with respect thereto. Other arrangements, e.g., degree of angle running through the centerlines of a respective photoemitter 22/photoreceiver 23 dyad can also be used, such as from a 1-180 degree rotation one with respect to the other, such as determined to be beneficial for receiving a maximal reflectance of emitted energy waves back from the skin and/or so as to reduce the signal to noise ratio. In various instances, the photoemitter 22/photoreceiver can be orientated to be aligned vertically with one another, e.g., 90 degrees, or 45 degrees, e.g., canted, with respect to one another, parallel to one another, or any angle there in between, as determined to be beneficial with regard to increasing signal reception and reducing noise.

Further, as can further be seen with regard to the photosensor array 20*b* of the sensor unit 18, as set forth in FIG. 2D, the displayed array 20*b* includes four photoemitters 22*g*, 22*h*, 22*i*, and 22*j*. In this instance, the four photoemitters are configured in a roughly square pattern, with a single photoreceiver, e.g., photodiode 23*b* roughly centered in the middle of the box of photoemitters. This configuration is also useful because it illustrates another configuration that allows light from different emitters 20*g-j* to emit light of different wavelengths, while at the same time as ensuring that their reflected light waves will all impinge upon the centralized photoreceiver 23*b*. However, hereto, in alternative embodiments, more photoreceivers 23 per array may be included so that the emitter to receiver ratio is 4:1, 4:3, 3:2, 2:1, 1:1, and the like. Further, the configuration of one or more of the photoemitters 22 to one or more of the photoreceivers 23 may be such that one or more dyads are perpendicular to one another.

Like above, in various embodiments, the sensor array 20*b* of FIG. 2D may also be composed of photoemitters 22*g-j* that are configured to emit light waves. In particular embodiments, the photoemitters 22*g-j* may be composed of light emitting diodes (LEDs), such as where the LEDs 22*g-j* surround one or more light receivers, e.g., photodiodes 23*b*. One or more, e.g., half or all, of the light emitting diodes 22*g-j* may be configured for emitting light of the same wavelength, or they may be configured for emitting light of different wavelengths. For instance, in one particular embodiment, the four photoemitters of FIG. 2D may be configured for emitting light of different wavelengths, such as, in one exemplary iteration, where the seventh photoemitter, e.g., 22*g*, is configured for emitting light of a seventh wavelength, such as within the range from about 550 nm to about 650 nm, the eighth photoemitter, e.g., 22*h*, is configured for emitting light of an eighth wavelength, such as within the range from about 650 nm to about 850 nm, the ninth photoemitter, 22*i*, is configured for emitting light of a ninth wavelength, such as within the range from about 850 to about 940 nm, and the tenth photoemitter, e.g., 22*j*, is configured for emitting light of a tenth wavelength, such as within the range from about 940 nm to about 1000 nm. In this configuration, the one or more photoreceivers may be configured for receiving and detecting light waves in the range from about 500 nm to about 1100 nm. It is noted here as well that any of the wavelengths of the emitted light may vary by +/−about 10-25 nm, about +/−50 nm, about +/−100 nm, and the like. Further, the order and combination of the emitters, along with the range of wavelengths they emit, can be arranged in any logical order, with the same advantages set forth above.

As depicted in FIG. 2D, the photoemitters 22 are aligned in parallel with the central photoreceiver 23. However, in various embodiments, any one of the photoemitters 22*g*, 22*h*, 22*i*, and 22*j* may be canted toward one another so as to form a "V" shape, or its reverse, or they may be rotated 90 degrees with respect to the photodiode, so as to form an "L" shape, as depicted in the array 20*a* of FIGS. 2B and 2C. Other arrangements, e.g., degree of angle running through the centerlines of a respective photoemitter 22/photoreceiver 23 dyad can also be used, such as from a 1-180 degree rotation one with respect to the other, such as determined to be beneficial for receiving a maximal reflectance of emitted energy waves back from the skin and/or so as to reduce the signal to noise ratio. As set forth above, in various instances, the photoemitter 22/photoreceiver 23 can be orientated to be aligned vertically with one another, e.g., 90 degrees, or 45 degrees, e.g., canted, with respect to one another, parallel to one another, or any angle there in between, as determined to be beneficial with regard to increasing signal reception and reducing noise.

As referenced above, each cover member of the housing 17 can be formed of a solid surface, where one or more of the surfaces is transmissive to electromagnetic radiation, such as where one of the cover members, e.g., a bottom cover member 17*b*, includes a window 21. For instance, in certain embodiments, a bottom surface of the cover member 17*b*, may include a window or other opening therein that is transmissive, e.g., transparent, to light from the emitters as well as that being reflected back from the skin tissues, and where the emitter is a sound generator, the window may be transmissive to sound waves and/or microwaves. In particular iterations, the housing 17, or a window thereof 21, may be made of reinforced glass in a manner that will allow the emitters 22, e.g., LEDs of the sensor pad of the PCBA 42, to direct light from the light-emitting diodes (LEDs) through the window 21 or the bottom of the cover member 17*b* to the skin.

Consequently, it is useful for the interior of the housing to be configured to position the PCBA 42, specifically, the sensor arrays 20*a* and 20*b* associated therewith, in a manner so that the photoemitter(s) 22 and photoreceiver(s) 23 are proximate the transparent window 21 opposite the user's body tissue. Specifically, since the measurements to be taken employ emitted electromagnetic radiation, which may be in the form of light waves, the arrangement of the energy emitters 22 and energy receivers 23 on the circuit board 42 in relation to the transmissive portion of the bottom cover should be such that light, and/or other electromagnetic radiation, is allowed to easily pass from within to outside of the housing 17 and back again. In this regard, the one or more photoemitters 22 are configured to illuminate, the user's tissue below the transparent window 21, and likewise, each of the one more photoreceivers are configured to receive a return of the light reflected back from the user's tissue below the transparent window. In such instances, the energization and/or control of the photoemitters may be such that the electromagnetic radiation emitted thereby is at a predetermined frequency, amplitude and/or intensity, as well as duration and/or interval of light emission.

Hence, the sensor unit 18 may include or otherwise be coupled with, a control unit, such as including a microcontroller, for controlling and/or modulating the characteristics of the electromagnetic radiation waveforms being emitted. This modulation may be performed intermittently, such as in response to a feedback loop becoming out of line, or in accordance with a determined pattern of modulation. In any of these instances, the one or more emitters and/or receivers will be activated by the controller so as to produce a determined pattern of emittance, such as where the pattern is determined to provoke a necessary response from the tissues and their constituents so as to better determine the values and characteristics of one or more biomolecules of interest and the body's response thereto.

In various instances, it is important that light of different wavelengths be emitted in a sequential manner and at a time periodicity so that the photoreceivers are capable of receiving, detecting, and distinguishing between the emitted lights of different wavelengths. Likewise, it is useful that the amplitude and intensity of the light being emitted is not too great so as to overwhelm, and thus drown or wash out the photoreceiver and/or the body tissue being observed. For these purposes, it is useful to calibrate the sensing device with the body, and then to modulate the level of intensity of the light so that although the body responds to the light of emittance, the response is not so great as to overwhelm the ability of the body to respond to individual light waves, such as in a characteristic manner. Therefore, the light and/or orientation of emitter/receiver dyad should be attuned to the degree of the body's response, such as through modulation of the angle and/or amplitude of the wave, such as through regulating the angle of transmission and/or reception, voltage, capacitance, and/or charge of each respective photoemitter and/or photoreceiver. In particular instances, the modulation of discharge of the emitters should be in accordance with a system generated pattern of emittance, which pattern sets forth all the parameters of emittance, of which emitters will be activated, when, for how long, for what duration, at what intensity, and/or in what sequence. This may be optimized body to body and molecule to molecule.

Consequently, in various embodiments, the pattern is generated by an analytics system, whereby a series of energy waves may be generated and directed into the skin, a response thereto is perceived, e.g., by one or more photoreceivers, the results are analyzed, and one or more of the characteristics being modulated is notated and then changed. For instance, a first pattern can be implemented, such as for calibration, and after the results thereof have been analyzed, then a new pattern may be formed and a new series of emittance may be initiated. In this manner, the emitters, the wavelengths emitted thereby, their order and sequence of emittance, as well as their amplitude and/or intensity can all be finetuned to the particular biomolecule being observed as well as to the particular body that is responding thereto. All of this data may be observed, classified, and tagged, and can then be used to build a data structure, as disclosed herein, whereby each variable forms a node in the data structure, one or more correlations may be made between the various variables related to the system configurations and the results obtained, and the identified correlations can then be weighted. From this data structure a predictive model can be generated and implemented, and one or more determinations can be made, such as for generating a new pattern for configuring the system for the next round of emittance and monitoring.

The referenced modulation may be with respect to the number of photoemitters being employed, the wavelengths of energy being emitted from each emitter, their amplitude and intensity, the sequences of emitters being activated, such as with regard to their wavelengths, amplitudes, durations, angle of emittance, and the like. The modulation may be configured so that all variables are equal across emitters, such that their emissions are uniform, or in other instances, they may be non-uniform. For instance, the modulation may be variable with regard to a multiplicity of waveform characteristics being generated and directed into the skin. In various embodiments, the modulation of the emitters includes the controlling of the charging, capacitance, and/or voltage of the respective control and activation circuits of each of the photoemitters and/or receivers.

As different photoemitters 22 may emit light of different wavelengths, frequencies, amplitudes, and the like, it may be useful to distinguish light being emitted by an emitter 22, and light being received by a receiver 23. Specifically, it is useful to distinguish between the different wavelengths of light being emitted and received by different photoemitters 22 and different photoreceivers 23. For these purposes, in order to prevent light from one emitter 22 directly impinging on to a receiver 23, thereby flooding the receiver with ambient light, a light sink may be employed so as to form a barrier around one or more of the emitters 22 and/or receivers 23, such as each emitter and each receiver independently, or as one or more groups. Employment of such a light barrier is useful because it helps to prevent the photodiodes from being washed out, whereby the photoreceivers are overloaded with energy and cannot distinguish light of specific wavelengths, such as reflected light.

Therefore, in particular instances, a light sink is provided whereby the light sink is configured to surround an emitter and prevent undesired light penetration. The light sink or barrier may be formed of a non-transmissive material that circumscribes one or more emitters 22 or receivers 23, such as a metal, plastic, rubber, or other like, foam material. In various instances, the light barrier or sink may be a compressible material, such as a rubber or foam material that both surrounds the emitter and/or receiver, and is non-transmissive to various frequencies of light, such as to prevent non-reflected, infrared light impinging on the photoreceiver. For instance, in a particular embodiment, each photoreceiver 23 may be partially or completely surrounded, e.g., circumscribed, by a light barrier, such as made of rubber, which is configured to isolate the receiver from light being emitted from one or more, e.g., all, of the emitters.

Figure 2E:
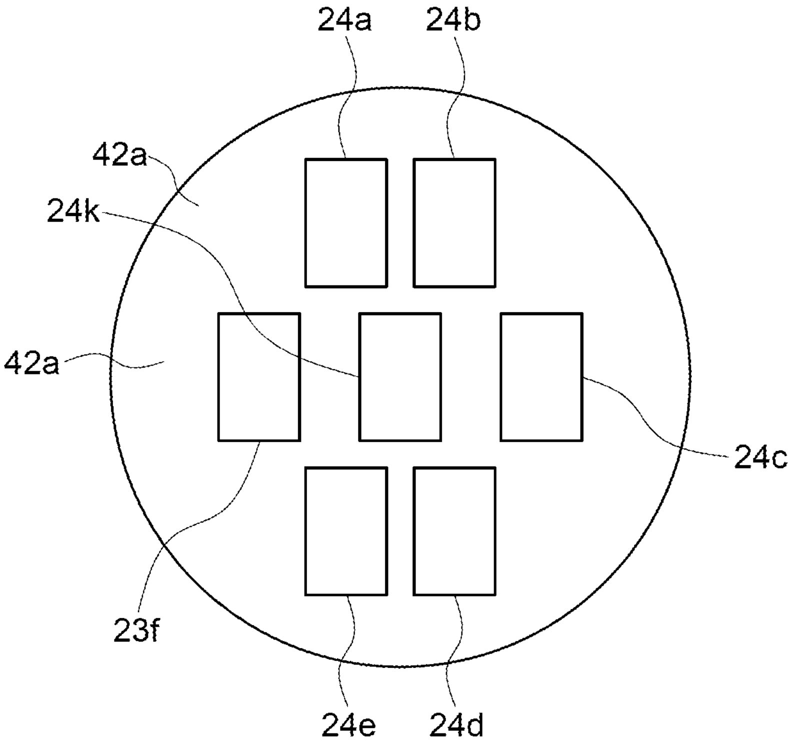
FIG. 2E presents an array of seven filters to be used in conjunction with the array of six energy emitters and one energy receiver of FIG. 2C, each filter for filtering out light of determined wavelengths.
Figure 2F:
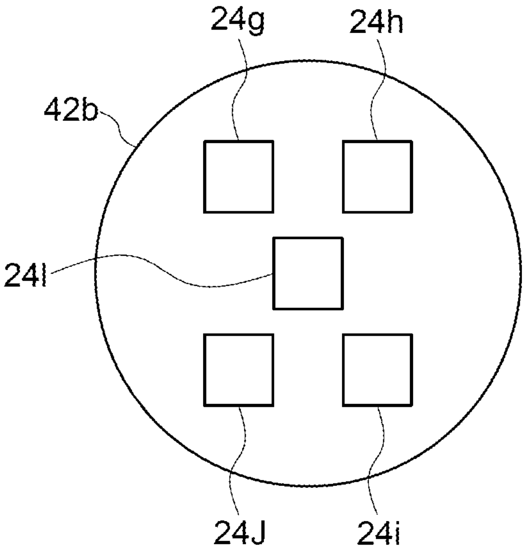
FIG. 2F presents an array of five filters to be used in conjunction with the array of four energy emitters and one energy receiver of FIG. 2D, each filter for filtering out light of determined wavelengths.

Likewise, as can be seen with respect to FIGS. 2E and 2F, in various embodiments, it is useful to also modulate the transmissive qualities of the emitters 22 and or receivers 23. For instance, one or more of the emitters 22 and/or receivers 23 may include a filter such that only certain wavelengths of light are allowed to be emitted and/or received thereby. Hence, FIGS. 2E and 2F present iterations of one or more filter assemblies that can be employed in conjunction with the device set forth in FIG. 2B. Specifically, as can be seen with reference to FIG. 2B, a sensor unit 18 of the disclosure may include an arrangement of photoemitters 22*a-f* around a central photodiode 23*a*. In this embodiment, although collectively, the emitters can generate and emit light streams in a broad range of wavelengths e.g., from 200 nm to 500 nm to 1000 nm to 1700 nm, or more, each emitter may be coupled with a filter so that it only emits a small sub-range as compared to what the range would be if not filtered and/or in regard to the collective range of all emitters together. Therefore, to modulate this emission, a series of one or more filters 24 may be employed, such that only light of a narrow band will be allowed to be emitted through the filters 24 overlaying each discrete emitter 22*a-f*. Therefore, in such instances, due to one or more of the bandpass filters 24*a-f*, the photoreceiver 23 will only receive light of discrete wavelengths, e.g., for which it may be programed or otherwise specifically attuned. The photoreceiver 23 may also be coupled with a filter 24 so as to ensure only light of desired wavelengths are capable of being detected.

Consequently, in an alternative embodiment, the reverse configuration may also be employed, such as where a broadband emitter replaces the receiver 23*a*. For instance, a single, broadband emitter 24 may be employed, such as where the emitter 24 is capable of emitting light in a broad range of wavelengths, such as from 200 nm to 500 nm to 1000 nm to 1700 nm or more. In such an instance, as depicted in FIGS. 2E and 2F, emitters 22*a*-22*f* may be replaced with narrow band photoreceivers 22*a*-22*f*, where each photoreceiver is configured for detecting discrete light waves. Consequently, in such an instance, a series of photodiodes 22*a*-22*f* are positioned around a central photoemitter 23*a*. A filter 24*a*-22*f* may then be placed over each photodiode 22*a-f* such that each photodiode can receive and detect a very narrow range of wavelengths. For example, in one embodiment, the filters 24*a*-24*f* may be configured for filtering light at the following frequencies: 1050 nm, 1200 nm, 1300 nm, 1450 nm, 1550 nm and 1650 k, such as where each filter is configured to filter light at one or more of those ranges. Other arrangements are possible. For example, in one particular alternative embodiment, where the six photoreceivers 22*a-f* have been replaced with photodiodes 22*a*-22*f*, the first photodiode filter, 24*a* may filter light in the range from about 1000 nm and about 1100 nm, the second photodiode filter 24*b* may filter within the range from about 1100 nm and about 1200 nm, the third photodiode filter 24*c* may filter light in the range from about 1200 nm and about 1300 nm, the fourth photodiode filter 24*d* may filter light in the range from about 1300 nm to about 1450 nm, the fifth photodiode filter 24*c* may filter light in the range from about 1450 nm to about 1550 nm, and the sixth photodiode 24*f* may filter within the range from about 1550 nm to about 1650 nm.

The same is true with respect to FIG. 2E, where an alternate sensor arrangement is set forth whereby the photoemitters 22*g-j* have been replaced with photodiodes and are configured around a central broadband photoemitter 23*b*, which is capable of emitting light that spans the range from about 200 nm to about 1000 nm. In this embodiment, the central photoemitter is configured to emit a broad range of wavelengths from about 500 nm to about 1000 nm. Likewise, to modulate this emission, a series of bandpass filters 24*g-j* have been positioned over photodiodes 22*g-j*, such that only light of a narrow band will be allowed to be received through the filters 24 overlaying each discrete photodiode 22*g-j*. Therefore, each photoreceiver will only receive light of discrete wavelengths, e.g., for which it may be programed. For instance, in one alternative configuration, the seventh photodiode, e.g., 22*g*, may include a filter 24*g* that is configured for filtering light of a seventh wavelength, such as within the range from about 550 nm to about 650 nm, the eighth filter, e.g., 24*h*, is configured for filtering light of an eighth wavelength, such as within the range from about 650 nm to about 850 nm, the ninth filter, 24*i*, is configured for filtering light of a ninth wavelength, such as within the range from about 850 to about 940 nm, and the tenth filter, e.g., 24*j*, is configured for emitting light of a tenth wavelength, such as within the range from about 940 nm to about 1000 nm. In this configuration, the photoemitter 23*b* may be configured for emitting light waves in the range from about 500 nm to about 1100 nm.

In any of these embodiments and/or alternative configurations, once the reflected and/or refracted light is received, or otherwise collected by a corresponding photoreceiver, which in some instances may be filtered, a return signal may be generated, e.g., in response to collecting the reflected light. An on-board processing module 45, positioned on the printed circuit board 42, may then access and process the return signal to generate one or more digital read data. From this digital read data one or more characteristics of a biomolecule of interest may be determined, and/or one or more characteristics of a state of the wearer of the device, e.g., user, may also be determined, such as based on the body's observable response to the presence of that biomolecule within the tissues. In particularly instances, the body's response may be inferred from the spectral array produced by illuminating a portion of the body with one or more, e.g., a pattern, of waves of electromagnetic radiation.

Particularly, in various embodiments, the light sensors 23 may be configured as one or more miniaturized photodiodes that can receive reflected light and, in conjunction with the processing unit 45, can compare the emitted light to the returned light, and then use this information to detect, or otherwise determine, changes in color of the skin and surrounding tissues, such as caused by the presence of various molecules, e.g., glucose molecules, within the skin. For example, as indicated above, the presence of various molecules, such as glucose, within the blood, skin, and/or interstitial fluids may change the absorption and/or reflectance pattern of these structures in ascertainable, uniform ways. This uniformity may be within a single individual over time, or across multiple individuals. Consequently, continuous biomolecule measurements allow for patterns to emerge, which patterns can then be correlated with various conditions being experienced by the wearer of the device. These patterns can be correlated to such experienced conditions, and together, they may be correlated to the presence of one or more biomolecules being present within the body, which can be distinguished by the different spectral arrays produced thereby and observed by the wearing of the continuous biomolecule sensing and monitoring apparatus disclosed herein.

Specifically, in various instances, spectral patterns of light, sound, and/or microwaves, can be observed while both in and not in a particular state, such as while an individual is experiencing conditions pursuant to a condition like hyperglycemia, and when not experiencing such a condition. These patterns will change based on the state of the individual and the characteristics of the biomolecule(s) being present. For instance, it has been observed that these patterns change in the presence and non-presence of certain biomolecules, such as glucose. More particularly, these light absorption and reflectance patterns differ based on one or more of the conditions of the wearer, as well as, the various different biomolecules being present within their tissues. This change in spectral pattern is observable and quantifiable, such as by bombarding a skin tissue with a number of different light waves and intensities in a number of different patterns so as to derive a host of different body responses to the different waveforms and intensities being emitted. Thus, in some embodiments, a number of light emitters may be employed, e.g., sequentially, so as to produce various different patterns of observable reflectance and/or absorbance, e.g., from a number of different photoreceivers, and in view of these different patterns the quantity and level of various molecules, e.g., of glucose, within the skin, and their effect on the body, can be calculated and determined.

In provoking various different responses from the body, various different patterns of light emittance and reception, as well as light intensities and amplitudes from the electromagnetic light sources, can be employed. Therefore, according to another aspect of this disclosure, as can be seen with respect to FIGS. 4A and 4B, there is provided a method for sensing and monitoring a biomolecule present within the fluids surrounding the tissues of a body of an individual. Specifically, in various embodiments, the apparatuses, devices, and systems set forth herein may be employed to detect biomolecules, such as metabolites, e.g., glucose, within the interstitial fluids surrounding the skin cells and, in some instances, present in the blood flow.

In one exemplary embodiment, a metabolite of interest to be sensed and observed is glucose, and through such continuous observation one or more states, e.g., glycemia, hyperglycemia, pre-diabetes, diabetes, and the like, can be detected and monitored. Likewise, through such continuous monitoring, the condition may more effectively be managed. It is to be noted that although herein below, and throughout this disclosure, glucose is often referenced as the molecule of interest to be detected and monitored, other metabolites, such as other sugars, e.g., fructose, alcohol, aldehydes, alkaloids, ketones, and the like, as well as their effects on one or more states of a body, can also be detected and monitored, and the concomitant effects on the body can likewise be managed, as herein described.

Accordingly, in view of the above, provided herein is a sensing and/or monitoring device 15, which can be coupled with one or more of an encasement member 14 and/or attachment member 12 that is configured for effectuating the attachment of the sensing and monitoring device 12 in a position on the skin whereby one or more electromagnetic waves may be emitted through the device housing 17 and into the skin. In certain instances, the attachment structure 12 may function to attach the sensor device 15 directly to the body itself, but in other instances, the interaction of the attachment structure 12 may be mediated through its coupling with an attachment encasement or framework member 14, which is configured for making attachment of the device 15 to the body more comfortable. In any of these instances, the attachment of the sensing device 15 to the body should be such that once placed thereon the sensing device 15 does not move with respect to the body, unless the entire apparatus 10 is being removed.

For instance, in certain instances, as can be seen with respect to FIGS. 3A-3B, the attachment structure 12 may be a planar member with an opening to which an encasement framework, such as in the shape of a dome 14, may be coupled so as to enclose the opening on one side. In such a configuration, as shown in FIG. 3A, the sensing and monitoring device 15 may be passed through the opening in the attachment structure 12 so as to be fitted snuggly into a cavity of the encasement member 14. Once fitted therein, the entire apparatus 10 may then be coupled to a user's body, such as through a suitably configured attachment element 13. Particularly, in one embodiment, an adhesive 13 may be applied between the skin facing surface of the attachment structure 12 and the body portion 100 to which it is to be attached. In certain other embodiments, the attachment structure 12 may be configured as patch, a bandage, a sleeve, or other substrate-like device.

More particularly, as described above with reference to FIGS. 3A and 3B, in one embodiment, the sensor and/or monitoring apparatus 10 may be composed of 3 main components: a framework or dome member 14, an attachment structure 12, and the sensing and/or monitoring device 15. In particular instances, the framework member, e.g., dome 14, is configured so as to immovably encase the sensing device 15, and to additionally be coupled to the attachment structure 12, such as via a suitably configured attachment element 13. The attachment element may be any suitable element for coupling the dome 14 to the attachment structure, for example, an adhesive, a fastener, e.g., a hook and loop fastener, a clip, button, a zipper, a band, a stretchable sleeve, and the like. In one particular embodiment, as can be seen with respect to FIG. 2A, the dome member 14 may be coupled to the attachment structure 12 through the addition of an adhesive ring 13, such as a ring having adhesive on both sides. In such an embodiment, the encasement member 14 may have an attachment interface 16 that is an extended element at the base of the encasement dome 14, such as where the extended element is less than about 10 mm, less than about 8 mm, less than about 5 mm, less than about 3, or 2, or 1 mm, and the like, in length, and to which the attachment structure 12 may be coupled, such as through an intermediating adhesive element 13.

Together, the framework dome 14 and attachment structures 12 are configured for associating the sensing and monitoring device 15 on to a base, which base in most instances may be a living body part of a wearer. However, in actuality, the base can be any surface that is permissive for penetration by light and/or sound and within which resides volatile elements the presence of which can be measured, such as by reflectance and/or a change in spectral reflectance due to a volatile element being present within the base. Specifically, the attachment structure 12 may be configured for attaching the sensing and/or monitoring device 15 to a portion of a wearer's body, such as through an appropriately applied adhesive, tape, e.g., double sided tape, or by tying, clipping, latching, wrapping, and the like.

Figure 3C:
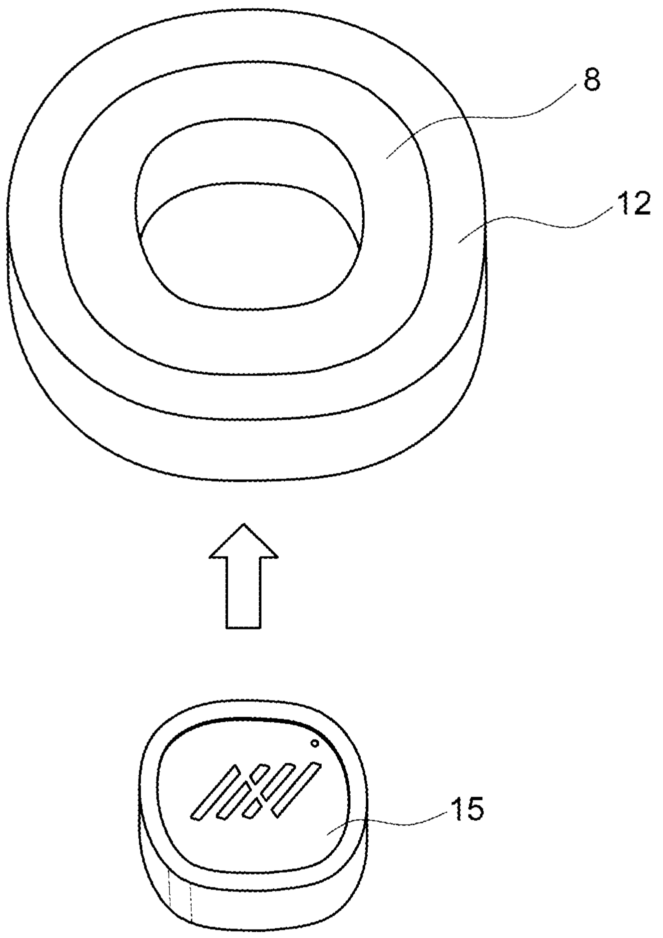
FIG. 3C presents a side, perspective view of a second embodiment of an attachment structure, configured as a patch member, which in this instance, is not coupled a with a dome shaped encasement, instead, the donut-shaped attachment structure is configured for incorporating the biometric sensing and monitoring device of FIG. 2B or 5A within it, in accordance with the teachings of the disclosure.

As discussed above, the attachment structure 12 may be configured for effectuating the coupling of the sensing device 15 to a base member, e.g., a body, part. In many instances, this coupling is facilitated through encasing the sensing device 15 within a domelike framework member 14, as shown in FIG. 3B. However, in other embodiments, the attachment structure 12 may perform the coupling without recourse to an encasement member 14, as set forth in FIGS. 3C and 3D. In such instances, the biometric sensing and/or monitoring apparatus 10 need only include the attachment structure 12 along with the sensing and monitoring device. For instance, as can be seen with respect to FIGS. 3C and 3D, in certain embodiments, a biometric sensing and/or monitoring apparatus 10 is provided, wherein the apparatus includes an attachment structure 12 that is donut shaped, such that the sensing and monitoring device 15 can be snuggly fitted in through a central opening in the surface of the attachment structure, as shown in FIG. 3C, and then the apparatus may be applied to the body 11, so as to securely hold the sensing device into substantial immovable proximity to the skin of the body. In certain instances, the securing of the sensing device 15 to the body in a manner that it is substantially inhibited from moving is by the inclusion of a stiff ring-like component 8, which gives structural firmness and support to the otherwise flexible attachment structure 12.

Figure 3D:
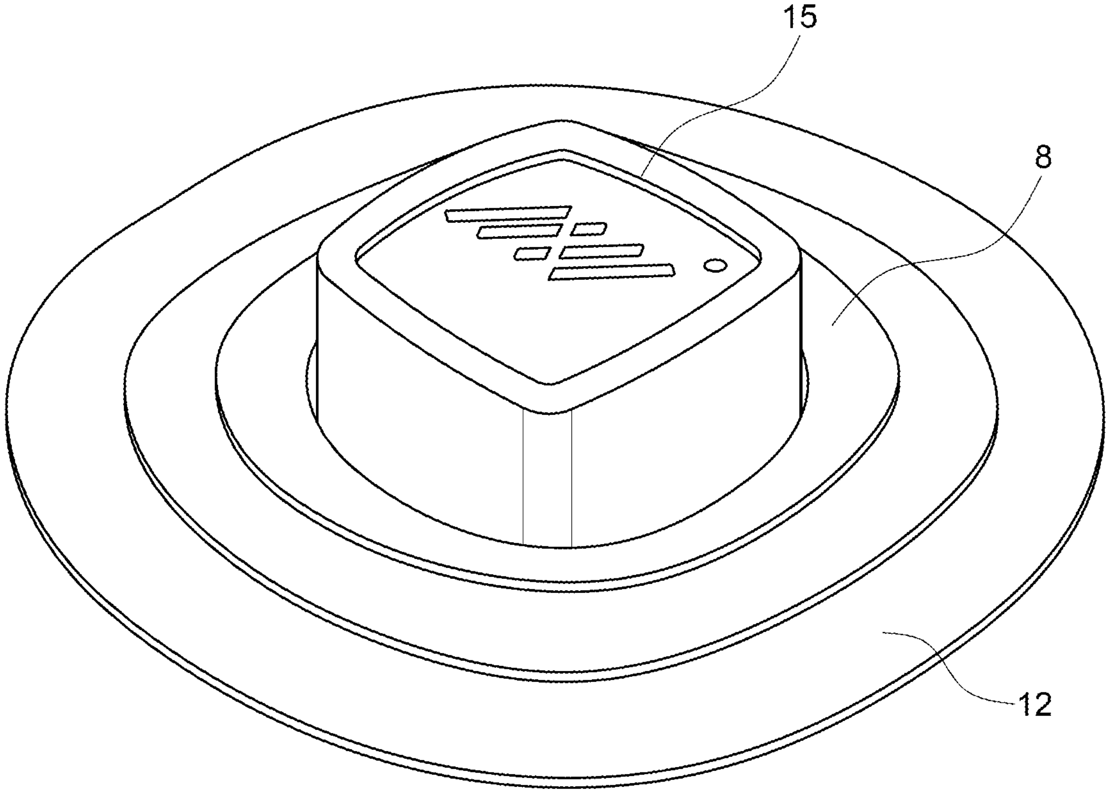
FIG. 3D presents a perspective view of the biometric apparatus of FIG. 3C, including an attachment structure and the biometric sensing and/or monitoring device of FIG. 2B or 5A where the biometric sensing and monitoring device has been incorporated within the donut hole of the structure.

In one particular embodiment, as shown in FIGS. 3A and 3B, the attachment structure 12 may be configured as an elongated surface member containing, or otherwise being associated with, an adhesive layer 13. Specifically, in various embodiments, the attachment structure 12 may be an elongated, flexible member, such as configured as a patch. In particular embodiments, the elongated surface of the attachment structure 12 may include one or more structural elements 8, that are configured for giving the surface firmness and integrity. In particular instances, the structural support member 8 may extend laterally along an X and/or Y plane of the attachment structure 12. However, in other instances, the structural support member 8 may be a circular element that circumscribes the opening through which the sensing device 15 is inserted, as shown in FIGS. 3C and 3D. In any of the aforementioned embodiments, the attachment structure 12, with or without the framework member 14, may be adapted for keeping the sensor and monitoring device 15 in place on the body, e.g., on the back of the arm, in a substantially unmoving coupling during a prolonged period of time, e.g., a 7-, 14-, 21-28-day period, during which time period, the sensor and/or monitor may be actively or passively taking periodic or continuous measurements.

Figure 4A:
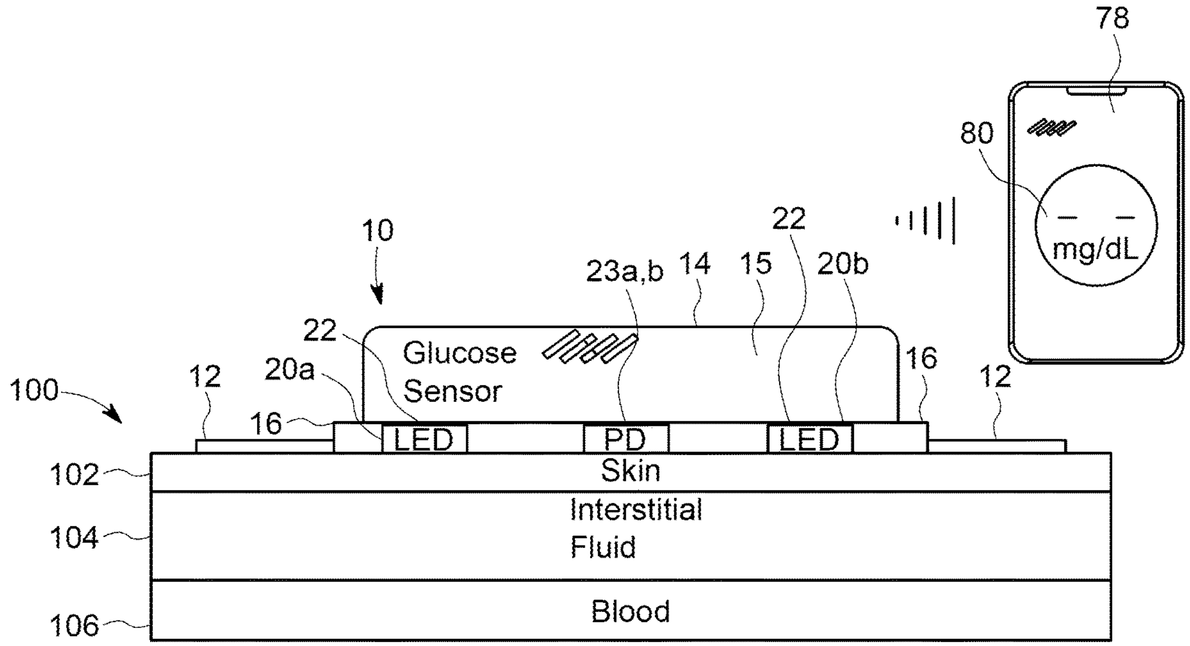
FIG. 4A illustrates the biometric sensing and monitoring device of FIG. 2B associated with the patch-like attachment structure of FIG. 3B, as it would be when the apparatus is attached to the body and being worn by a user.

For instance, FIG. 4A generally illustrates the placement of a sensor and monitoring apparatus 10 on the skin of a subject. Particularly, as depicted, the sensing and/or monitoring device 15 of FIG. 2B may be encased within an encasement framework 14 that is configured as a dome. The dome 14 in turn is associated with an attachment structure, such as a patch member 12, which patch member 12 is used to securely position the apparatus 15 on the surface of a body part 100, such as the back of the arm, as shown in FIG. 6A. In such a position, the sensing and/or monitoring apparatus may be configured to detect, measure, and/or otherwise determine activity of a biomolecule, such as glucose, within the tissues, vessels, and/or interstitial spaces of the body of a subject.

For these purposes, as can be seen with respect to FIG. 4A, the sensing and monitoring apparatus 10 is placed such that a transmissive portion of the bottom 17*b* of the housing 17 of the sensing device 15 abuts the skin's 100 surface. In particular instances, the bottom member 17*b* of the housing 17 includes one or more windows 21 therein, which window(s) contacts the skin in a manner so that the encased sensing and monitoring device 15 has visual access to the body tissues. Specifically, as can be seen with respect to FIG. 4B, once firmly applied to the body portion, the sensor unit 18 within the housing 17 is engaged such that one or more light sources thereof, such as a plurality of arrays 20*a*, 20*b* having a plurality of electromagnetic radiation emitters 22, e.g., light emitting diodes, are energized and emit light waves that pass from the inside of the housing 17, out through the transmissive portion, e.g., window, 21 of the bottom surface 17*b* and into the layers of the skin 102 and 104. Likewise, the sensor array 20 includes a number of electromagnetic radiation receivers, such as a plurality of photodiodes 23*a, b*, for detecting and receiving the electromagnetic radiation being reflected back from the skin 102 and interstitial fluids 104 therein.

Figure 4B:
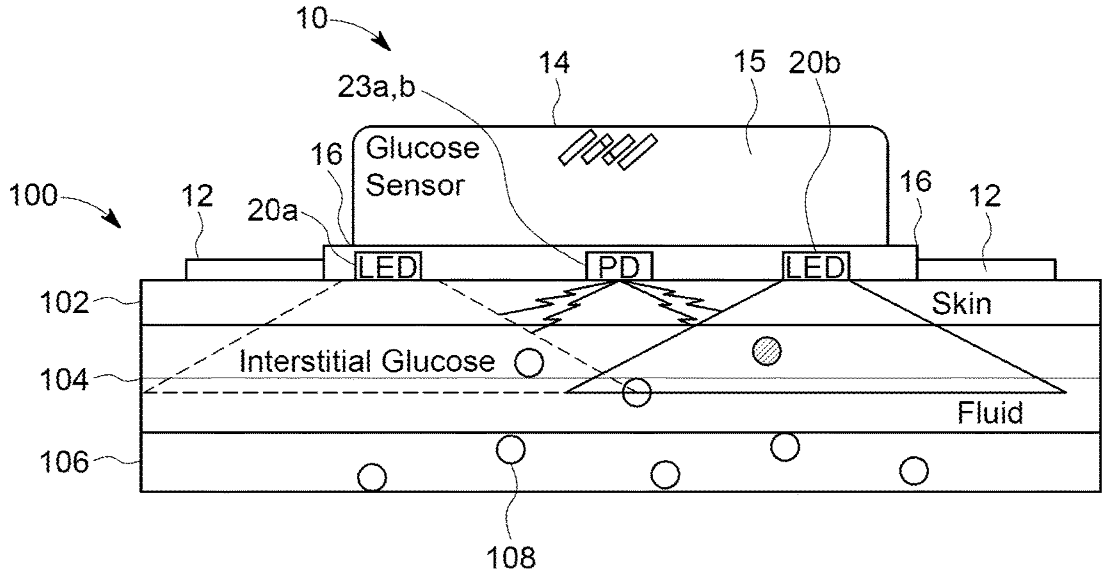
FIG. 4B illustrates the biometric sensing and monitoring device of FIG. 4A as it would be when attached to the body and being worn by a user, where the biometric sensing and monitoring device is actively performing a biomolecule sensing operation.
Figure 5B:
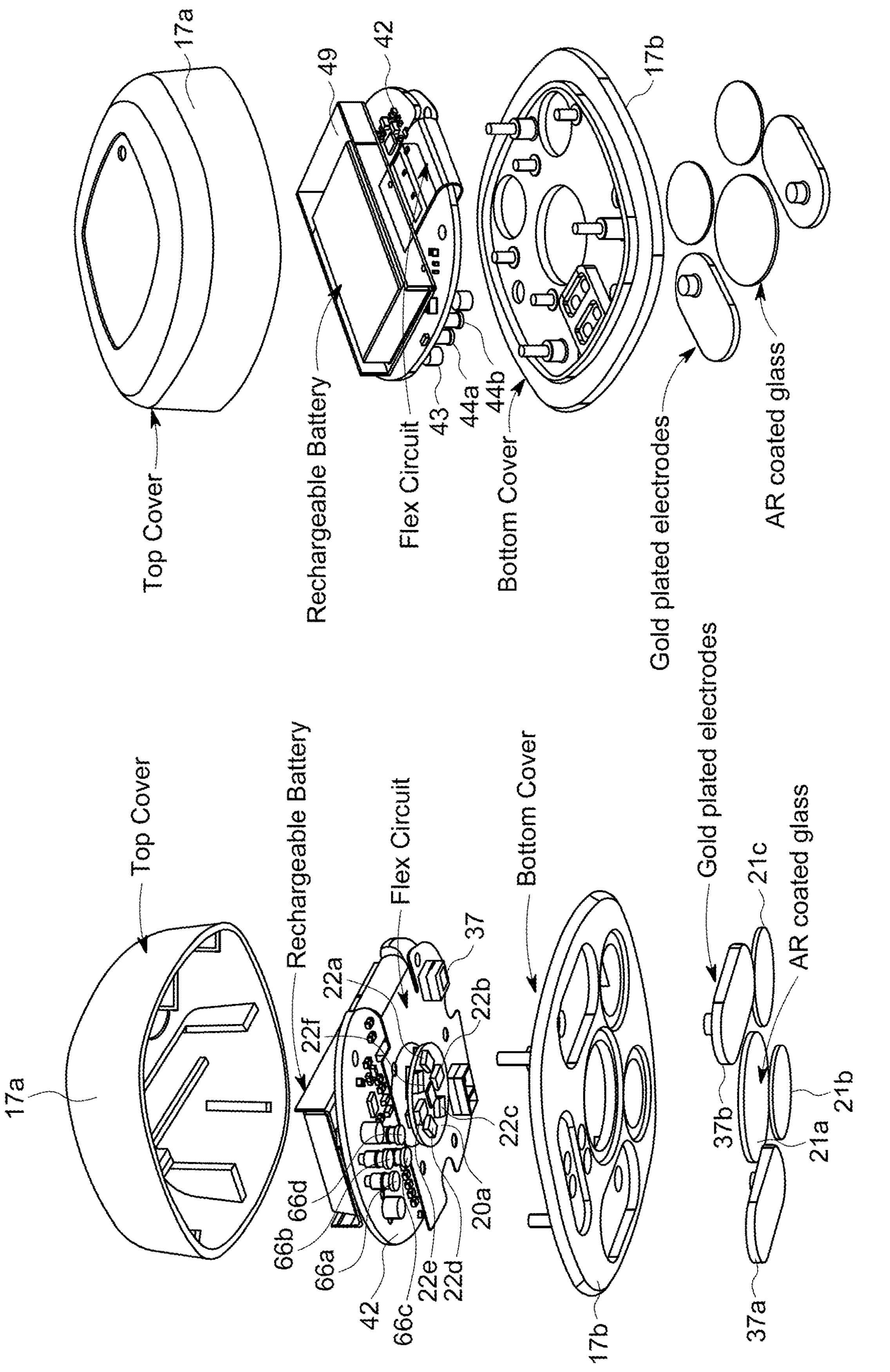
FIG. 5B presents an exploded view of the sensing and monitoring device illustrated in FIG. 5A.

As can be seen with respect to FIG. 4B, the sensor unit 18 is configured as a glucose monitor, and because glucose is a visible (e.g., green and/or red) and/or infrared, light-active component, it has been found, herein, that spectroscopy can be used to detect glucose in dermal tissue 102 and interstitial fluids 104. Consequently, in use, the sensor unit 18 of the biometric sensing and monitoring apparatus 10, initiates a first array of LED emitters 20*a* to direct a first series of lights (such as on or more of visible, green, red, near infrared, and/or infrared light) into the tissue 102 and interstitial fluid 104, as shown. This first emittance by array of LEDs 20*a* is demarcated by the broken lines. Then, the second array of LED emitters 20*b* is energized and emits a second series of lights into the tissue 102 and interstitial fluid 104. This second emittance is demarcated by the non-broken lines. Likewise, as shown, the sensor unit 15 includes one or more light based receivers, e.g., photodiodes 23 *a, b*, that are configured for receiving the various different wavelengths and intensities of the light reflected back from the tissues 102 and interstitial fluids 104. In this embodiment, the different arrays 20*a* and 20*b* emit light sequentially, and at a depth whereby the emitted light does not penetrate into the vessels and blood. However, in various other embodiments, one or more of the arrays may be configured for emitting light that impinges all the way down into the vessels and/or tissues, such as into the blood vessels, and where a multiplicity of light sources are activated at the same time, such as set forth in FIG. 5E. This configuration is useful, such as for determining blood glucose levels, such as depicted in FIG. 5D.

In any of these instances, the photodiodes 23, are configured to collect raw reflected electromagnetic radiation, as shown, from the different layers of the interstitial fluids throughout the skin layers, and then an associated analog to digital converter converts the raw reflected electromagnetic radiation data into digital signal read data. An on-board processor 45 may then analyze the raw light data that is reflected back from the various different layers of the skin, tissues, and vessels, and a communications module 43 may then transmit the data to an associated computing system 70 for analysis, e.g., spectral analysis, thereby, as depicted in FIG. 4B. Specifically, these spectral signals detected by the sensor's photodiodes are affected by a complex relationship that exists between various different biomolecules, such as glucose, being present in the interstitial fluid and/or the blood of the body's tissue, and the frequency, intensity, and exposure time of the light being directed into that tissue.

As can be seen with respect to FIG. 4B, this complex relationship represents a "glucose-mediated skin response," from which a person's present glucose characteristics, e.g., levels and/or concentration, may be determined. In such implementations, the one or more photodiodes may be configured to receive at least a portion of a first light emitted and directed into the skin by one or more of the LEDs, and reflected back therefrom into the sensor. In like manner, the photodiode, on-board, and/or other associated computing system, may further be configured to receive and/or analyze at least a portion of the second, third, fourth, fifth, sixth, tenth, etc. light being reflected and/or refracted back from the skin of the user.

Particularly, in various embodiments, the plurality of photo-arrays 20*a* and 20*b*, may include a number of LED light emitters, such as where the first LED array 20*a* includes six light emitters, and the second LED array 20*b* includes four light emitters, as embodied by the sensing device depicted in FIG. 2B. Likewise, each sensor array 20*a*, 20*b* may include one or a series of light sensors, e.g., photodiodes, wherein each light sensor is configured to receive light of the various wavelengths emitted from the ten (or more) LED emitters and reflected back from the body. Consequently, where a sensor array 20 includes a series of light sources for emitting a series of light of the same or different wavelengths, then the sensor array may further include one or more light receivers, where each light receiver may be configured for detecting and receiving reflected or refracted light in the same or similar wavelengths.

Accordingly, with respect to FIG. 4B, as set forth above, light from the various different, e.g., 10, LED emitters may be emitted and/or received at different predetermined or random frequencies, such as where the light emittance is sequential and in accordance with a pre-defined pattern. For example, each light emittance and/or reflectance/refraction may be pulsed, the durations of emittance, or pulsing, between the emitters, may be the same or variable, and/or the intensities of the light emitted may also be the same or variable. These different variables may be determined and formed into an emittance protocol as determined by the analytics system herein, such as based on the emittance patterns that are predicted to best determine the presence, concentration, and/or bodily effect of a biomolecule within the skin tissues. Consequently, the light to be emitted from the various light emitters may all be of the same or of different wavelengths, the duration of emittance may be the same between all emitters or different, e.g., the lights may be pulsed at different frequencies, and the sequence of light emittance may be sequential, e.g., based on wavelengths or durations, and likewise, the intensities may be the same or different, all of which may be determined by the analytics system and/or controlled by an on-board computing system and/or microcontrollers.

For instance, as indicated, the sensor unit(s) 18 and/or arrays 20 thereof may be coupled together with, and/or otherwise include, one or more printed circuit boards 42, which in turn may be associated with a processing module 45 that may include one or more processing units 47 and/or microcontrollers. Particularly, the processing module 45 may include one or more semiconductor chips that may be configured as a system on a chip, and thus, may integrate or otherwise be coupled with the various light emitters, e.g., LEDs, light receivers, e.g., photodiodes, converters, and other electronic components herein disclosed.

Further, in various embodiments, the processing module 45 may include, or otherwise be associated with, an AI module 72, such as incorporating a machine learning engine from which one or more models may be generated. For example, a first model may be generated and used to determine an emittance pattern and schedule, e.g., characterizing the conditions and variables of light emittance, and a second model may be generated to collect and analyze the returned spectral data. This data may then be employed to generate a third and/or fourth model by which an inference engine may then predictably determine a new pattern of emittance as well as determine a level, e.g., a concentration, of a biomolecule within the tissues of a wearer of the device and/or to predict a state of their being, such as based in part of the various different patterns of light emittance.

Figure 5C:
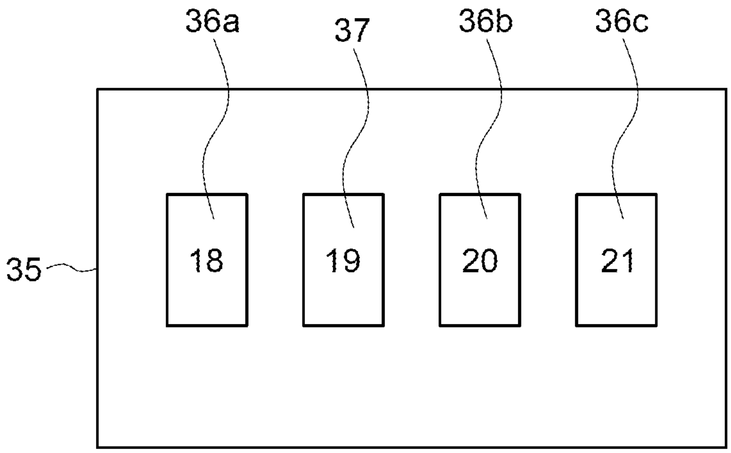
FIG. 5C presents an exemplary sensor array of the PPG sensor of FIG. 5A with three photoemitters and one photoreceiver depicted.
Figure 5D:
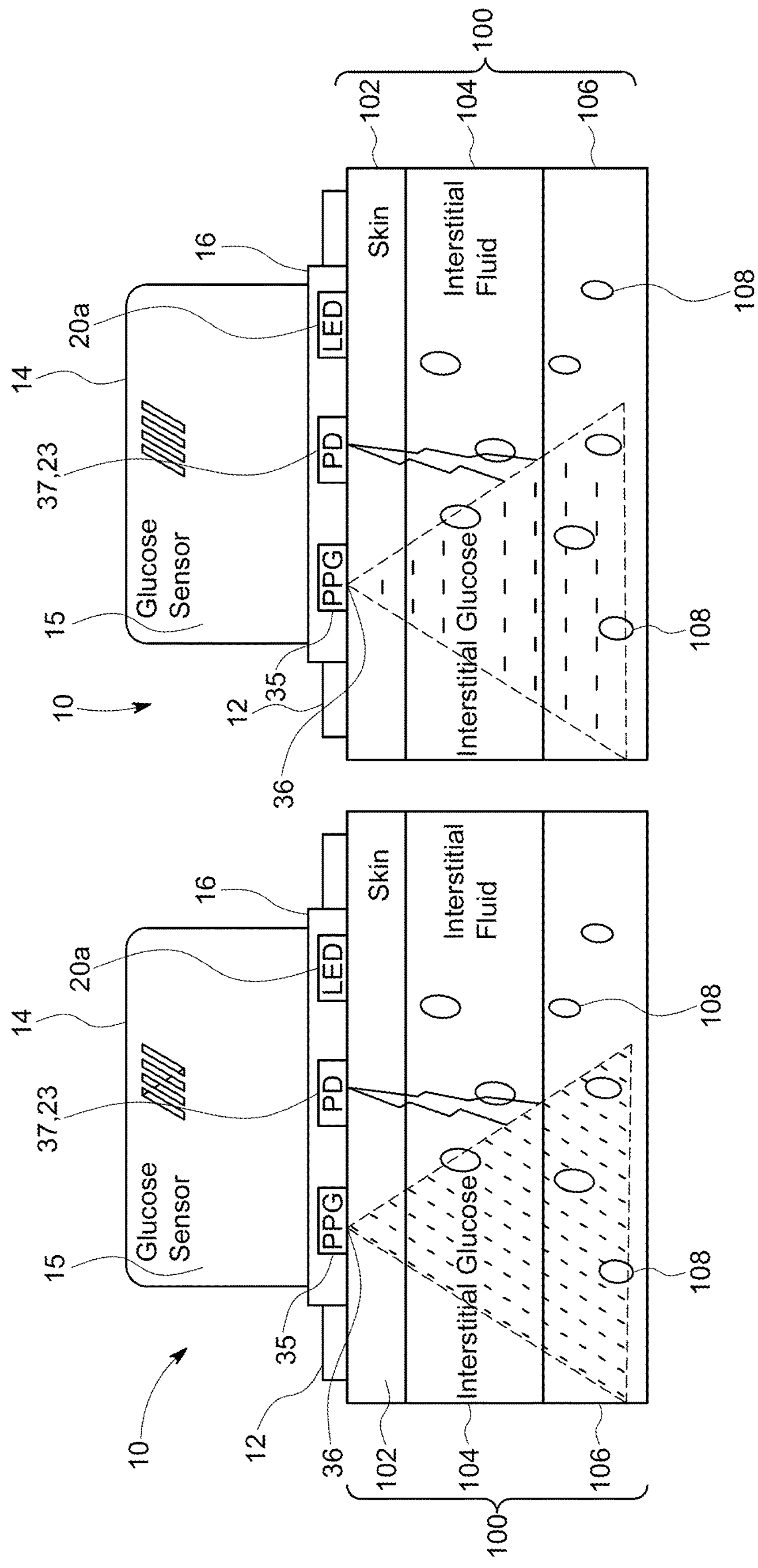
FIG. 5D presents an exemplary embodiment of the biometric sensing and monitoring device of FIG. 5A including a photoplethysmography (PPG) sensor unit array substituted for the four-emitter array of FIG. 2A, where the biometric sensing and monitoring device is attached to a body and actively performing a PPG sensing operation.
Figure 5E:
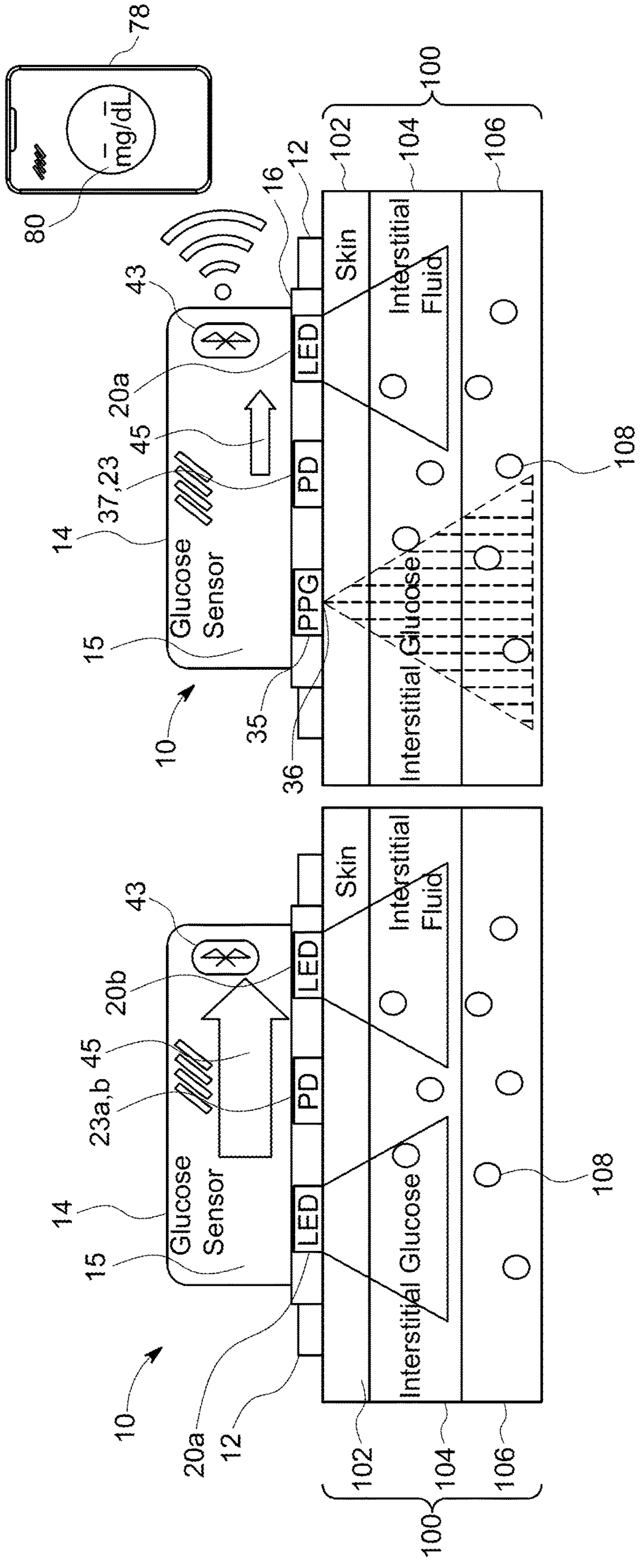
FIG. 5E illustrates embodiments of the biometric sensing and monitoring device of the disclosure after the sensed data has been collected and pre-processed and then transmitted, wirelessly to an external computing device.

Hence, in one exemplary embodiment, as can be seen with respect to FIGS. 4A and 4B and also FIGS. 5D and 5E, a non-invasive glucose sensing and monitoring apparatus 10 of the disclosure may be attached to the skin 100 of a user, and may be used to sense and monitor glucose levels and their effects on the body. Likewise, along with the systems herein disclosed the effects of glucose on the body may not only be observed, they may also be managed to prevent and/or ameliorate the onset of adverse conditions such as hyperglycemia, pre-diabetes, diabetes, and the like. For instance, the raw collected and/or preprocessed (or processed) read data may be transmitted to a computing system 70 of the system 1, whereby the data may be further processed and/or displayed so that a user may view and track the data over time, such as through a biomolecule monitoring client application 80 running on their mobile device 78, as shown. See also FIGS. 7 and 8. Likewise, in view of the analyzed data, the system may give practical guidance to the user so as to better manage the one or more states, e.g., diabetes, identified.

Figure 7:
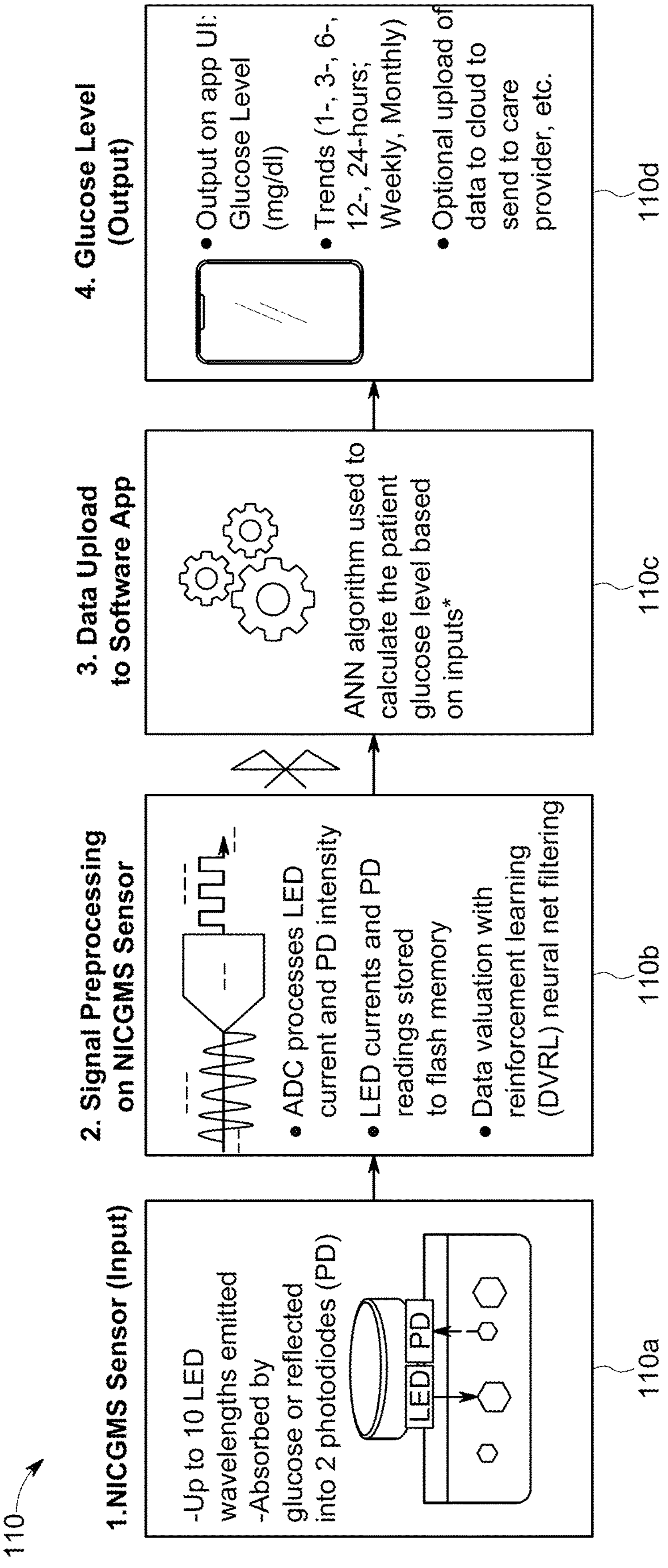
FIG. 7 depicts an exemplary process of the disclosure for sensing and communicating sensed information as illustrated in FIG. 4B or 5E.
Figure 8:
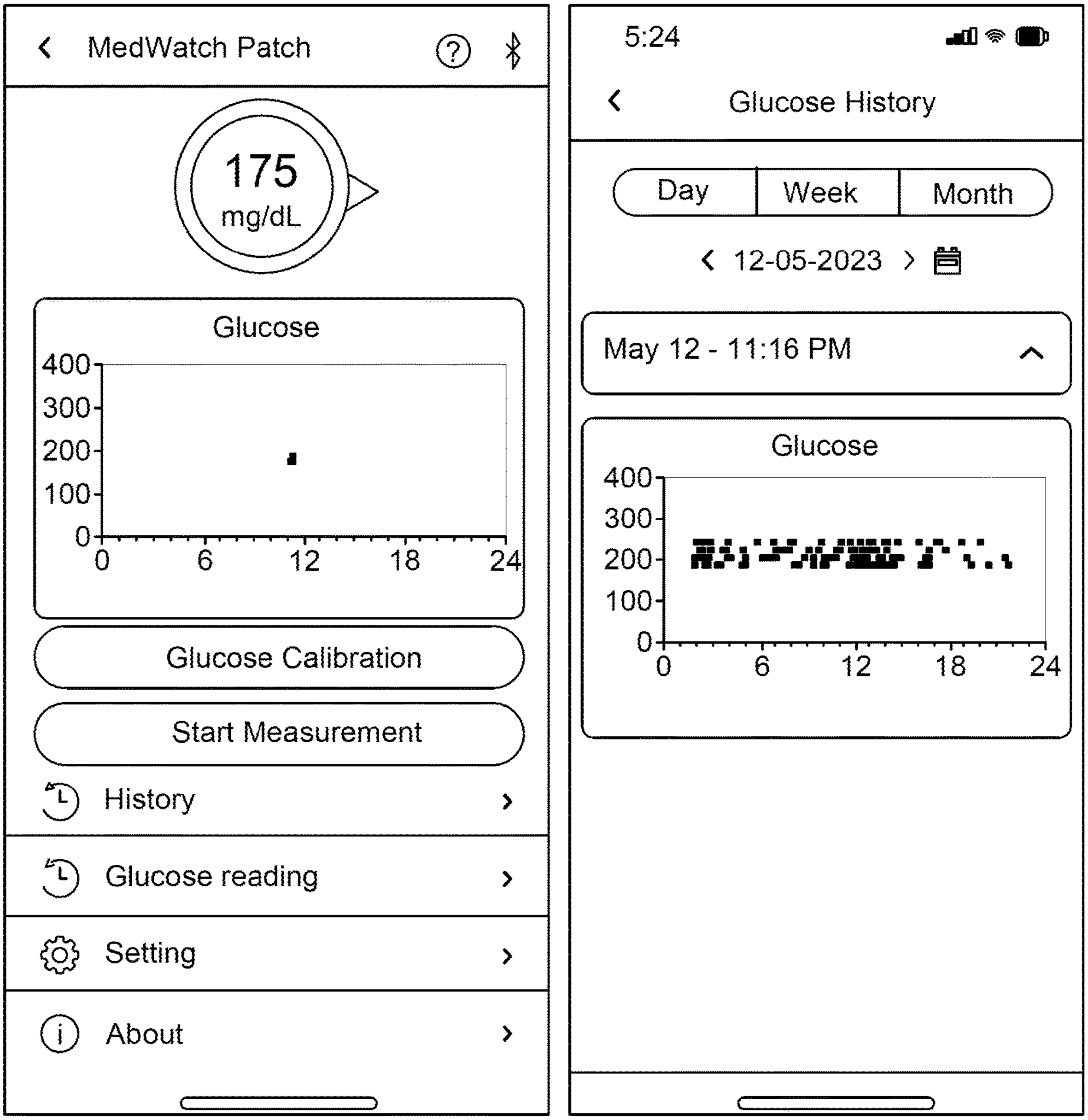
FIG. 8 depicts an exemplary graphical user interface of the disclosure, being presented at a display screen of an exemplary mobile computing device of the disclosure.

Consequently, in view of the above, the methods herein disclosed generally include placing the biometric sensing and monitoring apparatus, such as set forth in FIG. 2B or 5A onto a body part, such as an arm, as set forth in FIG. 6A, and then employing a sensor 15 of the device to collect data on the user. In this case, as can be seen with respect to FIGS. 4B and 5D, the data may include light measurements of interstitial 104 and/or blood 106 glucose values. These measurements may then be analyzed by a computing system 70 and one or more characteristics of glucose are determined and calculated, such as an interstitial and/or blood glucose level, e.g., concentration, of the user. As described in greater detail herein below, these analyses and calculations may be performed by analytics system 71 such as including an AI module 72, for instance, implementing a machine learning and inference generating method based on the collected spectral data. The results of the analysis may then be outputted, such as via a mobile computing device 78 of the user, as shown in FIGS. 7 and 8. In various embodiments, the output may also be to a healthcare professional, whereby together with the user, compliance and health may be maintained and tracked over time.

Accordingly, in some implementations, the method may include detecting and measuring the values and levels of biomolecules, such as glucose, within the interstitial fluids 104 and/or blood 106, whereby the steps may include: emitting a first light at a first wavelength, a second light at a second wavelength, a third light at a third wavelength, a fourth light at a fourth wavelength, a fifth light at a fifth wavelength, a sixth light at a sixth wavelength all the way up to ten or more lights of ten or more wavelengths being emitted, such as from one or more arrays of one or more photoemitters. In particular embodiments, the emitter of the light may be from one or more light emitting diodes. Likewise, the method may further include receiving at least a portion of the first light being reflected back from the skin of the user, at least a portion of the second light being reflected back from the skin of the user, at least a portion of the third light being reflected back from the skin of the user, at least a portion of the fourth light being reflected back from the skin of the user, at least a portion of the fifth light being reflected back from the skin of the user, and at least a portion of the sixth light being reflected from the skin of the user, all the way up to receiving ten or more lights of ten or more wavelengths being reflected back and collected, such as from one or more arrays of one or more photoreceivers. In particular embodiments, the receiver of the light may include one or more photodiodes.

Further, once the light data has been collected the method may include determining a first reading corresponding to the amount of the first light being absorbed and/or reflected back by various components within the interstitial fluid, blood and/or within the skin, and a second reading corresponding to the amount of the second light being absorbed and/or reflected back by various components within the interstitial fluid, blood and/or within the skin, and a third reading corresponding to the amount of the third light being absorbed and/or reflected back by various components within the interstitial fluid, blood and/or within the skin, and a fourth reading corresponding to the amount of the fourth light by various components within the interstitial fluid, blood and/or within the skin, and a fifth reading corresponding to the amount of the fifth light being reflected back by various components within the interstitial fluid, blood and/or within the skin, and a sixth reading corresponding to the amount of the sixth light reflected back by various components within the interstitial fluid, blood and/or within the skin. These steps may be repeated for all light of all wavelengths being emitted into the skin, reflected back from the interstitial fluid, blood and/or within the skin, and received by one or more light receivers. Once the light data has been received, it may be analyzed by a computing system of the system so as to calculate one or more levels of one or more biomolecules within the tissues and fluids thereof, from which one or more states of the user of the apparatus may be determined, and/or one or more remedial actions may be suggested.

In particular embodiments, the biomolecule sensor and/or monitor 15 may include a processing module 45 including one or more processors, such as a plurality of processing elements 47, e.g., forming one or more processing engines 46, which may be coupled to or otherwise be associated with the plurality of energy emitters and energy sensors for collecting data therefrom. In such an instance, the on-board processing module 45 may be configured for one or more of pre-processing and/or processing the raw light and/or read data, and in some instances may calculate a first iteration of a biomolecule value calculation, such as including one or more of the presence, concentration, and/or activity of the biomolecule within the tissue. However, in other instances, these calculations may be performed, or may be continued to be performed, such as by an off-board computing system 70. Hence, in certain instances, the sensor unit 18 itself, or an associated computing system 70 associated therewith, may be configured to determine the presence and value of biomolecules, such as glucose, and the processing unit 45 and/or associated computing system 70 may be configured for determining tissue (or interstitial space) and/or blood glucose levels, e.g., based on the collected data. In certain instances, the processor module may be adapted to calculate or otherwise determine glucose (or other biomolecule) values, e.g., levels, concentrations, and the like, over time, such as using machine learning, e.g., based on collected and the user's historical health data.

Further, in various instances, to better determine biomolecule levels and/or states of the individual, e.g., with respect thereto, the continuous biomolecule monitoring apparatus 10 and/or device 15 may be associated with an external computing system 70, such as where the computer system 70 implements an artificial intelligence module 72 that is configured for receiving the raw sensed data, e.g., reflected light data, raw read and/or digital read data, pre- and processed data, and/or other associated data, which, once received by the computing system 70 may be analyzed, and once analyzed, a biomolecule value, level, concentration, and/or one or more other characteristics, may be calculated and determined. From the results of the analysis of this data, one or more states of the individual may be assessed. For instance, the Artificial Intelligence (AI) module may include a machine learning engine and/or an inference engine, such as where the machine learning engine is configured for training the system, and the inference engine is configured for making a prediction based on such training.

In such an instance, one or both of the machine learning and inference engines can be embodied by a data structure, such as including an Artificial Neural Network (ANN). Once the continuous biomolecule monitoring device is positioned and secured next to the skin, such as illustrated in FIGS. 4A-4B and/or 5D-5E, an internal mapping, called a signature, can be performed so as to identify the active region wherein measurements from the device will be taken. Specifically, in specific embodiments, performing the initial signature analysis may result in one or more neural net assessments of the topology of the skin.

Once the mapping has been performed, readings can be taken in a uniform manner. This uniformity is important because even a 1 mm movement of the device can cause the readings to be off, which can have devastating effects to a wearer who is using and relying the device to monitor and control their blood glucose levels. When secure, the topology continues to be relevant, and the measurements are appropriately accurate based on that topology. If the device is subsequently moved, then a new topology mapping can be performed, or the effects of the movement may be corrected mathematically by the AI module. The patch configuration, as represented in FIGS. 3B and 5B are configured to overcome this problem by localizing the device to a specific location, allowing the signature to be performed and the topographical map to be generated. Once the topology has been mapped, then a plurality of measurements may be taken, as described herein.

As presented in the embodiments of FIGS. 2B and 4A-B, the biometric sensing and/or monitoring device 15 may include a sensor unit 18 that includes a plurality of sensor arrays 20*a* and 20*b*. As depicted, the first array 20*a* includes six energy emitters 22*a-f*, and the second array 20*b* includes four energy emitters 22*g-j*. In particular implementations, the energy emitters 22 are composed of light emitting diodes. Likewise, each sensor array 20*a*, 20*b* includes one or more energy receivers 23*a* and 23*b*, such as at least one photo receiver. This dual array configuration is useful because it allows for a wide range of light waves to be emitted in sequential or other determined order, and thus allows for a large number of spectral data to be generated and analyzed. However, in other instances, as depicted with respect to FIGS. 5A-5E, a photoplethysmography (PPG) sensor array may be included, or may be substituted for one or more of the arrays 20*a* and/or 2*b*.

For instance, as can be seen with respect to FIG. 5A, in one embodiment, the sensing and monitoring device 18 may include the six-emitter, 1 photodiode sensor array 20*a* as depicted in FIG. 2B. However, in this embodiment, the four-emitter, 1 photodiode sensor array 20*b* has been replaced with a PPG sensor 35, as explained in greater detail herein below. It is noted that in the embodiment of FIG. 5A the sensor unit 18 further includes a number of other electronic components 60. In that regard, although such electronic components 60, as described below are with reference to the embodiment of FIG. 5A, any of these components may be included in addition to, or substitution for, any of the components set forth with regard to FIG. 2B.

Consequently, the substitution of a PPG array 35 for the four-emitter array of 20*b*, will allow for a variety of different data to be considered when taking the measurements, analyzing the results thereof, and when making the determinations recited herein. Specifically, as discussed above, use of one or more arrays of photoemitters, such as 3, 4, 6, 8, 10, 20, 30, 50, or more, is useful for generating a broad spectrum of visual, e.g., reflectance, data that can be produced by directing light of a plurality, e.g., 5, 10, 20, 30, 50, of different wavelengths into the skin. However, light of such wavelengths can be generated and emitted from a plurality of different emitters, which can all be miniaturized and positioned on a single array, e.g., 20*a* (or 20*b*). In addition to the photoplethysmography (PPG) array 35, as can be seen with respect to FIGS. 5A-5B, a second array, e.g., 20*b* (or 20*a*), may also be included, such as where the second array may be included in addition to a photoplethysmography (PPG) array 35.

Having these two arrays, e.g., a photo-array and a PPG array, together, is useful because they produce different data at different depths of the skin. Generally speaking, the photo-array produces skin reflectance data, which may be indicative of the presence of one or more biomolecules of interest, whereas the PPG array produces additional data pertaining to the heart and cardiac activity as well as the response of the skin thereto, which again may be affected by the presence of the biomolecules of interest under observation. These two different sensor configurations, therefore, collectively produce a more holistic view of what is going on within the tissues and how the body they are responding to the presence of various different biomolecules. Specifically, the resistivity of the skin and/or vessels, in the presence of biomolecules within the interstitial fluids and blood, during the cardiac cycle, produces a wealth of spectral data that can be analyzed and used to determine the characteristics of a number of biomolecules. This data can be used to generate a pulse-wave-velocity analysis by which cardiac function and/or vessel health may be assessed. Other cardiac relevant measurements and data can also be generated.

However, as can be seen with respect to FIGS. 2A and 5B, an important feature of the devices disclosed herein is the miniaturization of the various components of the arrays 20 and electronics 60 of the sensor device 15, as well as their arrangement on a single or double-sided printed circuit board 42. This arrangement is unique and useful because it allows for the form factor of the sensing and monitoring device 15 to be as small as possible, while at the same time as encasing the electronics 40 and componentry 60 necessary for taking a broad range of measurements so as to more accurately determine the presence and effects of biomolecules in the body. Hence, the various different components of the device have been designed to occupy a very compact internal space within the housing.

That being the case, the various electronics 40 and components 60 may be positioned on both sides of a double-sided printed circuit board 42, and may be run from a single or double power supply 48, which may be positioned on one side of the one or double-sided printed circuit board 42, while the other side of the double-sided printed circuit board 42 may include sensor arrays 20*a* and 20*b* and the other electronic components of the device. For instance, in various instances, the one or more electronic components 60 may include one or more sensor arrays 20, PPG sensors 35, galvanic skin response sensors 69, analog to digital converters 41, one or more processing modules 45, a communications module 43, temperature sensor 64, as well as one or more auxiliary electronic devices, including: an accelerometer 61, gyroscope 62, $SPO_2$ assembly 63, EKG electronics module 66, and the like. As shown, all of these components can be optimized for size and concisely arranged to be snuggly fitted within the housing.

For instance, similar to the embodiment set forth in FIG. 4B, the sensor unit 18 of FIG. 5A includes an electromagnetic energy emitting array 20*a* that includes a number of energy emitters 22 and a number of electromagnetic energy receivers 23, such as including one or more photodiodes. So being, like the sensor unit described with reference to FIG. 4B, the non-invasive, continuous biomolecule monitoring and sensing unit 18 of FIG. 5A may include a series of photo arrays 20*a*, 35 that direct visible, near infrared, and/or infrared light at the skin in a pattern of different light frequencies, intensities, and/or durations using the photo-light/PPG arrays. For example, one or more of the light array(s) may include one or more light emitting diodes (LEDs) and/or light receiving diodes, photodiodes. In various embodiments, the one or more photo arrays, e.g., 20A, may include 1, 2, 3, 4, 5, 6, 7, 8, 9, 10, 11, 12, 15, or 20, or even 30 or more (including numbers therebetween) photo emitters 22 and/or photodiodes 23, where each photo emitter 22 emits light and each photodiode 23 receives light, of a same or different wave length, sequentially or in a determined or random pattern, such as in a pulsing manner, where the durations may be the same or different, as described above with reference to FIG. 2B.

Particularly, in the iteration of FIGS. 5A and 5B, a first photo-array 20*a* of photo emitters may be included, such as where the photo-array includes a number of LEDs from 3, 4, to 5 to 6 up to 10 or more LEDs, such as where the photodiodes of the photo-array may include from 1 to 3, 4, up to 10 or more photodiodes. As depicted, the photo-array 20*a* includes 6 LEDs, but it could easily include up to 10 or more LEDs, which are positioned on a single array 20*a*. In other instances, however, the 6 to 10 or more LEDs may be distributed throughout two or more arrays, as shown in FIG.

2B. In this regard, as depicted the photo-array 20*a* includes 6 photoemitters, such as where the series of emitters includes a first, second, third, fourth, fifth, and sixth light emitting source, e.g., LEDs, such as where each light source emits light of a different wavelength. For instance, the 6 LED light array may be configured for emitting light of: a first wavelength, which may be about 1000 to about 1200 nm, or less, light of a second wavelength, which may be about 1300 nm more or less, light of a third wavelength, which may be about 1450 nm or more, light of an fourth wavelength, which may be about 1500 nm more or less, light of a fifth wavelength, which may be about 1550 nm or more, and/or light of a sixth wavelength, which may be about 1650 nm or more. In some embodiments, any one of the light sources may be an LED, and the wavelength of the emitted light may vary by +/−about 10-25 nm, about +/−50 nm, about +/−100 nm, and the like.

In various instances, along with the 6 LED light array, an additional 4 emitters may be included, such as on the same 6 LED array, making it a 10-emitter array, or the additional 4 emitters may be included, such as on an additional array, e.g., 20*b*, such as shown in FIG. 2B. In either instance, the additional 4 photoemitters may include a first, second, third, and fourth light emitting source, where each light source emits light of a different wavelength. For instance, the 4 emitter-array may be configured for emitting light of a first wavelength, which may be about 550-60 nm or more, light of a second wavelength, which may be about 650 nm more or less, light of an third wavelength, which may be about 850 nm or more, and light of a fourth wavelength, which may be about 940-50 nm more or less. It is to be noted, that any mixing and matching of emitters in differing combinations is permissible, and certain emitters may be omitted. In various instances, the one or more photo-arrays may include 10 emitters or more, 9 emitters, 8 emitters, 7 emitters, or less, and in any of these instances, the arrays may be separated into 2, 3, or 4 or more groupings of emitters emitting the same or different wavelengths. In various embodiments, a pulse photoemitter may be included, such as where the pulse photoemitter is configured to emit a first light at a first wavelength and a second light at a second wavelength, a third light at a third wavelength, a fourth light at a fourth wavelength, a fifth light at a fifth wavelength, a sixth light at a sixth wavelength, and so on, which lights may be emitted from the same or different photoemitters, from the same or different arrays.

Likewise, as described above, along with a series of one or more light emitter arrays 20*a* and/or 20*b*, each sensor unit 18 may further include one or more light sensors 23, such as one or more photodiodes. For example, each sensor array 20 may include one or more, e.g., two, photodiodes, such as a first photodiode that is configured for receiving and detecting light waves in the range of about 1000 nm-1700 nm, and/or a second photodiode that is configured for receiving and detecting light waves in the range of about 500 nm-to about 1100 nm. However, although two photodiodes have been described, only one or more than two may be included, such as three or four photodiodes, where each photodiode is attuned to sensing wavelengths equally split between 500 nm-1700 nm. In other embodiments, five or six or seven up to ten or more photodiodes may be included, such as where each photodiode is attuned to its own dedicated photoemitter wavelength.

In addition to the above, as set forth with respect to FIG. 5C, an additional array 35 may also be included, such as where the additional array is configured as PPG array 35. In various embodiments, one or more of the above-mentioned arrays may be omitted. The PPG sensor 35 may include an electromagnetic radiation emitter array 36 and an electromagnetic radiation receiver 37, which in this instance may be arranged linearly, e.g., in a lateral line, in relation with one another. In this regard the photoemitter array 36 may be composed of three emitters, such as LED emitters, which are configured for directing light into the tissues of the body. In a particular iteration, the three-emitter array 37 may be configured for emitting light of one or more of a green, red, near-infrared, and/or infrared wavelength, such as where at any given time the three LEDs 36*a-b* emit light of different wavelengths. However, the emitter 36/37/receiver array may include any reasonable number of emitters and receivers, deploying any suitable wavelengths for emission and collection.

One or more converters may also be included, such as an analog to digital converter 41, for instance, where the converter is configured to pre-process photoemitter currents and/or photodiode intensity analog data, e.g., raw reflected electromagnetic radiation data, and convert them into digital data. In various embodiments, the converter may be a two-way analog to digital, and digital to analog converter. Further, in various embodiments, a storage-devices 76, such as a flash storage, or other memory device, may be included, such as for the on-board storage of data, such as photodiode currents, photodiode readings, and the like. In certain instances, a PCBA 42 may be included, and all of the components may be powered by a power source 48, such as a rechargeable lithium-ion battery, which may be adapted to allow for "quick charging." In such instances, the battery 49 may be recharged quickly, e.g., within 20-30 minutes, so as to fully recharge the battery, which battery may be of a capacity to last up to 7, such as 14, such as 21 days, up to about 30 or more days, e.g., per wear period. In certain embodiments, the power source 48 may be configured for wireless charging, e.g., conductive or inductive charging, and thus, the power source 48 (as well as one or more of the emitters) may include or otherwise be associated with an antenna array including one or more antennas.

Particularly, as can be seen with respect to FIG. 5A, in various embodiments, the sensor unit 18, specifically, the electronics module 40, may further include a number of other components, such as a temperature sensor 64, and/or thermistor, an accelerometer 61, and/or gyroscope 62, $SPO_2$ assembly 63, such as for collecting temperature, oxygenation, and/or movement data of the wearer. The inclusion of a temperature sensor 64, is useful for allowing the sensor to monitor the temperature of the skin under, e.g., at the surface of, the sensor. For example, skin temperature data is useful for determining a reaction of the skin, e.g., with respect to its resistivity, in view of both the biomolecule of interest as well as the experienced temperature. In various embodiments, an electronic or digital shutoff may be included, so as to ensure the skin temperature does not exceed 42° C., such as for 8 hours or more, so as to warn the user of any excessive thermal exposure.

Accordingly, as can be seen with respect to FIG. 5A, the non-invasive, biometric sensing and measuring device 15 may be configured as an all-around sensing and monitoring apparatus 10. For instance, in particular embodiments, the sensing and/or monitoring device 18 may include a plurality of sensing devices, in any combination as described above, for generating a number of sensed data that may be considered when determining characteristics of one or more biomolecules as well as the conditions of the body. Particularly, as can be seen, the sensing device 18, may include one or more sensor arrays, such as including a first sensor array 20*a* including a plurality of photoemitters and photodiodes, as described above, and a second sensor array 35, which is composed of a photoplethysmography (PPG) sensor.

For example, as set forth above, one or more of the four or six emitter arrays, as depicted in FIG. 2B, may be removed and, may be replaced with a photoplethysmography (PPG) sensor 35, as depicted in FIG. 5A. Particularly, as depicted, a PPG array 35 has been substituted for the four-emitter sensor array 20*b* of FIG. 2A. Including a PPG sensor 35 in addition to a photo-array, such as the six-emitter photo-array 20*a* of FIG. 2B, is useful because it allows additional sensed data to be obtained and considered when determining a value of a biomolecule under consideration. In this embodiment, the six-emitter photo-array 20*a* is useful for detecting the presence of and a value of a biomolecule of interest, whereas an addition of a PPG sensor array 35 may be useful along with the six-emitter array 20*a* for determining changes in skin resistivity caused by the presence of glucose in the interstitial fluid. Further, the PPG sensor 35 may further be useful for detecting and/or determining a change in fluids, such as the change in flow and/or blood volume, e.g., caused by the pressure of circulating blood, for detecting element of the cardiac cycle, and for determining pulse-wave value, and the like. Additionally, in particular embodiments, the PPG sensor may be included as an addition to the above referenced four 20*b* and six 20*a* emitter arrays of FIG. 2B. In any of these instances, the PPG sensor 35 may be configured as a miniaturized, solid state electronic sensing device that reads reflected light data and in response thereto generates a PPG readout that can be used for performing improved biomolecule, e.g., glucose, calculations. In this regard, the PPG generated data is useful for determining physiological health and/or pathological conditions of the cardiovascular system, both of which are further useful in determining an accurate value of biomolecules, such as glucose, within the blood and/or interstitial spaces.

Hence, in many instances, it is useful to include a PPG sensor array 35 in addition to one or more of the 4 or 6 or other photoemitter/one or more photoreceiver arrays, as described herein. For instance, as can be seen with respect to FIGS. 5A, 5B, a sensor unit 15 may include a plurality of sensing devices 20, 35 for collecting a plethora of bodily information, all of which may be considered when determining the presence and effect of various biomolecules within the body. These sensing devices, as set forth with respect to FIG. 5A, are illustrated in an exploded configuration in FIG. 5B, so as to better see how the configuration of the layout may be assembled together. This layout is important because it has been optimized so as to be in a very small form factor, such as for ease and comfort of wearing for a prolonged period of time.

As can be seen, a central feature of the sensing device 15 is a six emitter, single receiver sensor array 20*a*. As depicted, this array includes six emitters, 22*a-f*, but can include more or less emitters. Likewise, the emitters may be configured for emitting any suitable wavelength of light, such as one or more of those set forth herein above. One or more photoreceivers 23 may also be included for detecting and collecting the wavelengths reflected from the skin after emission by the one or more emitters. In particular embodiments, the wavelengths of the photoemitter array may be configured as a glucose sensor array having photoemitters and photodiodes that are configured for detecting and/or determining glucose values and its effects on the body.

To better determine glucose and/or other biomolecule values, and body responses thereto, a number of other sensor values may be detected and used to perform one or more of the calculations described herein throughout. For instance, the sensor unit 18 may additionally include a temperature sensor 62, as well as a galvanic skin response sensor 69*a*, 69*b*. These sensor devices are useful for determining both the condition of the body at the time of measurements, such as skin temperature and/or resistivity, so as to better determine a baseline condition of the wearer, but are also useful for better determining the presence of various biomolecules within the body as well as their effects thereon.

As indicated, a PPG sensor device 35 may also be included, such as for detecting biomolecules that are positioned deeper within the body, such as within the interstitial spaces, deeper within the tissues, and/or within the blood and vessels. Data collected from this PPG sensor, therefore, will allow the analytics system to consider a wider variety of variables, such as blood glucose values, oxygenation, blood flow, pulse rate, pulse duration, pulse periodicity, blood volume, expansion and contraction of the vessels, such as during a cardiac cycle. All of this data may be collected and used to define an entire cardiac cycle and/or overall breathing experience, all of which can be used to determine both the presence of biomolecules within the tissues, vessels, and fluids therein and between. Additionally, as indicated above, collected cardiac relevant sensor data can be used to generate a pulse-wave-velocity analysis by which cardiac function and/or vessel health may be assessed. Other cardiac relevant measurements and data can also be generated.

As can be seen with respect to FIG. 5C, the PPG sensor 35 may include an electromagnetic radiation emitter array 36 and an electromagnetic radiation receiver 37, which in this instance are arranged linearly, e.g., in a lateral line, in relation with one another. But, in other instances, the configuration of emitters and receiver, may be arranged differently such as where the emitters 36 at least partially surround the receiver 37, such as in a circle, semi-circle, square, triangle, and the like. Consistent with the iterations above, the emitter/receiver array 35 may include any reasonable number of emitters 36 and receivers 37, deploying any suitable wavelengths for emission and collection.

However, in particular embodiments, the PPG sensor 35 may include three photoemitters 36 and at least one, but up to three, or more, photoreceivers 37. Particularly, as depicted, the photoemitter array includes three electromagnetic radiation emitters, 36*a*, 36*b*, and 36*c*, which can be configured to emit one or more of a visible, near-IR, or IR light wave. Nevertheless, in particular embodiments, the electromagnetic radiation emitters 36 are configured for emitting light within the green, red, near- and/or infrared spectrum, and likewise, one or more photodiodes 37 may be included to detect and receive reflected light within the ranges of the green, red, near- and/or infrared spectrums.

Accordingly, as can be seen with reference to FIGS. 5C and 5D, the PPG sensor 35 may include one or more, e.g., a plurality, of low intensity green, red, near- and infrared light. In certain instances, the electromagnetic radiation emitters may be high intensity green and/or red, e.g., near-infrared or infrared, LED light emitters. Specifically, in various embodiments, the PPG sensor 35 may include one or more photo-emitters, 36*a*, 36*b*, and 36*c*, e.g., LEDs, that are configured for emitting light of a wavelength so as to fall within the green spectrum, as demarcated by the vertical hashmarks in FIG. 5C, and further includes one or more photo-emitters that are configured for emitting light of a wavelength so as to fall within the red to infrared spectrum, as demarcated by the horizontal hashmarks. In such instances, the photoemitters may be cycled so as to emit a combination of various lights within the green spectrum, various lights within the red spectrum, as well as various lights within the near and/or infrared spectrum, such as collectively, e.g., all at once, or sequentially.

Further, as depicted, the PPG sensor 35 includes one or more photoreceivers 37, such as a photodiode, for receiving the emitted light waves. In various instances, the photoreceiver 37 may be adapted for collecting and detecting light in the green, red to infrared light being reflected back from the tissues and vessels. Through the continual irradiation of the underlying tissues with green and red-infrared lights, e.g., from respective photo-emitters, the light may traverse through the skin and the change in fluid volume, e.g., in the tissue and/or vessels, may be determined, such as by measuring the difference in the amount of light either transmitted or reflected and/or refracted back to the photodiode 37.

For instance, since light is more strongly absorbed by blood than the surrounding skin tissues, the changes in blood flow can be detected by the photodiode(s) by the changes in the spectral array and/or intensities of the lights being reflected back from these respective structures. More specifically, with every cardiac cycle, the heart pumps blood to the periphery, which cardiac action causes a characteristic change in the skin and vessels as the blood is pumped through every particular tissue. The pumping of the blood through an area causes a pressure pulse to be transmitted through the vessels, which causes the distention of the arteries, arterioles, capillaries, and surrounding tissues. This pressure pulse is the result of a greater volume being pumped from the heart to the periphery, which pulse distends the vessel walls and surrounding tissues, which in turn, causes a concomitant change in the skin, which can be detected optically.

More particularly, as employed herein, the PPG light signal has several components from which signals several different metrics may be determined, including: volumetric changes in arterial blood, e.g., which is associated with cardiac activity, variations in venous blood volume, which modulates the optical signal, and an AC and a DC component can also be observed. This spectral determined data shows the tissues' optical properties and allows subtle energy changes in the body to be determined. Further, because the skin is richly perfused, the pulsatile component of the cardiac cycle can be determined through reflection, such that the DC component can be determined, e.g., by bulk absorption within the skin, while the AC component may be determined by the variation in blood volume caused by the pulse. From this data the systolic and diastolic, e.g., AC/DC, phases can be determined. As indicated, from this data, both blood oxygenation and cardiac events, e.g., heart rate, can all be determined. Further, as indicated, from this cardiac data a pulse-wave-velocity analysis can be performed by which cardiac function and/or vessel health may be assessed. Other cardiac relevant measurements and data can also be generated.

As can be seen with respect to FIG. 5A, one or more of the photo-emitters and/or photo-receivers 36, 37 may be surrounded by a light blocker so as to prevent electromagnetic radiation from an emitter 36 impinging into the photoreceiver 37 and thereby interfering with the reading of light reflected back from the tissue being monitored. For example, in various embodiments, the light blocking element(s) may be configured as an opaque, e.g., black or white, light dam that can surround the photo-emitter(s) 36 and/or photodiode 37, and functions to absorb and/or prevent light being emitted from the photo-emitter from invading into the photodiode 37 such that only light reflected back from the skin is allowed to hit the photodiode. The light dam may be of any suitable configuration and of any suitable material, such as metal, rubber, foam, although a metal, e.g., aluminum, material may perform better than foam, e.g., because it is less transparent to IR light impingement in that it absorbs and does not refract or allow it to pass through.

Further, as can be seen with respect to FIG. 5B, the sensing and/or monitoring device 18 may additionally include a number of other electronic components 60, such as for generating additional data that may be relevant to more accurately determine biomolecule values and/or their effects on the body 100 and the body tissues, as seen in FIG. 6A. For instance, the sensing and monitoring device 18 may include a temperature sensor 64, such as an infrared temperature sensor, for determining the temperature of the skin and body. Likewise, along with determining skin temperature, it may be useful for further determining skin moisture levels, and so a moisture sensor, such as a galvanic skin response sensor 37 may also be included. Furthermore, one or more of the sensing devices, and other components 60, may be associated with one or more PCBs 42, all of which may be contained within the housing 17. In such an instance, one or more of the devices may be covered by a glass window 21 in the bottom casing member 17*b* of the housing 17, and in certain instances, the window, as all windows referenced herein, may be plastic or glass and may be coated with an anti-reflective coating, so as to increase the signal to noise ratio.

Furthermore, as can be seen with respect to FIGS. 5D and 5E, provided herein is a non-invasive, continuous sensing and/or monitoring biomolecule detection device that is configured to be positioned on the skin of a body of a user of the device, e.g., a wearer, such as an arm, leg, or back of the user, in a manner such that light, e.g., green, red, near, and/or infra-red light, which as depicted in FIGS. 5D and 5E, may be emitted and directed into and through the skin. In particular implementations, as can be seen with respect to FIG. 6A, the sensing and/or monitoring device may be associated with a framework member 14, e.g., dome, and/or attachment structure 12, such as to form a patch 11 that can be positioned on the body 100, such as on the back of the arm between the shoulder and the elbow.

Specifically, as described herein, in various embodiments, the sensing and monitoring device 15 may be configured for continuous biomolecule monitoring, such as up to 1, 2, 5, 10, 14, 21, or 28 days or more, and for these purposes, the device may be attached to the body, e.g., via a patch or wristband structure, at an active site for a prolonged period of time for observation, detecting, and sensing. As can be seen with respect to FIGS. 5D and 5E, once securely attached to the body, so as to virtually be immobilized thereon, a first step after attachment of the biometric sensing and/or monitoring device 10 may be to run a calibration protocol so as to calibrate the device to the particular user at the particular position the device is applied to the body. Such a calibration and/or signature, may be performed by running a routine, which routine may be implemented by one or more processors 45 of the device, which processor(s) may control the energizing and activation of the photoemitters 22, 36, e.g., of the photo-sensor 20 and/or PPG 35 arrays, as well as configuring the photodiodes 23, 37 to receive reflected light waves back. In particular implementations, an on-board or off-board processor 45 may control the sequence, pulsing frequency, duration, and intensity of the photoemitters, in accordance with the generated calibration protocol, such as by directing one or more micro-controllers configured to control each of the elements of the sensor.

Such calibrations may be performed so as to map the internal constituents underlying the tissue upon which the sensing and monitoring device is placed. This mapping may be of cellular structures or fluids within or around those structures, or may simply be a signal of a pattern of reflectance with respect thereto. In certain embodiments, the mapping may be of biomolecules, such as glucose, contained therein. Specifically, in particular embodiments, the mapping may be of the reflectance patterns emitted and received by the sensor arrays. Once calibrated, the device may then be configured for sensing biomolecules, such as glucose, and determining their characteristics, such as by taking a number of readings, e.g., measurements, periodically, such as every 5, 10, 15, 20, 30 minutes and/or more, such as every hour 2 hours 4 hours, 8 hours, or 12 hours or more, such as every day.

Once calibrated, the device 15 may then implement in an emittance protocol by which to illuminate the skin and the components therein, in a number of different patterns, so as to detect and determine the presence and values of various biomolecules within the skin, which can be mapped over time, along with the various physiological factors that characterize the body at the time the measurements are taken. As described herein below, all of this data may be fed into a data structure generated by the analytics system whereby a holistic mapping of all factors can be generated, and correspondences between the presence and characteristics of biomolecules within the tissue, the spectral arrays associated therewith, and the individual's physiological response thereto, can be made. And because these measurements are taken continuously, the various connections between these correspondences can be weighted. Consequently, once produced, the data structure, or other analytic framework, can then be used to determine or otherwise predict a number of different characteristic values of the biomolecules measured and/or the state of a body or its tissues in response to thereto.

Specifically, as depicted in FIG. 5E, once the sensing device 15 has been calibrated with respect to its present location on the body. One or more measurements of the underlying tissues may be conducted. In this regard, one or both of the PPG and LED array 20*a*, 35 may be energized, and the reflected light waves collected pursuant thereto may be analyzed. For instance, as depicted in FIG. 5E, right hand side, a first, photo-array 20*a* (and/or 20*b* if included) may be activated, whereby the light waves emitted penetrate to a first depth, before being absorbed or reflected. And subsequent thereto, a first set of data is collected. Then, a second, PPG array 35 may be activated, whereby the light waves emitted penetrate to a second depth before being absorbed and/or reflected, such as where the second depth is greater than the first depth, as depicted in FIG. 5E. In this manner, the biometric sensing and monitoring apparatus 10 of FIG. 5A may allow for a greater amount of data to be collected, such as because, two different spectral arrays 20*a* and 35 are employed so as to generate and collect different data. It is noted that, with respect to FIG. 5D, when activating the PPG emitters, such as for the illumination of the tissues with one or more of green and/or red to near infrared light, the activation of the emitters 36*a, b, c*, can be sequentially, or collectively all at the same time, such as for determining blood flow characteristics.

However, in other embodiments, the biometric sensing and monitoring apparatus 10 of FIG. 2B may be useful where a wider spectral array, e.g., larger range of light waves, is preferred to be detected and analyzed. Also, because more sensor devices are included in the embodiment of FIG. 5A, then in the embodiment of FIG. 2B, it will likely have a larger form factor, and thus, where a smaller design is preferred, the embodiment of FIG. 2B may be employed, but where a greater quantity of data is preferred, the embodiment of FIG. 5A may be preferred. Nevertheless, it is noted that the additional sensor units, and other componentry of FIG. 5A, can also be added to the embodiment set forth in FIG. 2B, but in such an instance, the form factor will likely be larger, so as to accommodate for the additional components.

Accordingly, as depicted in FIG. 5E, once the body tissues and underlying structures therein have been illuminated, and the data has been collected, such as from the sensing device of FIG. 2B (left hand side) or from the sensing device of FIG. 5A (right hand side), or both together, the collected data may then be pre-processed and/or processed prior to being transmitted, such as for display or for further processing. For instance, in such embodiments, the sensing device 15 may further include an output device, such as a communications module 43, such as including a communications transmitter 44*a* and a receiver 44*b*. Particularly, in certain embodiments, the communications module 43 may include a Bluetooth Low Energy (BLE) device 44, which may be coupled to the processor module 45 for outputting at least one of the sensed, calculated, and/or determined biomolecule, e.g., glucose, characteristics, e.g., levels, as well as the other collected data, e.g., raw or processed spectral data.

For example, the raw electromagnetic radiation, digital read, and/or determined results data may be transmitted to one or more of a remote server 74 and/or client computing device 73, such as a mobile phone 78, whereby the determined biomolecule levels can be reviewed by the wearer of the device, and one or more actions, e.g., lifestyle decisions, may be suggested by the system in respect thereof. Specifically, as can be seen with reference to FIG. 5E, in various embodiments, the system may include a client computing device 78 that is configured for running a client application 80, such as a downloadable mobile app that is configured for being run on the client computing device 73, through which mobile app 80 the wearer of the sensing and/or monitoring device can receive and view the determined biomolecule, e.g., glucose, results data and view trends relevant thereto, as can be seen with respect to FIG. 5E. As indicated, the sensing and/or monitoring device 15 may be configured for being coupled to a body portion of the user for a prolonged period of time, such as for 14 or more days of use, after which the sensor apparatus 10 may be removed from the body portion 100, recharged, cleaned, reapplied, and recalibrated to begin another period of sensing and monitoring.

As can be seen with reference to FIGS. 4B and 5E, the tissue in the area of the active site, where the light is impinging into the skin, includes an epithelial layer of the skin 102, the interstitial fluid 104, and the blood vessels 106, e.g., capillaries, carrying the blood and intervascular fluid. Consequently, the photo-emitters, e.g., LEDs, shine light into the skin 100, and the light penetrates through the various different layers, whereby some of the light is absorbed by each of the various different layers, and some of it is reflected back to be picked up and read by the photodiode of the monitoring device. In one implementation, it is the light that impinges into the interstitial fluid and is reflected back that is used to determine glucose levels. In this regard, the amount and/or level of reflectivity of the light back from interstitial and other fluids is dependent, in part, by the number of biomolecules, such as glucose, present therein, e.g., in the interstitial fluid and/or blood within the vessels.

Therefore, pursuant to calibration, a first pass may be performed so as to obtain a first, base level reading. Then a second, third, fourth, or more pass can be performed, and the results thereof can be compared, such as where each pass may be performed at a different depth of impingement and/or under different conditions, such as where each light being shown into the skin is emitted at a wavelength so as to penetrate into different layers of the tissue before being reflected back. In such embodiments, glucose may be present in some layers, such as in the interstitial fluid, but not present in others, such as in the epithelial cells themselves. Likewise, the photoemitter(s) of the PPG can be engaged, such as to penetrate more deeply into the tissue such as to reach into the blood vessels, wherein glucose within the blood may be detected. Particularly, the PPG emitter may be configured to emit light of a wavelength and/or intensity that goes deeper through the layers and into the blood, where it is then reflected back.

In the embodiments set forth herein, the monitoring and/or sensing devices may be configured to collect a number of sets of reflected light data from the interstitial fluids, vessels, and blood, and/or surrounding tissues, via the photo-array and PPG sensor array. All of these data points are useful because there may be biomolecules, e.g., glucose, both in the interstitial fluid as well as the blood, and light emitted from each sensor penetrates to different levels and therefore performs reads on glucose levels at the several, e.g., two, different layers. Further, as indicated above, other data may be collected and transmitted to the analytics system, such as via a wireless network connection, where such other data may include the skin temperature at the surface of the sensor as well as the galvanic skin response, which data may be incorporated as an input into the biomolecule, e.g., glucose, conversion algorithm, such as an ANN algorithm. This allows the algorithms herein to account for conditions when the user is exercising or during sensor signal acquisition as these scenarios may impact measured glucose values due to the potential effect temperature and/or skin resistivity may have on glucose spectral absorption or glucose-mediated skin response.

Accordingly, in view of the above, a mix of sensor elements is useful because it allows the analytics module to build a data structure, such as a knowledge graph, decision tree, nearest neighbor graph, an artificial neural network, and the like, whereby the various sensed and other data collected may be input and used to accurately determine various different biomolecule values, such as glucose levels and/or concentrations. Particularly, the more relevant data is entered into a data structure the better the resultant calculations will perform. For instance, in one embodiment, the data structure may be an ANN whereby the greater the amount and/or variety of data entered into the structure, the better and more accurate the calculations will be.

In this regard, having a sensor unit with a single array of emitters and receivers is useful, but in some embodiments, having a plurality of such sensor arrays may be better, and likewise, substituting, or otherwise adding, one or more of the sensor arrays with a PPG sensor adds additional utility and efficiency. Further still, further including other sensing devices, such as temperature, galvanic, motion, and other sensors, may further increase the accuracy of the predictive models being generated and/or the calculations being derived thereby. These results may be superior than having only a single photo sensing array or PPG sensor all on its own.

Consequently, marrying the photo-sensor array, e.g., for glucose measurements, together with PPG readings derived from the PPG sensor, as well as the Galvanic Skin Response and temperature data, gives a plethora of data by which the above referenced data structures, for performing one or more of the measurements and calculations discussed herein throughout. As a basic rule, the more data considered, the more accuracy there will be when employing a data structure to perform measurements, make calculations, and then better determine conditions of the body with respect to the detections and measurements made herein. In this regard, in one embodiment, the data structure may be configured as an artificial neural network (ANN) that can be employed to determine overall glucose values and conditions of the body in response thereto. Thus, accuracy of the ANN can be increased by employing a large number of data by which to perform calculations and make determinations.

Specifically, the ANN may function better in a data-rich environment that can be used to define the various different nodes in a graph-like or other structure. Hence, a feature of the system is the implementation of a data structure, such as by an AI module 72 of an analytics system 71. In some embodiments, the analytics module 71 may be instantiated on-board the sensing and monitoring device 15 itself, such as by a processing module 45 thereof, but, in other embodiments, the analytics module 71 may be remote from the device. In such instances, the electronics components 60 of the sensing and/or monitoring device 15 may include a wired and/or wireless communications module 43, such as a communications module that implements a BLUETOOTH or BLUETOOTH LOW ENERGY protocol for wireless data transmission. And, as indicated, in such instances, the data, calculations, and/or results thereof may be transmitted to a remote mobile computing device 73, such as a smart phone 78 running a client application 80 for analyzing the data and/or displaying the results thereof.

As can be seen with respect to FIGS. 6A and 6B, an important feature of the system 1 is an attachment apparatus 10 that is configured for coupling the above referenced biometric sensing and monitoring device 15 in close proximity to the skin 100 so that the calibrations and measurements disclosed herein can be taken in a consistent, uniform manner that does not change with the various movements of the body. Consequently, presented herein is a light emitting and sensing device 15 for use in continuous biomolecule, e.g., glucose, monitoring, which device 15 may be configured for being maintained in close proximity to the skin 100. In such instances, the sensing and monitoring apparatus 10 may be configured as a patch 11, or may be configured as a watch-like 90 device.

However, in the watch-like 90 instance, the determining of biomolecule, e.g., glucose, levels is computationally difficult because the watch 90 relative to the skin 100 is constantly moving as the wearer moves, and such movements may affect the light absorption and/or reflectance measurements. The analytics system 71 may make up for these difficulties computationally. Nevertheless, in other embodiments, these difficulties can be corrected for physically, such as by affixing the sensing and monitoring device 15 in proximity to the skin in a manner so that the device 15 is substantially prevented from moving, such as in a patch-like apparatus 11. Accordingly, to correct for this problem, the continuous biomolecule, e.g., glucose, monitoring device 15 may be composed such that it can be fitted within a patch 11 that includes an adhesive layer that is designed to hold the light emitting and/or sensing device 15 close to the skin 100 in a manner such that movement of the one relative to other is minimized. Such a patch-like 11 mechanisms are useful because the performing of such measurements is highly sensitive to the very specific area to which the device, e.g., within the patch, has been positioned.

Accordingly, in view of the above, provided herein is a non-invasive, continuous biomolecule monitoring device and apparatus 10 that collectively together may be configured as a wearable device 11, 90 that employs a transcutaneous biomolecule sensor unit 18 to sense and measure the spectral signals of one or more biomolecules, e.g., glucose, present within the skin. Particularly, the biomolecule sensing and monitoring device 15 is configured for generating data, such as one or more of raw electromagnetic reflected radiation data and/or digital read data that represents a spectral array of reflected light produced by the light directed into the skin from the photoemitters being received back to respective photoreceivers. These data may then be processed on- and/or off-board, such as by a computing system 70, whereby the data pertaining to the collected spectral signals may be analyzed so as to determine estimated levels and/or values of observed biomolecules and one or more conditions provoked thereby.

As discussed above, there are two main ways by which a patch-like structure 11 may be employed to hold the sensing and monitoring device 15, in close proximity to the skin 100 in an immobilized manner that prevents substantial movement. Particularly, by preventing substantial movement is meant less than 5 mm, less than 3 mm, less than 2 mm, less than 1 mm of movement. For example, the patch-like devices 11 set forth herein can prevent movement of greater than 1 mm, greater than 0.5 mm, greater than 0.1 mm. As indicated, the first patch-like structure 11 presented herein includes three general components of the referenced biological sensing apparatus 10, these include the biological sensor and/or monitoring device 15, a framework or encasement member 14, and an attachment structure 12.

In this regard, as can be seen with respect to FIGS. 3A and 3B, the biological sensor and monitoring device 15 may be received within the framework member 14, which framework member may be configured as an encasement or dome 14 into which the sensing device 15 may be snuggly and securely retained. The attachment structure 12 may be configured as circular or square-like member to which the dome 14 may be coupled, as shown in FIG. 2A. In particular embodiments, the attachment structure 12 may be at least partially composed of double-sided tape, which may be coupled to both the framework member 14 and the body 100 of the individual. As shown in FIG. 6A, the attachment structure may be configured so as to form an adhesive patch 11 that can be applied to the user's body 100 so as to position the sensing and monitoring device 15 into close proximity with the surface of the skin of an area of the body to which the apparatus 10 is to be applied. This configuration is useful in embodiments such as depicted in FIG. 2B, where the sensing and/or monitoring device 15 may have a disc-like shape and a low profile.

Hence, in various embodiments, the framework member 14 may be configured in a manner to include a low-profile receptacle, e.g., dome, into which the sensor 15 may be inserted, and may further include a flat, ledge or surface forming an attachment interface 16 to which an attachment structure 12 may be coupled, such as through a suitably configured attachment element 13, such as an adhesive, e.g., glue, as set forth in FIG. 2A. In such instances, the attachment interface 16 is more retracted, such as less than about 2 cm, less than about 1 cm, less than about 0.5 cm. In various of these embodiments, the attachment structure 12 may be configured as a patch, sleeve, band, bandage, or the like, to which the dome 14 and/or sensor unit 15 are to be coupled.

In such embodiments, where useful, an adhesive may be added to a skin contacting surface of the attachment structure 12, such as where the adhesive is biocompatible with sufficient consistency so as not to degrade too quickly over time. The materials from which the adhesive may be composed may be any fluid, tacky or sticky material capable of being associated, e.g., layered, sprayed, or otherwise be coupled with the framework 14 and support 12 members, and functions to keep them, and an associated sensor and/or monitoring device, firmly in place against the body part to which the apparatus 10 is to be attached. Where the framework member is configured as a dome 14, e.g., a circular encasement, the attachment interface or ledge member 16 may be configured as a circumferential surface that extends normal to a side-wall or bounding member of the dome so as to form an exterior lip with which the dome 14 and attachment structure 12 may be coupled together, such as by use of an adhesive. In such an instance, the ledge member may form an "L" shape with respect to the side bounding member of the cavity formed by the dome 14.

However, in other embodiments, a framework member or dome 14, along with its L shaped ledge member 16 can together function to maintain the sensing device 15 securely attached to the body 100, without the need for a separate attachment structure 12. In such an instance, the L-shaped ledge member 16 may be extended outwards, laterally away from the cavity of the dome 14 in a manner so as to form an attachment structure itself, but that is made of one-piece with the dome 14. In such an instance, the elongated circumferential surface of the ledge member 16 that surrounds the dome 14 need not simply be an attachment interface to which the attachment structure 12 may be coupled, rather, it may be the surface that gets adhered to the body directly, such as by the addition of an attachment element 13, e.g., a glue, to a sin facing surface of the attachment interface 16.

Accordingly, the attachment interface 16 may not only be extended, it may also be elongated so as to form the attachment-like structure itself. In such instances, the configuration of the elongated attachment interface 16 may have four extended and elongated, opposed sides. In certain instances, the four sides may be of equal length, so as to form a square, and in other instances two sides may be longer than the other two, so as to from a rectangle. In such instances, the sides of the attachment interface 16 may be both extended and elongated so to be about 2 cm to about 10 cm, such as about 4 cm to about 8 cm, including about 5 cm to about 7 cm in length, e.g., similar to the attachment structure 12.

Hence, in particular instances, the dome 14 and attachment interface 16 may be of a single piece, and an adhesive can be added to a bottom surface of the elongated attachment interface 16 so that the dome can thereby be coupled to the body 100 directly. Hence, in various embodiments, the ledge member 16 may not only be extended, it may also be elongated many centimetres or inches laterally away from a circumferential bounding wall forming the dome. In such instances, the elongated "L" shaped surface of the framework member 14 may form a base layer to which the adhesive element 13 may be added, such as at a bottom surface thereof so as to securely attach the elongated dome 14 to the body 100. In such embodiments as this, the framework member 14 may be a singular entity into which the sensor device is inserted.

The configuration of the framework member 14 and/or attachment structure 12 is important because, in various embodiments, part of the process of determining the effects of the biomolecule being observed on the body involves determining the changes to the body's tissues, fluids, and spaces therebetween that occur within the skin, vessels, and spaces thereof, when in the presence of the biomolecule. For these purposes, the sensor unit 16 may direct electromagnetic, or other radiation, into the skin, and may then receive reflected and/or refracted waveforms back. Specifically, as depicted in FIGS. 2B and 5A, the sensing device 15 may include a plurality of sensing arrays having a number of light emitters positioned in proximity to one or more photodiodes, such as where together a collection of emitters and receivers form an array. In certain embodiments, a dual array configuration is implemented, each having one or more photodiodes that are in line with or otherwise surrounded by a cluster of three, four, or six emitters, although eight or even ten or twelve light emitters may also be included.

As described in detail above, the emitters emit electromagnetic radiation into the skin, and the photodiodes receive the unabsorbed reflected energy back so as to generate read or spectral data. From this data, the device and/or system may formulate a map of the field of view of the observable skin and tissue spaces, such as based on the reflectance and/or refraction of various wave forms, e.g., light or sound, being directed into the observation area form which various measurements may be made. As these measurements are made repeatedly over time, so as to determine the change in the body over one or more periods, it is useful to hold the sensing unit in place for a prolonged period. Movement of the sensor unit 15 relative to its original placement of the skin, even by a small fraction, can disrupt its calibration, and throw the measurements off. Consequently, as indicated, a feature of the apparatus is a framework member 14 with or without an attachment interface 16, upon which interface an attachment structure 12 may be positioned and/or otherwise coupled, as shown in FIGS. 3A and 3B.

However, in other embodiments, as shown in FIGS. 3C and 3D, a framework member or dome 14 need not be included. Rather, in certain embodiments, all that is needed to secure the sensing device 15 to the body 100 is the attachment structure 12 itself. For example, in particular instances, the attachment structure 12 may be configured as an elongated surface member that is defined by an outer perimeter member. In such an instance, the attachment structure 12 will have both a top and a bottom surface.

Likewise, the attachment structure 12 will have both an inner portion and an outer portion. This outer portion may be defined the perimeter, which may include a single surface, such as where the attachment structure 12 has the shape of a circle, or it may include a plurality of sides, such as where the shape is a triangle, square, rectangle, and the like. Further, the attachment structure 12 may include an inner portion of the elongated surface, but where the inner portion is defined by an opening passing from the top surface to the bottom surface of the elongated surface. In such an instance, therefore, the elongated surface would also have an inner perimeter that defines the opening.

Hence, in various embodiments, as can be seen with reference to FIGS. 3C and 3D, the attachment structure 12 may be configured to include an opening, or hole, such as corresponding to the circumference and shape of the sensor device 15. In this manner, the sensor 15 may be inserted through the opening of the attachment structure 12, and together the apparatus may be coupled to body 100 so as to be held closely to the surface of skin in a manner so that the sensor unit 15 does not move relative to the skin 100. For example, such an attachment can be effectuated by the addition of an attachment element 13, e.g., an adhesive, to the bottom surface of the attachment structure. As the attachment structure 12 is configured for direct placement on the body, the material from which the attachment structure 12 and/or attachment element 13 are made should be non-toxic, biocompatible, and safe for use in contact with the body.

In any of these instances, the attachment structure is configured for maintaining a bottom surface of the sensor unit 15 in close proximity to the skin at the site of observation in a manner so that the sensor device is substantially prevented from moving. To better effectuate this positioning, in certain instances, a stiffened or otherwise inflexible attachment support 8 may also be included. In various embodiments, the support 8 may be a plurality of elongated members that extend longitudinally and/or laterally away from the inner perimeter of the attachment structure and are either integral therewith or can be added on top or beneath the surface thereof. However, in various instances, the attachment support may be formed as an attachment ring 8 that functions to provide structural support and positioning to the interior perimeter portion of the circle through which the sensing device 15 is inserted.

In particular embodiments, the attachment ring 8 may be configured to function as a mounting device, positioned so as to circumscribe the interior portion of the attachment structure 12, through which the sensing device 15 is inserted in a manner so as to be mounted with, or otherwise upon, the mounting ring 8. In such an instance, a top part of the ring may be flat, but the circumferential portion may have a thickness thereto, but with a rounded configuration. Together the flat top surface and rounded circumferential portion form a contoured center such that the hosing of the sensing device 15 may be mounted thereupon, or be otherwise engaged with in a manner that locks the sensing device 15 substantially immovably in place. In various embodiments, the locking mechanism may be a tooth in groove coupling. In other embodiments, corresponding magnets may be include, such as with opposite polarity. Likewise, together the attachment ring 8 in combination with the attachment structure 16 enables the disc-shaped housing of the sensing device 15 to adhere to a specific location on a person's arm, abdomen, buttocks, or some other part of the body.

The mounting ring 8 may be coupled to, or otherwise be formed with, the attachment structure 12 in any suitable manner such as being formed, molded, or woven therein, or glued or otherwise attached thereon. For instance, in one embodiment, the mounting ring may be threaded to a top, bottom, or circumferential portion of the attachment structure 12. This will allow the ring 8 and/or sensing device 15 to be removed from the attachment structure 12, such as for recharging and/or replacement. As indicated the entire apparatus 10, or a portion thereof, e.g., the sensing device 15, can be removed from the body at any time. To reattach the device, a new mounting ring 8 may be re-secured to, or otherwise within, an attachment structure 12 along with the sensing device 15, and collectively the assembly 10 can be attached to the body. In some instances, the mounting ring 8 may need to be threaded to the attachment structure 12 and/or device housing 17. Other attachment mechanism, as set forth herein, such as a clip, can also be used. For instance, a portion of the ring can contain clip points that match corresponding clip points in the attachment structure 12 so that the mounting ring can be clipped to the attachment structure 12. Such clips may be positioned on the side of the substrate of the attachment structure 12 rather than the bottom so as to minimize the overall height of the apparatus 10.

The attachment structure 12 may be made of any material forming a substrate to which the sensing and monitoring device 15, and in some instances attachment framework or dome 14, may be coupled, and the entire apparatus 1 can then be attached to the body. In this regard, the dome may be composed of a plastic material, such as a polyethylene terephthalate glycol (PETG). PETG is useful for forming the dome material for it efficiently prevents water exposure, such as can occur while the wearer of the patch-configured monitoring device, is working out, sweating, showering, swimming, or it is raining. Thus, the dome, when included is configured and composed of a material so as to prevent exposure of the encased sensing device from the outside elements.

In particular embodiments, the dome may be removably or permanently attached to the attachment structure 12 or patch 11, e.g., adhesive band, for positioning the sensing device in close proximity to the skin, or other base member, in a manner so as to be stably positioned thereby. However, in other embodiments, the housing 17 of the sensing and monitoring device 15 is waterproof. For instance, one portion of the housing 17, such as a top member **17*a* may have a tongue or tooth-like element, e.g., circumscribing a portion or all of a perimeter portion of the housing 17*a*, and the other portion of the housing 17, such as a bottom member 17*b*, may have a corresponding groove like-element, e.g., circumscribing a portion or all of a perimeter portion of the housing 17*b***. A compressible element, such as a foam or O-ring, may be positioned within the groove such that as the tongue fits into the groove, or channel, the compressible element is compressed, thereby forming a waterproof sealing therebetween. The housing may farther include one or more latches for securing the sealing.

With regard to the attachment structure 12, such as where a dome 14 is not included, the elongated member forming the attachment structure 12 may be composed of any suitable material, such as metal, an alloy, aluminium, titanium, plastic, acrylic, or other stiff material. However, I other instances, the attachment structure 12 may be composed of a flexible or semi-flexible material, such as made from a malleable plastic, rubber, silicone, plastic or fiberglass containing mesh, a woven blend, any other form of mesh, or may be composed of a foam material. In a particular embodiment, the attachment structure substrate may be composed of a double-sided tape such that one surface of the double-sided tape attaches to the framework member 14 and/or sensor housing 17, and the other surface is then capable of being attached to the tissue, e.g., skin, of the body portion thereby covering the tissue where the electromagnetic observation is to take place.

Regardless of the manner of coupling, the contact of the attachment structure 12 with the sensing device housing 17 to form the apparatus 10, and the attachment of the apparatus 10 with the skin should be such that it locks the sensor unit in place above the action area where the electromagnetic radiation is to be directed into the skin and the measurements are to take place. In this manner, the sensor unit may be retained within a position for sensing the presence of the biomolecule as well as for determining its levels and/or bio-activity, such as in or around the biological tissues of the action area. Accordingly, in a manner such as this, the biomolecule sensor and/or monitor may include a number of electromagnetic, e.g., light emitters, that are configured and positioned within the sensor unit so as direct visible, near infrared (NIR), infrared light, and/or other radiation, such as sound waves, into the skin on the user's tissues, such as on the back of the user's arm.

As depicted in FIG. 6A, the wearable sensing and/or monitoring device 15 may be coupled with a framework dome member 14 and/or an attachment structure 12 that may be in the form of a patch that is employed so as to attach the sensing and monitoring device 15 proximate the user's skin 100. As depicted, the sensing and monitoring device can be formed as a small circular disc having a top **17*a* and a bottom 17*b*, where the bottom includes a light transmissive area, such as an opening or window 21**, which may be formed of a transparent material, such as acrylic, and which may have one or more portions coated with an anti-reflective layer.

As indicated above, the framework member 14 may be configured as a receptacle, such as an encasement or a dome, which is configured for receiving the circular disc shaped sensing and monitoring device 15 within it. In such an instance, the dome 14, therefore, may include a circular bounding member that serves the same purpose as the mounting ring 8. Accordingly, in either embodiment, either with an encasement dome 14 or without, the apparatus should be configured so as to position the sensing device 15 within the center of the opening of the attachment structure 12, which as shown in FIG. 6A, may be configured as a patch-like attachment element 11.

As indicated, the patch 11 may be square, but in various instances, such as illustrated in FIGS. 3C and 3D, the patch may be configured as a donut, having a central opening through which the disc-shaped sensing device is inserted. In such an instance, the boundary of the opening, or a bottom side of the disc housing, may have an engagement member, e.g., a tooth or lip, so as to prevent the sensing and monitoring disc from being passed all the way through the opening. In various embodiments, once inserted through the opening in the attachment structure 12, a light transmissive layer may be covered over the opening and/or transmissive window area of the sensing device housing **17*b***. In particular instances, the transmissive layer may be a transparent sheet, which may be composed of a plastic or acrylic material. However, in various embodiments, such an additional transmissive covering layer need not be included.

In any of these embodiments, the patch 11 is adapted for positioning the retained, and/or encased, sensing and monitoring disc 15 in proximity to the surface of the skin, and ensuring that the disc device does not move relative to the movements of the wearer. This stable positioning is useful for allowing the sensor device 15 retained within the disc housing 17 to perform its calibrations and to take its measurements, such as by holding the transmissive surface 21 close to the skin 100, whereby the photoemitters within the housing 17 may then direct electromagnetic radiation into the skin, and the photodiodes may receive and analyze reflected and/or refracted electromagnetic radiation back from the skin, such as in the performance of a calibration, mapping, sensing, and/or monitoring operations.

As set forth herein, the housing 17 of the sensing and/or monitoring device 15 may be composed of two halves forming a top surface **17*a* and a bottom surface 17*b*** that can be joined, e.g., via a tongue and groove, snap, or other fitting, together to form a disc-like shape having a cavity therebetween wherein the electronics for performing the herein disclosed measurements may be retained. In various embodiments, a compressible gasket can be fitted between the two halves of the housing, so as to make the coupling waterproof. Accordingly, the top surface part of the housing may be flat with rounded sides, but having a rounded or contoured center to make space for the referenced device electronics, including a PCB (printed circuit board), rechargeable lithium-ion battery, as well as the electronic sensor components. Likewise, the bottom surface part of the housing may be a correspondingly flat-rounded disc with a corresponding contoured center. The two disc portions may have corresponding attachment mechanisms, like a tongue and groove, opposed corresponding ledge elements, e.g., "L" shaped teeth, and the like.

In the implementation depicted in FIG. 2B, the circumference of the disc is about 1 cm, about 2 cm, about 3 cm up to about 5 cm in diameter, and may be approximately 3 mm-7 mm up to about 10 mm to about 20 mm or more in height, such as where the top and bottom surfaces the housing are relatively planar or flat. However, in various embodiments, such as where the top and bottom surfaces are curved, the perimeters may be high, so as to give the disc a thin profile, such as less than 3 mm, such as less than 2 mm, such as less than 1 mm. Likewise, the length of one or more of the sides of the housing may be about 10 mm to about 20 mm, up to about 30 mm in length. Hence, the length and height of the sides may be relatively equal, so as to give the sensor device a square or rectangular shape. In other instances, where the device has a circular shape, the circumferential bounding member height may be equal the diameter, but in other instances, the perimeter height may be less than the diameter, such as substantially less than, so as to give the device the shape of a discus.

In any of these instances, the opening of the attachment structure 12, and/or the dome 14 if included, may be configured out of a flexible material, so as to conform to the contours of the disc being inserted therethrough, but may be slightly larger thereto so that the disc can be fitted snugly therein, but in a manner so as to adhere the disc to a specific location on a user's body, such as their arm, leg, back, abdomen, buttocks, or some other part of the body. This is useful because, as indicated above, a center portion of the bottom part of the disc may be a thin transparent plastic sheet, e.g., window 21, so as to allow the electromagnetic radiation to pass from the photoemitters, e.g., LEDs, mounted on a PCB encased within the housing out from the transparent plastic sheet 21 forming the bottom of the disc. The emitted electromagnetic radiation will then pass into the skin, and likewise a certain amount of electromagnetic radiation will be reflected and/or refracted back out of the skin and through the transparent plastic sheet, e.g., acrylic window 21, and into the housing. Once reflected and/or refracted back into the housing 17, the corresponding PCB 42 mounted photodiodes may then receive and read the reflected and/or refracted radiation.

Accordingly, in particular embodiments, the attachment structure 12, as set forth in FIG. 3C, may be configured so as to have an opening, such as to receive the disc therethrough. However, in various embodiments, the opening may be covered after insertion of the disc, such that a surface of the attachment structure 12 completely covers the bottom of the disc, such as where the covering is transmissive to light. In such an instance, the transmissive covering should be a circular portion that aligns with the transmissive portion or opening on the bottom surface of the disc housing 17. Such a covering can be employed to waterproof that apparatus or for sanitary reasons.

However, in various instances, the attachment structure 12 may not have a transparent plastic sheet covering the opening, but rather, may simply have an opening. In such as instance, the attachment structure may be configured so as to not completely cover the bottom of the disc. In one particular embodiments, the transmissive covering may be configured as a small circular opening portion that corresponds to the opening, e.g., about 1 cm, in the bottom portion of the disc housing 17*b*, so as to be aligned with the transmissive portion or on the bottom surface of the disc housing 17*b*. This is useful because light from the emitter passes from the disc device, through the patch, and into the skin and back without interference.

As can be seen with respect to FIG. 5B, in various embodiments, the sensor unit 15, may be configured for being pressed securely, but firmly against the skin 100. This is useful, not only for the sensor device emitting and receiving electromagnetic radiation into and from the skin, but also for collecting other data characterizing the skin, for which skin contact is beneficial or necessary. For instance, the sensing and monitoring device 15, and the housing thereof, may be configured to include a temperature sensor 64. In one embodiment, the temperature sensor may be in contact with the skin, so as to take skin temperature measurements. However, in other embodiments, the temperature sensor may be an infrared temperature sensor 64 that is configured for directing an infrared light into the skin, receive reflectance back, and from the spectral array determine skin temperature. In such an instance, the sensor may have an IR emitter and diode offset from the surface of the housing, but covered with a transmissive window, which window may have an anti-reflective coating thereon.

Likewise, the housing may be configured to include one or more skin interfacing surfaces, configured as corresponding electrodes of a galvanic skin response sensor unit 69. For instance, the galvanic skin response sensor 69 may include a first skin interfacing surface 69*a*, which may be implemented as a first electrode positioned on one side of the bottom surface 17*b* of the sensing and/or monitoring device 15, while a corresponding second skin interfacing surface 69*b*, which may be implemented as a second electrode positioned on the other side of the bottom surface 17*b*. Together the two electrodes can pass a current therebetween so as to determine the body's skin response, from which a galvanic skin response measurement may be taken, and the results thereof can be fed into the data structure, so as to give a measurement of the skins resistivity, which in turn can be used to better determine the presence of a biomolecule of interest as well as the body's response thereto.

Further, it is noted that the electrodes 69*a* and 69*b* can also be used by themselves or in addition with a pair of other electrodes 66, which may be configured as EKG electrode interfaces, 66*a* and 66*b*. In other instances, the electrodes 66*a* and 66*b* may be employed by themselves, such as for taking an EKG reading. A further set of corresponding electrodes 66*c* and 66*d* may also be included in the housing and can be used for charging the battery 49. In particular embodiments these electrodes are configured for interfacing with, e.g., contacting, the surface of the skin, whereby the various measurements disclosed herein may be made. Further, the sensor device 15 may include a communications module 43, having a transmitter 44*a* and receiver 44*b*, by which communications, such as instructions may be sent and received, and data may be transferred. In such embodiments, a communications interface may be built into the housing 17.

With respect to pressing the sensor unit 15 securely, but firmly, against the skin 100, such as for the taking of skin temperature, measuring a galvanic skin response, and/or taking an EKG reading, in such an instance, the attachment structure 12 may be a compressible, foam support member configured for being compressed when pressed against the skin by an applying force. As depicted in FIG. 3D, the attachment structure 12 may be configured so as to have a compressible donut shape. The donut shaped attachment structure 12 may have a central opening through which the sensor device housing 17 maybe inserted.

In such instances, the attachment structure 12 may include a mounting support 108 that may be positioned at the interface between an interior perimeter portion of the attachment structure 12 and the sensor device housing 17, so that the sensor device 15 can be securely mounted within the donut and be pressed firmly against the skin. In this manner, the mounting support 108 member may be configured to prevent translational movement, e.g., left to right and forwards and backwards, and yet the flexible foam attachment structure 12 may remain flexible enough to accommodate body part movement. It is especially useful that the interaction between the sensing device housing 17, the attachment structure 12, and the mounting support 108, are configured to prevent rotational movement of the sensing device. This may be due to the rigid material, shape, and configuration of the mounting support 108, such as where they have corresponding corner features that prevent rotational movement of one with respect to the other.

However, in certain instances, the form factor of the sensing and/or monitoring device 15 may not be formed as a disc member, such as to be inserted within an attachment patch 11, as described above. Rather, as set forth in FIG. 6B, the sensing and/or monitoring device 17 may be configured as a watch 90. Particularly, in some implementations, the wearable device can be in the form of a watch-configured device or may be retrofit to existing wearable technologies. In such an instance, a watch-shaped sensor device 15 can be added to the back side of a watch, by an encasement structure 94 that functions to couple the sensor unit 15 to the watch. For instance, the encasement structure 94 is configured to couple the sensor unit 15 to the back of a smart watch and/or its writs-band 96, whereby the sensor 15 can communicate with the smart watch, e.g., wirelessly, such as via RFID or BLUETOOTH LE communications protocol. Particularly, in various embodiments, the electronics of the apparatus 10 may include a wireless communications module 43, such as a BLUETOOTH, BLUETOOTH LOW ENERGY, WIFI, or other wireless transmitter.

In such instances, once collected by the sensor 15 and/or watch, the sensed data may be analyzed data and/or may be transmitted. For example, an analytics system 71 of the disclosure may be configured as an "on board" computational unit 45, which may further be in communication with a decentralized analytics module 71, such as a cloud based artificial intelligence system 72. The onboard sensed data and/or results may be transmitted wirelessly, such as to a remote server 74 or client computing device 73, e.g., a smart mobile phone 78 of the user, whereby the user may pull up and view the sensed and/or analyzed data from the wirelessly coupled sensing and/or monitoring watch-configured device 15 and/or to an associated mobile smart phone 78. In particular instances, the on-board computing system 45 may be in communication with a remote server system 74 through which the various analyses described herein may be performed. Likewise, the onboard computing system 45 may be in communication with a remote client computing device 73, such as a mobile computing device 78, for transmitting the read and/or analyzed data as well as the results of the analytics system, based on the readings attained by the biological sensor and/or monitor 15.

In particular instances, the device 90 can be configured as a watch and include a wristband peripheral 96 so as to be coupled the wrist of a user, as shown in FIG. 6B. In various instances, the wristband 90 may be an elastic or silicone band that stretches to allow for application to the wrist but then compresses so as to hold the sensor 15 behind the watch firmly in place, while worn. In such instances, the watch and sensor device combination may be waterproof so as to be worn for prolonged periods of time. In such instances, the band 90 or other attachment structure 12 may be configured to position the wearable electronic apparatus 15 on a body part of the user, or specifically, to position the sensor part 15 of the device in proximity with the skin and/or a blood vessel therein of the user.

For instance, in a specific embodiment, the sensing and/or monitoring device 15 may be configured as a watch 90, such as a smart watch, and in such instances, the band 96 can further include one or more connectors, such as for associating the smartwatch with the band 96 and/or the band with the wrist. In some implementations, the band can include a connection to receive a smartwatch, such as a pin connection. In various other instances, the attachment structure 12 for the watch may be a expandable and compressible sleeve, a watch-band, a headband, and the like. In other instances, the sensor device 15 may be configured as a necklace, a bracelet, an anklet, a ring, a pendent, or the like, where an adhesive may or may not be needed to form an attachment. In any of these instances, the sensing and/or monitoring device 15 may include an output device, such as a display, which may be in communication with at least one of the one or more onboard processing elements, for reflecting any of the readings, ratings, and/or outputs to the individual wearer. However, in certain embodiments, a display may not be included, such as where it is omitted to preserve battery life and/or duration during which the apparatus is applied to the body.

Accordingly, regardless of the form factor of the herein disclosed non-invasive, continuous biomolecule sensing and monitoring device 15, e.g., regardless of being in a patch-like 11 or watch-like 90 assembly 10, in one aspect, provided herein, is a method for monitoring and assessing an individual's biomolecule levels, such as blood glucose levels. For instance, in particular implementations, the method may include one or more steps of providing a wearable electronic sensing and/or monitoring device 15 as described herein, such as where the wearable electronic device 15 includes one or more sensing devices and/or sensor units 18, e.g., including a photoemitter and photosensor, at least one processor 45, and/or a wired or wireless communications module 44 for data transmission.

The method may include positioning the wearable electronics apparatus 10 on the skin 100 of an individual, such that the sensor unit 15 is in a position so as to direct generated energy into an area of the body, where the area is sensitive to biomolecule, e.g., glucose, within the tissues and fluids in the sensitive area, such as depicted in FIG. 5E, right hand side. Next, the method may include illuminating the skin 100 with energy from the photoemitter, and receiving an amount of energy back, e.g., at a photoreceiver, so as to take simultaneous measurements of one or more of heart rate, cardiac activity, and collecting reflected light from the photoemitter. Then, once the data, e.g., reflected energy data, is collected, the at least one processor can be employed to convert the heart rate, pulse-wave-velocity (PWV) measurements, and reflected and/or refracted light data, e.g., spectral analysis data, into a prediction about one or more characteristics about the biomolecule being observed. For instance, one or more estimates about the level, concentration, PWV effect, and/or effects of the biomolecule, e.g., glucose, on the body may be made.

Additionally, an output reflecting any of the readings, ratings, and/or characteristics may be displayed, e.g., through the output/display module, or may be transmitted to a suitably configured external display device of the individual. In some implementations, the taking of the simultaneous measurements step may be accomplished autonomously and/or automatically on a periodic basis, such as using a timer. In certain instances, the output of the data readings and analysis can be subject to a tagging and/or auto-tagging program where the apparatus 10, or associated analytics system 71, can determine the individual's behavior during an activity (such as eating, sleeping, working out, or during an episodic stress event) at a time point and attach an electronic/digital tag to that event. In some instances, the output of the data readings and further analysis can provide a health trajectory for the individual to predict a future state of health and/or what the effects of a remedial intervention will be.

Consequently, in view of the above, provided herein is a non-invasive, continuous biomolecule monitoring (NICBM) method for measuring one or more biomolecules, such as glucose, non-invasively through the skin via an optical sensor unit, such as by spectroscopy, such as visible, near-infrared, and infrared spectroscopy. These methods are non-invasive in that they do not use finger pricks or a chemical laden sensor unit that gets inserted within the skin. Rather, the sensor devices employed in the methods disclosed herein use electromagnetic radiation that is directed into the skin, and then measures transcutaneous light signals that are reflected back. From these detected light signals, a level, concentration, and/or change in an interstitial biomolecule, e.g., glucose, can be determined and/or predicted.

For instance, from the reflectance and/or refraction of visible and/or near-infrared (NIR) and/or infrared (IR) light directed into the skin, an estimated and/or predicted biomolecule, e.g., glucose, value can be detected and/or determined. For example, using one or more light generating arrays in the performance and/or determination of glucose is useful because it is non-invasive and, therefore, does not have a subcutaneous measuring component. Further, once one or more readings have been obtained, accurate estimated glucose values may be determined and calculated, e.g., based on electromagnetic radiation sensor signal inputs. As indicated above, such a determination may be performed by a pre-trained and/or locked Artificial intelligence module, such as employing a machine learning and/or inference engine. For example, in particular implementations, the machine learning component may be embodied within an artificial neuro-network (ANN), as described herein below.

Use of an AI mediated data structure, such as an ANN set forth herein, is useful for overcoming the aforementioned positioning problems. For example, another problem with typical amperometric sensor devices is that based on the internal positioning required of the sensor unit, its options for placement on the body is limited to larger body structures, such as the abdomen, buttock, or the like. However, this is a benefit of the sensing and monitoring devices presented herein, because based on the use of an illumination array and its non-invasive nature, the herein presented devices may be comfortably positioned on a number of different areas of the body, such as on the arm, leg, or the like. Hence, the present devices are flexible in terms of their placement on the body.

One problem, however, is caused by the movement of the sensing and monitoring device and/or apparatus, after a calibration process has been performed. This problem, however, can be overcome by the analytics system presented herein. For instance, the analytic system herein is adaptable so as to account for such problems by being adaptable to changes in positioning by being able to take into consideration of the different structures of the body when generating a topographical mapping of the tissues, internal structures, spaces, and fluids therein that make up the field of view of the sensor's illumination array when moved from one place to another on the body. Specifically, in various embodiments, to account for this difference in sensor application site, the sensor software, e.g., being run by the on- or offboard computing systems, is adaptable such that it can be trained in a manner that does not depend on body placement, but, nevertheless, can accommodate for it by the mapping process, which mapping is capable of accounting for various different changes in placement.

Hence, once placed and positioned on the body, the device in its placement may be calibrated, the calibration may be mapped and categorized as to body position, and once calibrated, the system should not need to be recalibrated again, unless the positioning or placement is changed, whereby a previous mapping can be used to identify the new positioning. Hence, such calibrations are useful because they allow the software and optical units to account for any variation from the new placement location to the other, such as by small movements and/or larger placements to a different part of the body. In particular embodiments, the calibration may include determining a correspondence of sensed values with determined blood glucose values, e.g., from a blood glucose monitor.

Further, because the analytics system does not need to include physical elements that need to be inserted within a tissue of the body for the purpose of determining characteristics and/or levels of biomolecules, the configuration of the internal electronics are also adaptable so as to make room for a larger battery, and because no analytes are involved that need to be changed, the present devices can be continuously used over prolonged periods of time, without the need for repeated calibration, such as up to 7 days, up to 21 days, up to one or more months. In this regard, the battery may be configured for being recharged, such as in a wireless (or wired) manner when the device is or is not being worn. In various embodiments, a non-rechargeable battery, such as a lithium manganese dioxide battery, may be used, which is not reusable or rechargeable. However, in certain embodiments, a non-rechargeable battery should not be used. Instead, a rechargeable lithium-ion battery may be included.

The biomolecule sensing and monitoring device 15 senses, collects, and tracks spectral reflectance and other data over a prolonged period of time. This data may then be preprocessed and be transmitted, e.g., wirelessly, to a remote computing system 70, such as a cloud-based server system, running or otherwise being associated with an Artificial Intelligence (AI) Module 72, such as instantiating a deep learning Artificial Neural Network (ANN) that has been trained to map the collected readings to a specific biomolecule, e.g., glucose, measurement. Particularly, in certain embodiments, the data collected, collated, and/or amalgamated through the device 15 can be subject to "machine learning" systems and methods to provide for predictive analysis for the individual, configured in a format so as to assist the individual in achieving personal health and wellness objectives, not necessarily alone, but in collaboration with their healthcare professionals, such as through the system application 80. In various embodiments, the data collected by the sensing and monitoring device can be employed by the analytics system to apply physical health and/or psychometric data analysis to assist the individual in achieving their personal health and wellness objectives.

Accordingly, in view of the above, as can be seen with respect to FIG. 7, a process for determining the presence, level, and/or concentration of one or more biomolecules, such as a metabolite, e.g., glucose, in the interstitial fluids or blood, such as using the non-invasive, continuous biomolecule sensing and/or monitoring device, disclosed herein above. Generally speaking, as set forth in FIG. 7, at step 110, the process may largely include collecting spectral and biometric data of the user, such as using the sensing and/or monitoring device set forth herein. The sensor device includes at least one energy emitter, e.g., a light emitting diode (LED), and at least one energy receiver, but may typically have 3, 4, 6, 10, or more, such as 20, 30, or even 50 or more electromagnetic radiation emitters, as well as having 1, 2, 3, 4, 6, 10, or more, such as 20, 30, or even 50 or more electromagnetic radiation receivers. In such instances, the various, e.g., 10 energy emitters, may direct light energy into the tissues of the body, whereby a portion of the emitted light impinging into the skin will be absorbed, e.g., at specific depths, and some will be reflected back so as to be collected by the various, e.g., 2, photodiodes.

Then at step 110*b*, the collected reflected spectral data may be pre-processed such as by at least being converted from raw analog data into digital read data via an analog to digital converter, ADC. Specifically, the ADC processes the LED spectral data, current data, and photodiode intensity data, which, once pre-processed, the data may be stored in an onboard memory, such as a flash memory. The pre-processed data can then be transferred to an on- or off-board computing system whereby the data may be evaluated and/or be subjected to a reinforced, DVRL, protocol, and be subjected to neural network filtering. Then at step 110*c* the data, e.g., filtered data, can then be integrated within a data structure and be processed, such as by an artificial neural network, whereby the individual's biomolecule values, e.g., glucose levels, may be calculated.

The collected data, therefore, may include a measurement of a level of a biomolecule, which may be indicative of a health condition, such as for determining a glucose value. Then at step 110*d*, the results of the analysis, such as including glucose concentration levels, as well as a prediction about the health of the individual may be output, such as to a mobile computing device, e.g., a smart phone, of the individual, for display thereby, such as where the smart phone is running a client application of the system. The outputted day may further include various trend and/or pattern data determined by the system over several hours, e.g., 1, 3, 6, 12, 24 hours, over days, e.g., 2, 3, 4, or weeks, or even months. All of this data may also be uploaded into the cloud, e.g., for storage and or further processing, and/or may be transmitted via the client application to a computing system of a healthcare professional so that the individual may receive help and guidance in meeting their health goals and wellness objectives.

More particularly, as can be seen with respect to FIG. 8, in various embodiments, the NICBMS may include a mobile device, such as communicationally coupled with the sensing and monitoring device, such as where the mobile device is capable of running a downloadable application of the disclosure. For instance, a downloadable mobile application may be included whereby the application is configured for working with one or more processors of the mobile device so as to generate a graphical user interface, which user interface may display an interactive dashboard display screen. In various embodiments, the mobile application may be configured as a Software as a System application whereby a system user may view biomolecule, e.g., glucose, and/or other health data, can see values over time, can view graphs and trends, and through which they may receive health recommendations.

Besides showing the biomolecule and/or health data, as well as analytic results relevant there to, the software application may also be used to set up and/or remotely configure the sensing and monitoring device, e.g., for first-time users, and to calibrate the sensor, e.g., for every application and reapplication, such as to start/stop the automatic measurements, and/or shut off the sensor, as need may be. For instance, when a user first receives the sensing and monitoring device, they will set up a user account, input their personal physiological information, and register their sensor. In particular embodiments, the registration date for the sensor may be important because at 1-year post-registration, the onboard software may automatically shut off the sensor to ensure the device is only used for a designated sensor life.

Specifically, once downloaded, the mobile application may be used to not only set up and configure the sensing device, it may also be used to calibrate the system to each specific user. For example, once the sensing device is fully be charged, and the application downloaded to the user's smart phone or watch, the sensor device may be coupled, e.g., via BLE, RFID, etc., to an associated mobile computing device of the user, and the mobile application for running the software of the system may run the user through a set up and calibration protocol. First, a user account with a user profile can be set up and registered, individual characteristics about the user, their background their family background, health and psychological history can all be entered into the system, such as in response to a system generated interview. This is important for determining characteristics about the user so as to generate a user profile.

Once the account has been set up and a specific sensing device to be used has been coupled to the mobile application, then the device may be applied to the body. First, the user will position the sensor unit for insertion into the attachment structure or dome to form the apparatus. Then, any backing material may be removed from a skin-interfacing surface of the attachment apparatus and/or dome. The apparatus with the protective glass of the sensor facing outward, e.g., downward, may then be positioned on to the skin so that sensor units of the device will be in contact with skin once applied. The user can then press firmly against the attachment structure to ensure the adhesive is securely placed. After the sensor and apparatus are placed on the body, e.g., the back of the arm, the user can then use the mobile application to communicate with the device, and vice-versa, so as to initiate and run a calibration protocol, which may include taking, or otherwise entering, a blood glucose measurement, such as with another pin-prick style device. Upon calibration, the user may select to start measurements and the sensor will autonomously transmit data from the sensor to the software platform. The user can view their estimated glucose value, 1-, 3-, 6-, 12- and 24-hour daily glucose trend graphs, time-in range (TIR), and glucose trends over the last 7 and 30 days in the software platform. After the life cycle of the device, e.g., one, two, three, five years of use, the sensor may automatically shut off, and the user may then apply a new sensor device to the body and recycle the old device.

Following device setup, the user may follow the application's calibration instructions to input their blood glucose values, such as may be measured by the system themselves, or with an auxiliary blood glucose monitoring device, so as to set a baseline reading prior to starting the sensor readings. Further, during the sensor's life cycle, the mobile software application may also notify the user with alerts and alarms if and when the device needs to be recharged and reapplied with a new adhesive bandage, e.g., at the end of a 14, or 21, or 28-day wear period during an application cycle. Alerts and alarms may also be used if the software application detects signal loss, e.g., photodiode signal loss, BLE communication loss, sensor failure, transmitter failure, and/or if excessive temperature is detected by the sensor. When these alerts and alarms are triggered, the software may guide the user to resolve/troubleshoot the issue with prompts.

Hence, once such biometric and spectral data has been collected by the sensing and/or monitoring device, the collected data may be transmitted to an associated computing system, whereby a biomolecule, e.g., a glucose, level, and its effects on the body of the user may be calculated. In various embodiments, the calculations may be performed using one or more of on an on-board or offboard computing system, such as implementing, or otherwise being associated with, a machine learning and/or inference engine, e.g., based on the collected data. And, finally, the process may include outputting at least one of the calculated results, such as by transmitting the results to one or more server systems and mobile computing device running a biomolecule sensing and/or monitoring application configured for displaying such results. All of these steps may be performed non-invasively in a manner that does not physically harm the individual.

In view of the above, a key component of the device is what it does not contain, and that is the device may be configured for using spectroscopy, such as light or radio frequency spectroscopy, to measure biomolecule levels without any portion of the device, or an associated apparatus, penetrating and/or otherwise impinging into the skin. Specifically, the device may be needle-free in that it employs spectroscopic light and/or radio-frequency (RF) and/or microwave techniques to detect the presence of biomolecules, e.g., glucose, in dermal tissue layers, such as where the biomolecule is a photo active, e.g., infrared active, and/or radio-active component. In this regard, at Step I, the device may be placed on a surface of the skin and is configured for directing visible, near infrared (NIR), infrared light, RF, and/or microwave emissions into the skin, and further is configured for receiving and detecting the light, RF, and/or microwave signals reflected back.

Particularly, in various embodiments, the transcutaneous sensor and monitor may include a number, such as up to 10 or more photo-emitters, e.g., Light Emitting Diodes, that direct visible, NIR, and/or infrared light at the skin in a pattern of different light frequencies, intensities, and durations employing the LED array. In various instances, the referenced emitters may be one or more radio frequency or microwave emitters, and the receiver may, therefore, be an RF or microwave receiver. So being, in such an instance, the emitter and/or receiver may be configured as an antenna array. Accordingly, the device may include a number, such as one or two or more, light receivers, such as photodiodes, which are configured for receiving the light reflected back from the skin, and as indicated, in various embodiments, the receiver may be an antenna array, such as functioning as an RF or microwave receiver. More particularly, the spectral signal detected by the sensor's photodiodes or RF/Microwave receivers is affected by the complex relationship of biomolecules, e.g., glucose, with light and/or RF/Microwave frequency, intensity, and exposure time, which may represent a "biomolecule mediated skin response," such as a glucose-mediated skin response.

For instance, the referenced spectral analysis may be performed in accordance with a number of different principles. First, in one iteration, it has been determined herein that the presence of glucose, and other biomolecules, such as metabolites, within the skin and/or interstitial fluid, changes its reaction to electromagnetic radiation, such as light and/or radio and/or micro-waves, such as by changing color, thereby evidencing a spectral shift, e.g., on the near-infrared spectrum. In various instances, a corresponding interaction can be determined using a RF and/or microwave transmission. In either instance, light and/or sound and/or microwaves may be absorbed and/or reflected differently in the skin and surrounding fluids based on the biomolecules present therein. Consequently, when energy is transmitted into the skin the skin may react in certain characteristic ways to that energy, such as in an observable manner.

Hence, the devices, systems, and their methods of use disclosed herein may be configured for detecting and quantifying such characteristic changes. Further, in various embodiments, detection of biomolecules within the skin and spaces therebetween may be guided in part by Beer-Lambert's law, which is based on light absorption being directly proportional to the concentration of light absorbing elements being present within the skin, their concentration, and the optical path length traversed by the light signal. Consequently, Beer-Lambert's law may roughly be attempted to be mechanized so as to account for the presence and/or differences in levels of biomolecules in the skin based on light wave absorption, reflectance, and the time from emittance to reception, while accounting for changes in the optical path, such as by using one or more of light and/or laser-based spectroscopy. However, the mechanization of Beer-Lambert's law is not a straight forward process, as the law in and of itself is unable to fully capture the nuances of photo-based biomolecule, e.g., glucose, detection without the devices, mechanics, and calculations performed by the methods disclosed herein.

More specifically, in order to account for a number of different skin types, pigmentation, absorption characteristics, biomolecule features, light wave affectations, and other such variables, use of an artificial intelligence has been developed to account for the variance in such changing conditions. In particular embodiments, these methods are useful for determining a level of glucose, such as in the interstitial space, which in turn is useful for monitoring and/or modulating hyper glycemia, diabetes, and other health conditions. Such measurements and determinations have been attempted, but have heretofore been unsuccessful because, as discussed above, it is difficult to maintain a consistent topology of the dermal layers within which the measurements are taken. The present technology over comes such difficulties by using an array of photo-emitters, stably locking the sensing device immovably in a singular position on the body, e.g., preventing lateral and rotational movement, and/or correcting for variable inconstancy, such as minimal movement, via a suitably configured Artificial Neural Network, as herein described.

Specifically, in various embodiments, an AI module employing machine learning and inference generation may be used so as to develop one or more models to take the various different datapoints, variables, and changes thereto into account by building a data structure, such as an artificial neural network, by which to make a determination of a biomolecule level within the skin, vessels, and interstitial spaces, in a manner that one or more unhealthy, e.g., disease, conditions can be sensed, monitored, and/or tracked over time. Data to be entered into such data structures may be collected by using a variety of different energy emitters and receivers so as to produce a spectral array, along with other biological data, that can be analyzed in accordance with a number of different principles. With this in mind, the present sensing and monitoring devices has been developed to work in conjunction with a suitably configured analytics platform so as both sense and determine a biomolecule, e.g., glucose, mediated skin response, as well as to analyze the same, such as by using a deep learning-trained, locked data structure, such as implemented as an ANN.

For example, in performing these procedures, at Step 1 at 110*a*, energy, such as light and/or radio or micro-waves, may be emitted into the skin, the biomolecules present therein and around then react to that energy, whereby, some of the light or radio and/or micro-waves are absorbed, some of the energy may be refracted, and some of the energy is reflected back, such as to the appropriately configured receiver, e.g., photodiodes or RF or micro-wave receivers. Consequently, at Step 2 at 110*b*, the reflected energy, e.g., light or RF, signals are collected and preprocessed, and then transmitted, e.g., wirelessly, to one or more of remote computing systems and/or associated client computing devices, such as a mobile computing device, e.g., for display thereby. Specifically, in various embodiments, the sensing and/or monitoring device may be configured to automatically emit and capture reflected energy signals every 1, 2, 3, 4, or 5 or more minutes.

Specifically, at Step 2, from the detected spectral signal, the analog-to-digital converter (ADC) coupled to the PCBA may then preprocesses the spectral data. For example, in an exemplary embodiment, the emitter may be a photo-emitter, such as an LED, and the receiver may be a photodiode. In such an instance, the data collected by the photodiode may include one or more of the LED capacitance, the current, voltage, amplitude, and/or the photodiode intensity, which may be saved to a local, or remote data storage 76, such as in a first-in-first-out (FIFO) flash memory. In certain instances, the same may be similarly true for detecting RF or microwave frequencies and wavelengths.

In any of these instances, the onboard memory may be configured to store such data for a prolonged period of time, such as at least 7, 14, 21, 28 or more days, including 1 or 2 or even 3 or more months, such as encapsulating multiple, 1, 2, 3, 4, or more wear periods, all of which can be stored on the local flash memory. Also, during this preprocessing step, readings with poor quality, including readings derived from bad transmission, incomplete signal, electrical interference, excessive pressure on the sensor, an obscuring substance on the skin, or other factors, may be filtered, such as using an onboard AI, system, such as filtering sub-system, such as a data valuation with reinforcement learning (DVRL) neural net. For example, in certain instances, this preprocessing DVRL neural net filtering may be trained.

Following signal preprocessing, at Step 4 at 110*d*, the PCBA's communications module, e.g., miniature radio transceiver, communicates this information, e.g., via BLUETOOTH, BLE, WIFI, or other communications protocol, to an associated computing device, such as to a software platform downloaded to and being run on a smart device. In such instances, as can be seen with respect to FIG. 8, the mobile application software platform can convert the reflected energy's spectral signal using the AI module, e.g., ANN algorithm, to derive an estimated biomolecule value, such as glucose values.

More particularly, in specific instances, such as where the biomolecule of interest is glucose, the sensing and monitoring device may be specifically attuned to estimate glucose values such as ranging between 40-400 mg/dL, e.g., based on the glucose-mediated skin response to the directed visible and NIR light. As indicated above, the PCBA sensor and/or monitor may have any reasonable number of energy emitters, such as 4, 6, 8, 10, or more, so as to direct energy, such as visible, NIR, and/or IR light or RF energy into the skin. In certain embodiments, each emitter may transmit energy of different wavelengths, such as where the energy wavelength is of a length and frequency to produce a reaction in the biomolecule, and/or surrounding tissues, that may change based on the received energy characteristics, e.g., wavelengths and frequencies, being directed into the skin, which changes can be used to determine biomolecule value, such as where the spectral shift and/or intensity is determinable based on concentration. Hence, the number of emitters, e.g., LEDs, and the wavelengths they emit, may vary dependent on the molecule being observed, and the energy required to produce the observable spectral shift.

In such embodiments, the analytics system may be configured to observe wavelength emittance, duration, and intensity, as well as the affects thereof on the body, and can then weight the wavelength, duration, intensity, etc. based on the observable effect, and/or can change the intensity, duration, and/or the wavelength itself, such as to provoke the desired spectral shifts so as to better make and evaluate the concentrations of the biomolecule and its effect on the body tissues. From this data, and in accordance with the procedures disclosed herein, the most effective spectral array of emitters for producing the desired response for taking measurements may be determined, the effective emitters can be selected, and their emission and wave characteristics can be set so as to make the requisite measurements, such as to generate a spectral array from which an accurate glucose value may be determined. For instance, where glucose is the biomolecule of interest, at Step 1, when the sensor performs a measurement of a subject's glucose level, the LEDs are activated in sequence, e.g., from lowest to highest wavelength, or vice versa, or may be activated in a non-sequential manner, e.g., randomly, in a pattern of varying LED intensity and LED activation times.

For example, in implementing this step for detecting and monitoring a user's biomolecule, e.g., glucose, levels, at 110*a*, the method may include one or more of the following steps. First, an emitter, e.g., a photo-emitter, may be energized, such as by supplying power to an associated capacitor, and a first light of at a first wavelength may be emitted and directed into the skin of the user. Additionally, the same process can be repeated so that a second emitter is charged so as to emit a second light at a second wavelength, a third emitter may emit a light at a third wavelength, and the same for the emittance of a fourth light at a fourth wavelength, the emittance of a fifth light at a fifth wavelength, likewise a sixth light at a sixth wavelength, and the same for as many emitters are selected for emitting wavelengths, such as seventh, eighth, nineth, tenth, or more.

Particularly, in particular embodiments, the photo, e.g., light, emitters may be configured for emitting, and the photo receivers, e.g., photodiodes, may be configured for receiving light from a broad-spectrum, such as in the range from about 500 nm to about 1000 nm, and/or from 1000 nm to 1700 nm or more. For instance, in various embodiments, two arrays of photoemitters may be employed, such as where the first array is configured as a broad-spectrum array that includes a number of photoemitters that are adapted for emitting light in the range from about 500 nm to about 1000, and further the second array may be adapted as a broad-spectrum array that includes a number of photoemitters that are configured for emitting light in the range from about 1000 nm to about 1700 nm.

More particularly, in some embodiments, the first array may include four emitters, surrounding one or more receivers, where each emitter emits light of a different wavelength, but collectively the array emits light of a first wavelength, which may be about 550-60 to about 640 nm, light of a second wavelength, which may be about 650 nm to about 840 nm, light of an third wavelength, which may be about 850 nm to about 930 nm, and light of a fourth wavelength, which may be about 940-50 nm to about 1040 nm. Likewise, the second array may include six emitters, surrounding one or more receivers, where each emitter emits light of a different wavelength, but collectively the array emits light of a first wavelength, which may be from about 1200 nm to about 1290 nm, light of a second wavelength, which may be from about 1300 nm to about 1390 nm, light of a third wavelength, which may be from about 1400 nm to about 1490 nm, including about 1450 nm, light of a fourth wavelength, which may be from about 1500 nm to about 1540 nm, light of a fifth wavelength, which may be about 1550 nm to about 1640 nm, and light of a sixth wavelength, which may be from about 1650 nm to about 1750 nm. In some embodiments, any one of the light sources may be an LED, and/or the wavelength of the emitted light may vary by +/−about 10-25 nm, about +/−50 nm, about +/−100 nm, and the like. In certain embodiments, a filter may be placed over one or more photoemitter and/or over photo-receiver, e.g., photodiode, such that each photoemitter and/or each photodiode can emit and/or receive and detect a very narrow range of wavelengths. In some implementations, each filter may be a physical device consisting of a small piece of plastic, glass, or other semi-transparent material that has band gap filtering properties. The band gap filtering properties can be from the filter material itself, or from additional materials added to a base material. The filter material may include an anti-reflective coating, and may be engineered to only allow passage of light within a narrow bandwidth.

Accordingly, in view of the above, after emission, the process may further include receiving at a first or second or third, or more energy, e.g., photo, receiver at least a portion of the first light reflected from the skin of the user, and at least a portion of the second light reflected from a skin of the user, and at least a portion of the third light reflected from a skin of the user, and at least a portion of the fourth light reflected from a skin of the user, and at least a portion of the fifth light reflected from a skin of the user, and at least a portion of the sixth, seventh, eighth, nineth, tenth, and so on, light reflected from the skin of the user. For example, once the light has entered the skin, a portion of the light will be absorbed, some will be refracted, and some of the light will be reflected back and thereby received by 1, 2, or more photodiode sensors on the PCBA, which photoreceptors should be attuned to cover the range of potential LED wavelengths, and the reflected light may be measured after each LED activation.

Upon receipt, at Step 2 at 110*b*, the received sensed data will be preprocessed, such as by an on-board analytics module. Specifically, once the reflectance has been emitted and received by the device, the next step in the process may include determining a first reading corresponding to the amount of the first light being absorbed and/or reflected by the tissues and interstitial fluids, blood, and/or biomolecules therein within the skin layers of the active site under observation. Likewise, a second reading corresponding to the amount of the second light being absorbed and/or reflected by the skin and its components, and a third reading corresponding to the amount of the third light being absorbed and/or reflected back, and the same for a fourth, fifth, sixth, etc. readings being made corresponding to the amount of the respective light being absorbed and/or reflected back by the skin and its components.

Finally, once the data has been collected, one or more characteristics of one or more molecules within the skin of the active area may be calculated. For example, in one embodiment, the system may be configured for employing these methods such as for calculating a wearer's glucose levels. In various embodiments, such calculations may be performed by an associated AI module of the system, such as implementing an artificial neural net. Then, after the sensed data is preprocessed by the sensor, at Step 3, at 110*c*, the preprocessed data may be transmitted and be received by a remote server system, such as where the pre-processed signal inputs may be run through the analytics system, such as an ANN, whereby the estimated glucose values may be calculated.

Further, in various embodiments, a number of other different characteristics may also be measured, and accounted for in the calculations, such as the skin temperature, e.g., at the surface of the sensor, pulse rate, e.g., derived from photodiode signals, and patient physiological information (e.g., age, gender, sex) may also be incorporated as inputs into the glucose conversion process as the processing and consideration of such additional factors may impact the glucose spectral signal. Furthermore, in a further Step 4 at 110*d*, an output of the analysis may be a glucose measurement, which may be displayed to the wearer of the device, which may include the temperature and pulse rate signal data collected. In such instances, the user can view the current estimated glucose value, the glucose rate of change, daily and historical glucose trend graphs, and time within the range, such as within the mobile application.

Accordingly, in one aspect, as set forth at 110*c*, provided herein is an analytics module, which may include, or otherwise be associated with, an Artificial Intelligence (AI) module, which AI module may instantiate a data structure such as for implementing an Artificial Neural Network (ANN), or other data structure. For instance, herein presented is an AI module that may include one or more machine learning engines as well as one or more inferences engines, such as for accurately determining biomolecule values, levels, concentrations, as well as the health conditions associated with the same. Particularly, as described here in detail below, a machine learning sub-module may be provided, such as to build a data structure, e.g., ANN, from which one or more inference sub-modules may further be provided so as to employ the data structure to generate one or more inferences and/or predictions may be made, such as to the presence, value, e.g., concentration, and/or effects of a biomolecule on the body tissues, as well as with regards to any associated health conditions that may result with respect thereto.

For instance, in a particular implementation, the machine learning and/or inference generating sub-modules may implement or otherwise instantiate one or more of a polynomial regression analysis, a neural network, a Bayesian network, a decision tree, an adaptive logic network, an artificial neural network, a support vector machine, and the like, such as for determining and analyzing trends, e.g., with respect to one or more characteristics of a biomolecule and its effects on the body, and providing intelligent insights with respect thereto. In particular implementations, the AI technology disclosed herein may be configured for determining the characteristics of glucose molecules and their effects on the body over time, e.g., glucose Levels. In such an instance, in determining a biomolecule level, a data structure, such as an artificial neural network (ANN), may be generated and/or trained, such as in a manner that the data used to build and train the neural net on the specific biomolecule of interest, and as such, a number of different neuro-nets may be produced, each structured and/or focused on a specific biomolecule(s), such as glucose, and/or with regard to one or more specific individuals. As such, the training and/or analysis may be performed on continuous, real-time, data collection and analysis, such as for one or a number of readings for one or a number of subjects over a prolonged period of time.

Accordingly, in one aspect, provided herein is an analytics system 71, which may include an AI module 72, wherein the analytics system may be configured so as to implement one or more algorithms for receiving sensed data, and using that data to make one or more measurements from which a determination of a biomolecule or of a biological condition may be made. In using the device, the AI, e.g., a machine learning sub-module, may first be trained, and once training is complete, an inference engine may be employed so as to make one or more determinations of one or more characteristics of a biomolecule of interest being present within the body tissues, as well as to one or more conditions that may be experienced because of the presence of the detected biomolecule.

With respect to the artificial intelligence module, in one aspect, one or more local and/or cloud accessible artificial intelligence modules are provided, and are configured for being communicably and operably coupled to one or more of the other sub-systems of the biomolecule detecting, sensing, and/or processing pipeline disclosed herein. For instance, the one or more AI modules disclosed herein may work closely with a suitably configured analytics management system so as to efficiently direct and/or control the various methods and processes of the analytics system disclosed herein. Accordingly, provided herein, is an analytics system that may include one or more, e.g., a plurality, of AI modules, which are configured for acting as an interface between one or more observable characteristics of an individual, one or more artifacts within their tissues, interstitial fluid, and/or blood, and one or more measurements being performed so as to determine the presence and/or effects of those artifacts on the body.

The analyses to be performed by the AI modules of the system may be directed to detecting the presence and/or characteristics of one or more biomolecules within the body, the effects their presence has on the body, and further, for determining one or more remedial actions that can be taken in light of the presence of the biomolecule and its effects. For instance, in various instances, the system may be configured for performing a number of measurements, e.g., within the tissues of an individual, as disclosed herein, so as to derive spectral data therefrom, along with other biological condition data, from which data, the analytics system can use the raw and/or pre-processed spectral data to determine the presence of a biomolecule within the tissues of the individual as well as a condition of that individual due to the degree of presence or absence of that biomolecule, e.g., with respect to its amount and/or concentration. For performing this analysis, a data structure may be generated and populated with biomolecule data, user condition data, and/or characteristic data, as well as, with spectral data from the individual, all of which may form nodes in a graph or neural network structure.

With respect to the spectral data, as explained herein below, the spectral data may be of two kinds: spectral data that has been correlated with known levels of a biomolecule, e.g., known spectral data, and spectral data that has not been so characterized, and thus, is unknown. In this regard, where glucose is the biomolecule of interest, a blood glucose meter/analyte sensor that is known to give accurate results, e.g., blood glucose measurements, e.g., invasively, can be used to generate a known presence and concentration of glucose value. This known glucose value data may then be correlated with the condition and spectral read data so as to produce the known spectral read data, such as where it is known, regardless of the read data measurements, whether glucose is present and at what concentration, because that value has been determined by use of the invasive glucose monitoring system. Consequently, this data may then be used to populate a data structure, whereby the unknown spectral data may be tested and/or determined.

In a first step, all of the known data may be populated as nodes within the data structure, such as a table, a tree, a graph, a neural net, e.g., an ANN, and the like. This known data, including the spectral data and known glucose measurement data may then be mined to determine correspondences between the nodes. The correspondences may be weighted, and one or more models may be generated by which the correspondences may be determined and tested. In a second step, a series of known first measurements may be taken where the presence of the biomolecule of interest is tested for both by using the spectral array system of the disclosure, as well as using a blood glucose meter that tests the blood directly, each tests producing results that can then be evaluated and correlated, so as to produce further known data. These results can then be entered into the data structure, pre-existing correlations therebetween can be strengthened, e.g., increased in weight, new non-correlations can be decreased in weight, and any new correlations can be defined and be initially weighted.

Consequently, in this manner, a first correspondence between the presence and concentration of the biomolecule, the condition being experienced, and the measured spectral read data can be determined. As explained herein below, these correlations in the known dataset may be used to evaluate the spectral data and determine the presence and/or the effects of the biomolecule of interest, in circumstances where the presence and concentration of the biomolecule is known, and this data may be used to generate a model. The model may then be used to evaluate spectral data such as where it is not pre-known if glucose is present and at what concentration, e.g., where an actual blood glucose measurement has not been taken, and a determination of the value of the glucose is being made simply on comparing actual measured spectral data, as obtained from the devices herein described, to the model.

For the generation of the data structure, development of the model, and for the performance of known and/or unknown evaluations, a workflow manager system (WMS) may be instantiated and implemented. The workflow manager may function to receive and analyze the individual characteristic data, known biomolecule data, the spectral data, as well as the known measurement data that sets forth the presence and concentration of the biomolecule, other such biological and/or biomolecules data can also be retrieved. The WMS may then enter this data into the data structure from which a correlation between the observed spectral data and known biomolecule measurement data may be determined so as to produce the known read data.

The system may then perform one or more analyses on the associated known read data so to determine any and all correlations between the spectral array, known measurements, and any and all biological condition data collected. This process may be performed so as to train the model. Such correlations can be demarcated as a relationship between two nodes in the data structure, which in some instances would otherwise not be expected to be related. For example, in various embodiments, the methods and/or systems herein disclosed may be adapted for correlating an individual's personal characteristic data to one or more conditions the individual may be experiencing. This data may then be correlated to spectral measurements taken in the individual for a presence of a biomolecule, as well as to the known measurement data characterizing that biomolecule, such as with regard to its presence and concentration.

This known data can then be used to determine a relationship between the presence and concentration of the biomolecule with a known condition of the individual, such that it may be inferred that the biomolecule is known to be present at a problematic concentration, and thus, may be related to the onset and/or progression of the condition. This data may then be correlated with the spectral analysis data obtained from the sensor measurements being performed herein. A prediction of one or more relationships between the spectral data and the concentration of the biomolecule can then be made, and a further prediction about the spectral data and the condition can also be performed. These predictions may then be tested.

Accordingly, presented herein is a system for searching a database, such as a structured database, identifying one or more results fitting a search criterion, building a data structure with the obtained results of the search, and then using the data structure to determine one or more correlations. Once the data structure is built, it may then be used to generate a model, form which model unknown results may be compared to known results, and based on the comparison, a prediction about the presence and concentration of a biomolecule within the tissues of an individual, and/or its correlation to an unhealthy condition can be made, such as based on an analysis of the spectral array data obtained in accordance with the methods described herein.

A unique feature regarding the continuous biomolecule sensing and measuring systems disclosed herein is that they are configured for obtaining data continuously for a prolonged period of time. In this regard, therefore, the WMS and the data structure it produces is capable of obtaining data over a prolonged period of time, and thus, is configured for correlating data, such as characteristic data, spectral data, condition data, and/or known measurement data, over days, weeks, months and years. Such data may be correlated with respect to past, historical information, with regard to a single biomolecule, multiple biomolecules, one or more spectral patterns, and/or one or more conditions of the individual, such as may be resulting from the presence and/or concentration of the observed biomolecule within the tissue, in the present or with respect to past performances.

In various embodiments, components of the system may include one or more of a non-invasive, continuous, biomolecule sensing device of the disclosure, a server, including a processor, a database, such as a structured database, one or more sources for biomolecule and/or condition related data, a search browser, and the like. In particular embodiments, the system may be configured to encrypt data files as that data is uploaded, or otherwise entered into the system, so as to ensure the maintenance of privacy. This is important for adherence to HIPPA compliance. The files, e.g., records and/or index files regarding past spectral scans and related biological data and conditions, may be transmitted from each source of generation or storage to a repository 76 using any suitable transference protocol, and may be searchable, such as via a browser. The browser may be configured for searching the plurality of files, such as via use of the one or more index files. All of this data may be collected by the system and used to generate the data structures and models herein disclosed.

In various instances, the WMS may be configured for running a plurality of workflows related to a plurality of detection measurements having previously been, or currently being, performed with regard to the same or other individuals, and may, therefore, may implement one or more of the analyses described herein, which in some instances, can be implemented in a processing pipelined configuration. Accordingly, as disclosed herein, the system may be configured for receiving user characteristic data, condition data, raw-spectral and/or digital read data, as well as known biomolecule measurement data, but in various instances, the system may further be configured for correlating the received data with a database of stored known read data, known measurement data, and/or models previously generated with respect thereto.

For instance, the AI module may be configured for analyzing spectral data for a single person or multiple people, related to a single biomolecule or a plurality of biomolecules, and with respect to a single condition or a multiplicity of conditions. This data may be in relation to a single measurement or a plurality of measurements being performed over a prolong period of time for the one or more individuals. Further, all of these data can be collected under conditions where the biomolecule of interest is known to be present and its concentration and other values are also known, such as by being collected or otherwise generated at the time the spectral read measurements are being performed. These various data can be compared one with another and the percentage similarity, e.g., correspondence, between the two or more can be determined, collectively, and with respect to each individual factor. This data, therefore, can be termed "known data," with respect to its use herein.

For example, in certain embodiments, the system may include a variety of different databases, which various databases of the system may be configured so as to have a relational architecture, which may further be adapted to include one or more constructions, such as forming a data structure. For instance, in one implementation, these constructions may be represented by one or more table structures. In a particular iteration, a series of tables, for instance, may be employed by which correlations may be made by the WMS in an iterative fashion.

Particularly, in various use models, a first table may be generated and populated with respect to an individual's observed spectral data, e.g., read data, the system's evaluations of that read data over time, and with respect to one or more biomolecules, which all may be included in the first table. Another table may then be populated with respect to the individual's known measured biomolecule levels that were collected or otherwise determined at the same time as the read data was collected, such as with a separate blood glucose or glucose analyte monitor, as referenced above. A further table may then be generated and populated with any and all know biological characteristic data that was collected at the same time as the read and measurement data. In various instances, other tables may be generated with respect to the read data, measurement data, and condition data of one or more other individuals, with the same or similar conditions in response to the presence of the same or similar biomolecule with the same or similar values.

These three (or more) tables may then be compared with one another so as to derive one or more relevant correlations there between such as with regard to one or more of the read, measurement, and condition data, e.g., from one or more individuals of interest. Hence, the correlations set forth herein may be performed for the same or various different individuals, at a variety of different times and/or dates, such as in determining the level of correspondence between them. A key may be used to correlate the tables, which key may be accessed in response to a question prompt or command.

The key may be any common identifier, such as a name, a number, a nickname, a handle, a phone number, and the like, by which one or more of the tables may be accessed, correlated, and/or a calculation performed by use thereof. Without the key, it becomes challenging to build correlations between the information in one table with that of another. Hence, use of tables may be challenging, which may be made even more so by the time it takes for the system to search for, pull up the tables, retrieve the key, and search the tables so as to look up the answers.

Accordingly, a useful aspect of the present technology is a data structure for answering a query, wherein the data architecture may be structured and searched in response to a query in a more holistic manner. In particular instances, the query may be directed to determining a relationship between a present spectral array instance, and a number of past spectral array instances as compared to known measurements. In a typical architecture the database may be a relational database, such as a Structured Query Language (SQL) database, which may be implemented via a relational workflow and/or database management system (WMS). For example, as indicated above, in one implementation, the SQL database may be a table-based database, such as where one or more tables, e.g., look up tables (LUT), form a structure wherein data may be stored, searched, relations determined, and queries answered. Particularly, in various embodiments, a table-based database may be generated, searched, and used to determine relationships from which answers to one or more queries may be determined.

For instance, typically, SQL databases have a relational architecture. These constructions may be represented by a table structure. For instance, series of tables may be employed by which correlations may be made in an iterative fashion, as set forth above. For example, with respect to the correspondence analyses discussed herein, a correlation may be made with respect to an individual's spectral read data, such as with respect to one or more biomolecules suspected of being present within the tissues, one or more conditions suspected of being related to the presence of the biomolecule, and/or with respect to one or more measurements having been performed by a device that gives a known value for the biomolecule of interest. In various instances, the correlation may entail making a prediction about the presence of the biomolecule of interest being present at a given concentration based on the read data, and comparing the results of that prediction to the known measurements obtained, such as from precious analyzed read data. Likewise, a further table may be used to correlate the progress of the individual, across time, towards improvement of one or more of their biomolecule values and/or conditions related thereto, e.g., across a single or multiple events.

However, because of the time consumption required to implement a table-based data structure, a further data architecture may be used to structure a database of the system, such as a data tree structure, where various data elements may be stored in a compressed, but correlated fashion, and/or in a hash table. In certain instances, a root-tree-branch database may be deployed by the system, which data structure may be structured and used to determine the results for one or more of the queries set forth herein. Alternatively, a knowledge graph or neural network based, e.g., artificial neural network based, architecture may also be employed to structure the database, so as to enhance the performance of computational analyses executed using that database. In certain instances, the sophisticated algorithms disclosed herein, are adapted for structuring the infrastructure of a relational database so as to enable more efficient and accurate searching, such as by performing graph-based or neural network analyses, as well as for performing table or tree-based analyses.

Consequently, in one aspect, a device, system, and methods of using the same to build a searchable, relational data structure, such as described herein, are provided. Accordingly, in one instance, the machines and methods disclosed herein may be employed so as to generate and/or otherwise collect data, which data can be classified and categorized, and then be employed, such as by a WMS of the system, to populate a data structure of the disclosure. Specifically, the processing machines and their methods disclosed herein may be used to generate a searchable data structure for storing the collected and/or analyzed data in a relational architecture. In various instances, additional data may be generated or otherwise be transmitted into the system, such as via a suitably configured API, which data may also be configured for being stored in the relational data structure, such as other characteristic data of an individual and/or their conditions, or in relation to a biomolecule of interest.

In another aspect of the disclosure, the system may include an artificial intelligence (AI) module that may be configured to utilize the data structures provided herein so as to run a query thereon and return a result thereby. Implementing AI in this manner, and in this context, is useful because it may provide a more comprehensive analysis on generated and/or collected data, as especially compared to the time it takes and difficult inherent in using Lookup Tables, as described herein. For example, the AI module may be configured so as to implement one or more machine learning protocols on the data attained, e.g., known-measured and/or unknown-collected, by the system that are devised to teach the AI module to perform one or more correlations, such as between various spectral read data and known measurement data, generated or otherwise collected by the system, in comparison to read data of the same or another individual at the same different times, such as with regard to the same or different biomolecules.

Specifically, the AI module may be configured for receiving a plurality of inputs such as of captured spectral read data, and known measurement data collected at the same time the reads have been performed, such as from a blood glucose monitor or analyte sensor discussed herein. In such an instance, the AI module may be adapted for building and structuring a database for an individual in relation to the generated spectral data in further relationship to the collected known measurement data. In various embodiments, individual health and/or characteristic data may also be collected and input into the data structure.

Accordingly, in a first step, a first set of data may be collected and entered into a data structure of the system. For instance, this data my include spectral measurement data collected by a measurement device of the system, such as with respect to identifying the presence and/or concentration of a biomolecule of interest. In a second step, a second set of data pertaining to a known measurement of the value and concentration of the biomolecule of interest may be collected or otherwise entered into the system, such as via test device known to detect the actual presence and return the actual concentration value for the biomolecule of interest. Hence, in various instances, the test device may be a blood glucose, or other such monitor. In a third step, characteristic data of the individual, one or more of their conditions, and/or characteristics of the biomolecule of interest may also be collected. All of this data may be collected, cleaned, input into the data structure, and then be prepared for analysis.

In various embodiments, the data may be labeled and/or categorized, such as with respect to one or more classifications, such as in relation to one or more states or conditions in relation to the presence of one or more biomolecules. For example, a skimmer may be implemented for the purposes of structuring the database, such as for providing a relational structure to the database. And once the database is structured, it may then be populated with data, in accordance with determined or inferred relationships.

In certain instances, a machine learning protocol, as disclosed herein, may be employed so as to determine relationships between data points entered into the database. Such relationships may be determined based on known facts, and as such the learning may be supervised learning, e.g., such as where the data, e.g., spectral and/or biological response data, may be entered into the database and categorized in accordance with one or more categories and/or labels. Known measurement data obtained at relatively the same time can also be entered into the database, can also be categorized, and can then be correlated with the obtained spectral data, so as to convert the spectral data into known spectral data.

A key based on the known factors by which the correspondence between the two data sets may then be generated. In this regard, known factors, e.g., functioning as a key, may be used to label, categorize, and store the newly defined known read data, which key may then be used to inform the search query being sought to be answered, so as to make the return of results faster. Hence, knowing factors by which to label and categorize the data being stored makes building and searching the data storage architecture more efficient.

In other instances, the learning may be inferred, such as in an unsupervised learning. For instance, in certain instances, the data to be stored and structured may not be known, relationships between the data may not have been determined, and the query to be answered may also not be identified. In such instances, the data to be stored is unsupervised, and as such, patterns in data to be stored and their relationships, such as commonalities between data points, need to be determined, but once determined such patterns may then be used in forming the architecture that structures the data storage and/or for converting the previously known data into known data.

For example, where present spectral data is obtained separately from a known measurement data, the spectral read data is unknown, and its relation to other known read and/or known measurement data needs to be determined so as to give meaning to the obtained read data. In such instances, the AI module may be employed to determine the existence of a correlation between the present read data and one or more of past known read data and/or past measurement data. Hence, the AI module may be configured for generating a model by which the present, unknow read data may be compared to known read and/or known measurement data so as to determine a correlation therebetween, and based on that correlation, make a determination, based on the present read data, as to whether the biomolecule is present and if so what its values are, e.g., what its concentration is.

In particular implementations, in performing this process, the AI module may instantiate a machine learning submodule and/or an inference module. For instance, the AI system may implement processes directed at training one or more processing engines of the system to more rapidly, e.g., instantly, recognize an output, such as where the output may be one or more of: the presence and concentration of a biomolecule such as being present within the tissues, based on the type and characteristics of the inputs received, e.g., the sensed unknown spectral array data. The AI system, therefore, may be configured for learning from the inputs it receives, and the results it outputs, so as to be able to draw correlations more rapidly and accurately based on the initial input of data received, e.g., the spectral read data, and the nature of the data structure employed.

As discussed herein above, the input data may be of two general types. In a first instance, the data may be of a type where the output, e.g., the answer, is known. This type of data is input into the system, and used for training purposes. This data may be any form of known data, but in the instances set forth herein, may be spectral measurement data and/or known measurement data pertaining to the biomolecule of interest and/or one or more conditions of the individual. In particular instances, the known measurement data is obtained by the individual carrying out a glucose measurement such as from a blood glucose monitor, e.g., picking their skin and wetting an analyte strip with the resultant blood. This will give the individual a known glucose measurement that they can enter into the system, e.g., via the client app, or it can be transferred from the monitor directly into the system, such as via wireless communication and/or a suitably configured API. Other devices for obtaining accurate glucose measurements may also be employed, such as using the semi-invasive analyte patches described herein.

The second type of data may be data where the answer is unknown, and therefore, must be determined. This data may be any form of data, but where one or more aspects of the data is not known, which in various instances, may be represented by the spectral data related to the biomolecule that is obtained in the absence of known measurement data. In various instances, these two types of data may be used to generate and train an AI model by which unknown biomolecules may be derived from comparing the unknown read data to the model.

For instance, a model may first be generated by building a data structure containing the known read data and the known measurement data, and comparing the two together. Similarities between the two data sets may be defined as factors, and may be used as keys to correlate the known read data with the known measurement data. Once the model is generated, it may be tested, such as by the instantiated machine learning module, so as to train the model.

For training the model, a number of previously unanalyzed, but known spectral read data may be split into two groups. Half of the group may be processed by the analytics system using the model such that new known read data is compared to the system, and the ML module makes a determination, thereby producing an estimated result. The estimated result is compared to the known actual measurement data, and this process is repeated until a desired accuracy and efficiency are attained, such as 90% efficiency and accuracy, such as 95% efficiency and accuracy, such as 99% efficiency and accuracy, such as 99.999% efficiency and accuracy, and the like. Specifically, in training the model, it may be tested against the second half of the known read data again and again until the desired efficiency and accuracy is achieved. Hence, in this manner the model may be trained, such as for measuring and/or determining the presence of a biomolecule based on spectral data where the true measurement outcome is known, e.g., previously determined, e.g., by a blood glucose monitor.

However, once trained, then an inference module of the system may then employ that model so as to substantially instantaneously determine the presence and value, e.g., concentration, of a biomolecule by comparing the measured spectral array data with the trained model. Particularly, in combining these two datasets, e.g., known read data in relation to known measurement data, the AI module may be configured for determining the various interrelationships between them, and based on these interrelationships may develop a model whereby the values of unknown read data may be inferred and/or otherwise predicted based on its factored correlation to the model. Accordingly, at the heart of the AI platform may be a structured architecture, such as a graph or neural network-based data structure, which may be configured for receiving data from a plurality of different reads, taken at a variety of different times in conjunction with associated biomolecule measurement data, and these two data sets can be correlated with one another over implementing a series of ML protocols, so as to generate a model from which biomolecule values may be inferred from generating biomolecule visual spectra data.

Particularly, the known-read/measurement effect data may be used to enhance the AI module's ability to learn from the first type of input data, e.g., where the outcome is known, so as to better predict the outcome for the second kind of input data, unknown but inferred read data, so as to be better correlate the observed spectral data with the presence of a biomolecule or a condition in response thereto, such as in a positive or negative manner. Specifically, based on historical evidence, the AI module may be configured to learn to predict outcomes based on previously observed, e.g., read, data, such as with respect to various of the individual users of the system experiencing the same or similar conditions or affects from having the same or similar conditions with respect to the same or similar biomolecules, where the presence and values of those biomolecules is known. More specifically, a spectral evaluation platform is presented herein, wherein the platform is configured to correlate spectral reflectance data with data pertaining to one or more biomolecules and/or one or more conditions.

As indicated, the system may be configured for employing the measured and/or collected data in one or more learning protocols, such as for machine learning. Particularly, the machine learning component of the disclosure is useful in enabling the system to learn to identify spectral patterns of an individual with the spectral patterns of known molecules being present within living tissues of an individual, but over a prolonged period of time, all of which can be used to characterize the individual so as to identify one or more trends and/or characteristics thereof. Machine learning takes place by training the system to instantly recognize how an output was achieved based on the type and characteristics of the input received, e.g., to infer the presence of a biomolecule based on the spectral measurements being periodically taken of the individual's skin tissues. The present system, therefore, is configured for learning from the inputs it receives, e.g., spectral data, and other evaluation data, and the results it outputs, so as to learn to draw correlations more rapidly and accurately based on the initial input of data received, the results of which can then be used to generate a model that may then be employed by an inference engine of the system so as to make one or more inferences, or predictions based thereon, such as with regard to the presence and value of a biomolecule of interest and/or a present or future state the individual may be experiencing, such as based on the collected spectral data obtained by the biometric sensing and measuring devices set forth herein above.

Accordingly, in view of the above, in one aspect the present disclosure is directed to devices, systems, and their methods of use for generating spectral read data, from which read data a determination of a value of a biomolecule of interest may be made rapidly and accurately in a manner that is continuous and non-invasive. In various embodiments, the system may include one or more continuous sensing and monitoring device, such as for generating the spectral array, a structured database, one or more client computing devices, and one or more server systems. For instance, the system for determining a value of a biomolecule, such as its presence and concentration, may include a structured database, such as a data structure that includes an artificial neural network, for example, wherein part of the database, e.g., at least one library, contains data files pertaining to one or more, e.g., a plurality, of collected spectral read data generated by the sensor devices of the system, and a further library, which may include a model generated from a number of past spectral read data, whereby the presence and value of a biomolecule of interest may be determined in relation to the model, or via use of one or more other data structures. A further library may also be include, such as where the further library includes a description for one or more, e.g., a plurality of environmental and/or user health conditions.

Further, in various embodiments, the system may include a client computing device having a display coupled therewith, such as for displaying a graphical user interface that is generated by one or more of the client computing devices and/or a server associated therewith. For example, in a particular embodiment, an individual's body in need of monitoring, conditioning, and/or maintenance may be defined, its conditions determined, and an ideal health maintenance regime and conditions for one or more improvements of a present condition may be determined. Accordingly, a user, such as an individual suffering from a disease, such as diabetes, may engage the user interface of the client computing device for the purpose of defining one or more health objectives and/or conditions that may be useful for achieving one or more wellness goals of one or more individuals such as for improved wellbeing.

Particularly, an individual, e.g., suffering from diabetes, may access one or more controls of an interactive dashboard presented at the graphical user interface so as to take a glucose value measurement, whereby one or more spectral readings, related to the presence and/or concentration of glucose, may be collected by the sensors of the system and analyzed by an associated computing facility so as to determine a present glucose value and/or one or more suggestions for a lifestyle change in view of those glucose values may be suggested, such as with respect to the personal characteristics of one or more persons engaging with the system. For instance, the GUI presented at the display of the client computing device may be configured for displaying a list of interview questions and/or condition characteristics of the user, for receiving, such as via one or more controls of a dashboard interface, the individual's responses, selections, and/or instructions to the interview questions, which once received, the responses may then be transmitted, such as by a suitably configured communications module to an associated server system, whereby a data profile for the user may be determined and may be used in conjunction with the measurement data generated herein so to determine and track progress towards one or more health goals, and to determine manners by which these goals may be better achieved.

The system, therefore, may include a server system, such as a server that is connected to one or both of the database and the client computing device via a network connection. Particularly, in various implementations, the server system may be configured for generating one or more health goal condition modules, which module may be adapted for providing the referenced graphical user interface to the client computing device for local display thereby. More particularly, in certain instances, the client computing device may be used by the user for generating and/or selecting operational parameters for configuring the various modules to maximize progress toward the defined goals. However, in particular instances, the server system may be employed, or otherwise configured to autonomously generate achievable steps for achieving and/or maintaining those goals, such as in an intuitive manner.

Embodiments of the disclosure and all of the functional operations described in this specification can be implemented in digital electronic circuitry, or in computer software, firmware, or hardware, including the structures disclosed in this specification and their structural equivalents, or in combinations of them. Embodiments of the disclosure can be implemented as one or more computer program products, e.g., one or more modules of computer program instructions encoded on a computer readable medium, e.g., a machine readable storage device, a machine readable storage medium, a memory device, or a machine-readable propagated signal, for execution by, or to control the operation of, data processing apparatus. Further operations may be performed by one or more modules of a suitably trained AI system, without the need for written code.

The term "data processor" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of them. A propagated signal is an artificially generated signal, e.g., a machine-generated electrical, optical, or electromagnetic signal, that is generated to encode information for transmission to suitable receiver apparatus.

A computer program (also referred to as a program, software, an application, a software application, a mobile application, a script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer.

Generally, a processor will receive instructions and data from a read only memory or a random access memory or both. The essential elements of a computer are a processor for executing instructions and one or more memory devices for storing instructions and data. Generally, a computer will also include, or be operatively coupled to, a communication interface to receive data from or transfer data to, or both, one or more mass storage devices for storing data, e.g., magnetic, magneto optical disks, or optical disks. Moreover, a computer can be embedded in another device, e.g., a mobile telephone, a personal digital assistant (PDA), a mobile audio player, a Global Positioning System (GPS) receiver, to name just a few.

Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the disclosure can be implemented on a computer having a display device, e.g., a capacitive sensing touch screen device, including a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the disclosure can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the invention, or any combination of such back end, middleware, or front end components. The components of the system can be interconnected by any form or medium of digital data communication, e.g., a communication network. Examples of communication networks include a local area network ("LAN") and a wide area network ("WAN"), e.g., the Internet. The computing system can include clients and servers. A client and server are generally remote from each other and typically interact through a communication network. The relationship of client and server arises by virtue of computer programs running on the respective computers and having a client-server relationship to each other.

Certain features which, for clarity, are described in this specification in the context of separate embodiments, may also be provided in combination in a single embodiment. Conversely, various features which, for brevity, are described in the context of a single embodiment, may also be provided in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Particular embodiments of the invention have been described. Other embodiments are within the scope of the following claims. For example, the steps recited in the claims can be performed in a different order and still achieve desirable results. In addition, embodiments of the invention are not limited to database architectures that are relational; for example, the invention can be implemented to provide indexing and archiving methods and systems for databases built on models other than the relational model, e.g., navigational databases or object-oriented databases, and for databases having records with complex attribute structures, e.g., object-oriented programming objects or markup language documents. The processes described may be implemented by applications specifically performing archiving and retrieval functions or embedded within other applications.

Although a few embodiments have been described in detail above, other modifications are possible. Other embodiments may be within the scope of the following claims.

The invention claimed is:

1. A biometric sensor system for determining a characteristic of a state of a user based on a value of a biomolecule within a body tissue, the system comprising:

- an attachment structure having an elongated surface member, the elongated surface member having an inner portion and an outer portion, the outer portion being defined by a perimeter including a top surface and a bottom surface, and the inner portion being defined by an opening, the bottom surface of the perimeter including an attachment element for attachment to the body tissue of a user;
- a biomolecule sensing device housing member having a plurality of horizontally extended flat surfaces including a first flat surface and a second flat surface, the plurality of flat surfaces being offset from one another by a bounding surface, the bounding surface being positioned substantially normal to the first and second flat surfaces, together the first flat surface and the bounding surface forming a dome, the dome defining a first cavity of the housing member, and the second flat surface configured for both covering the cavity and forming an attachment interface, the second flat surface having an opening therethrough, the opening being aligned with a portion of the cavity, and the attachment interface extending laterally outwards from the dome by which the housing member may be coupled to the attachment structure in a manner that the opening of the second flat surface is coincident with the opening of the attachment structure;
- a transparent window member positioned to cover the opening of the second flat surface; and
- a biomolecule sensing device configured for being positioned within the opening of the cavity of the dome so as to be encased within the housing member, the biomolecule sensing device comprising:
  and
  - a biomolecule sensor unit for detecting a characteristic of a bodily response due to a presence of the biomolecule within the body tissue, the biomolecule sensor unit comprising:
    - a printed circuit board having a sensor array coupled therewith, the sensor array including a sensor unit having one or more photoemitters and one or more photoreceivers, each being arranged on the printed circuit board within in the housing proximate the transparent window opposite the user's body tissue, the one or more photoemitters configured to illuminate, at a predetermined frequency and interval of light, the user's tissue below the transparent window, and each of the one more photoreceivers configured to receive a return of the light reflected back from the user's tissue below the transparent window and to generate a return signal in response to collecting the reflected light, the printed circuit board further comprising a processing unit configured for pre-processing the return signal based on the return of the light reflected back from the user's tissue.

2. The biometric sensor system in accordance with claim 1, wherein the sensor array comprises a plurality of sensor units, the plurality of sensor units including a first sensor unit and a second sensor unit.

3. The biometric sensor system in accordance with claim 2, wherein the first sensor unit includes six photoemitters surrounding at least a first photoreceiver.

4. The biometric sensor system in accordance with claim 3, wherein the six photoemitters comprise: a first photoemitter for emitting light of a first wavelength within the range from about 1000 nm and about 1100 nm, a second photoemitter for emitting light of a second wavelength within the range from about 1100 nm and about 1200 nm, a third photoemitter for emitting light of a third wavelength within the range from about 1200 nm and about 1300 nm, a fourth photoemitter for emitting light of a fourth wavelength within the range from about 1300 nm to about 1450 nm, a fifth photoemitter for emitting light of a fifth wavelength within the range from about 1450 nm to about 1550 nm, and a sixth photoemitter for emitting light of a sixth wavelength within the range from about 1550 nm to about 1650 nm.

5. The biometric sensor system in accordance with claim 4, wherein the second sensor unit includes four additional photoemitters surrounding at least a second photoreceiver.

6. The biometric sensor system in accordance with claim 5, wherein the four additional photoemitters comprise: a seventh photoemitter for emitting light of a seventh wavelength within the range from about 550 nm to about 650 nm, an eighth photoemitter for emitting light of an eighth wavelength within the range from about 650 nm to about 850 nm, a ninth photoemitter for emitting light of a ninth wavelength within the range from about 850 to about 940 nm, and a tenth photoemitter for emitting light of a tenth wavelength within the range from about 940 nm to about 1000 nm.

7. The biometric sensor system in accordance with claim 6, wherein the first photoreceiver is configured for receiving and detecting light waves in the range from about 500 nm to about 1000 nm.

8. The biometric sensor system in accordance with claim 7, wherein the second photoreceiver is configured for receiving and detecting light waves in the range from about 1000 nm to about 1700 nm.

9. The biometric sensor system in accordance with claim 2, wherein the first sensor unit comprises at least three photoemitters including a first photoemitter for emitting light of a green wavelength, a second photoemitter for emitting light of a red wavelength, and a photoemitter for emitting light of a near-infrared wavelength, the at least three photoemitters partially surrounding a photodiode.

10. The biometric sensor system in accordance with claim 9, wherein the second sensor unit comprises a microwave sensor having a microwave antenna array emitter.

11. The biometric sensor system in accordance with claim 10, further comprising a galvanic skin response sensor including a plurality of contacts, the plurality of contacts being positioned within the second flat surface of the housing of the biomolecule sensing device at opposite sides of the first or second sensor units.

12. The biometric sensor system in accordance with claim 11, further comprising an infrared temperature sensor, the infrared temperature sensor being positioned within the second flat surface of the housing of the biomolecule sensing device and being configured for determining a body temperature of the user.

13. The biometric sensor system in accordance with claim 12, further comprising a pulse oximeter sensor positioned within the second flat surface of the housing of the biomolecule sensing device.

14. The biometric sensor system in accordance with claim 13, further comprising a plurality of conductive charging interfaces positioned within the second flat surface of the housing, the conductive charging interfaces for charging a battery of the sensor system.

15. The biometric sensor system in accordance with claim 14, further comprising a remote computing device, and wherein the biometric sensing device further comprises a plurality of communication ports positioned within the second flat surface of the housing, the communication ports being configured for effectuating data transmission of the pre-processed return signal between the biometric sensing device and the remote computing device, further wherein the remote computing device is configured for receiving the pre-processed return signal data transmission from the biomolecule sensing device and further processing the return signal data so as to determine the characteristic of the state of the user.

16. A biometric sensor system for determining a characteristic of a state of a user based on a value of a biomolecule suspected of being present within a body tissue of the user, the system comprising:

a biomolecule sensing apparatus for generating biomolecule effect data, the biomolecule sensing apparatus comprising:

a biomolecule sensing device configured for generating digital signal read data pertaining an effect of a biomolecule on the tissue of the body of a user, the biomolecule sensing device comprising:

a housing having a top member coupled to a bottom member so as to form a cavity therebetween, together the housing and the cavity for retaining an electronic sensing unit within the bottom member having a transmissive portion positioned therein, the electronic sensing components including:

an electronic sensing unit being positioned within the cavity of the housing, the electronic sensing unit comprising a plurality of sensor arrays, a first sensor array including a microwave emitter for emitting and directing electromagnetic radiation within a range of microwaves into the tissue of the body of the user, and further including a microwave detector for receiving returned microwaves that have been transmitted through the body tissue, and a second sensor array including a photoemitter for directing electromagnetic radiation through the transmissive portion of the bottom member of the housing and into the body tissue, the body tissue suspected of being affected by the presence of the biomolecule, and a photoreceiver for receiving electromagnetic radiation reflected back from the body tissue, together the first and second sensor arrays being configured for generating raw electromagnetic radiation data;

an analog to digital converter for converting the raw electromagnetic radiation data into digital signal read data; and a communications module for transmitting the digital signal data; and a computing system for determining an effect of the biomolecule on the tissue of the user, the computing system comprising:

a communications module for receiving the transmitted digital signal read data, and an analytics module for determining a characteristic of a state of the user of the biomolecule sensing apparatus, the analytics module comprising one or more sets of processing elements configured for accessing the digital signal read data, processing the digital signal data to determine both a value of the biomolecule and a reaction of the tissue to the biomolecule, and outputting analytic result data characterizing one or more states of the user based on the value of the biomolecule within the tissue.

17. The biometric sensor system in accordance with claim 16, wherein the determining of the value of the biomolecule comprises subjecting the digital signal read data to a model based on historic digital signal read data.

18. The biometric sensor system in accordance with claim 17, wherein the determining of the reaction of the tissue to the biomolecule includes detecting a change in absorption and reflectance of the skin.

19. The biometric sensor system in accordance with claim 18, wherein the first sensor array comprises one or more microwave antennas and the second sensor array comprises at least three photoemitters.

20. The biometric sensor system in accordance with claim 19, wherein the second sensor unit comprises a PPG sensor for generating raw PPG data.

* * * * *